(12) United States Patent
Pham et al.

(10) Patent No.: US 10,640,818 B2
(45) Date of Patent: *May 5, 2020

(54) COMPOSITIONS AND METHODS FOR SELECTION OF NUCLEIC ACIDS

(71) Applicant: Pacific Biosciences of California, Inc., Menlo Park, CA (US)

(72) Inventors: Thang Tat Pham, Mountain View, CA (US); Yu-Chih Tsai, Fremont, CA (US); Jonas Korlach, Camas, WA (US); Tyson A. Clark, Menlo Park, CA (US); Stephen Turner, Seattle, WA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 279 days.

This patent is subject to a terminal disclaimer.

(21) Appl. No.: 15/353,595

(22) Filed: Nov. 16, 2016

(65) Prior Publication Data

US 2017/0145492 A1 May 25, 2017

Related U.S. Application Data

(63) Continuation of application No. 14/069,067, filed on Oct. 31, 2013, now Pat. No. 9,528,107.

(60) Provisional application No. 61/789,354, filed on Mar. 15, 2013, provisional application No. 61/721,339, filed on Nov. 1, 2012.

(51) Int. Cl.
| | | |
|---|---|---|
| *C12Q 1/68* | (2018.01) | |
| *C07H 21/00* | (2006.01) | |
| *C12Q 1/6855* | (2018.01) | |
| *C12N 15/10* | (2006.01) | |
| *C12P 19/34* | (2006.01) | |

(52) U.S. Cl.
CPC ....... *C12Q 1/6855* (2013.01); *C12N 15/1072* (2013.01); *C12P 19/34* (2013.01)

(58) Field of Classification Search
CPC ................................. C12Q 1/68; C07H 21/00
See application file for complete search history.

(56) References Cited

U.S. PATENT DOCUMENTS

| | | | | |
|---|---|---|---|---|
| 5,324,632 A * | 6/1994 | Weisburg | ............ | C12Q 1/6895 435/6.12 |
| 5,352,604 A | 10/1994 | Wilson et al. | | |
| 5,376,528 A * | 12/1994 | King | .................... | C12Q 1/6813 435/6.11 |
| 5,587,305 A | 12/1996 | Briggs et al. | | |
| 5,707,811 A * | 1/1998 | Ferrin | ..................... | C12N 15/10 435/5 |
| 5,710,000 A | 1/1998 | Sapolsky et al. | | |
| 5,714,318 A | 2/1998 | Sagner et al. | | |
| 5,759,780 A * | 6/1998 | Parker | ................ | C12N 15/1072 435/6.14 |
| 6,180,778 B1 * | 1/2001 | Bastian | .............. | C12N 15/1006 536/25.3 |
| 6,214,587 B1 * | 4/2001 | Dattagupta | .......... | C12Q 1/6844 435/287.2 |
| 6,235,502 B1 | 5/2001 | Weissman et al. | | |
| 6,361,947 B1 | 3/2002 | Dong et al. | | |
| 6,451,563 B1 * | 9/2002 | Wittig | .................... | C12N 15/10 435/194 |
| 6,498,023 B1 * | 12/2002 | Abarzua | ................ | C12N 15/10 435/6.1 |
| 6,917,726 B2 | 7/2005 | Levene et al. | | |
| 7,013,054 B2 | 3/2006 | Levene et al. | | |
| 7,033,764 B2 | 4/2006 | Korlach et al. | | |
| 7,052,847 B2 | 5/2006 | Korlach et al. | | |
| 7,056,661 B2 | 6/2006 | Korlach et al. | | |
| 7,056,676 B2 | 6/2006 | Korlach et al. | | |
| 7,170,050 B2 | 1/2007 | Turner et al. | | |
| 7,181,122 B1 | 2/2007 | Levene et al. | | |
| 7,205,105 B2 | 4/2007 | Afonina et al. | | |
| 7,292,742 B2 | 11/2007 | Levene et al. | | |
| 7,302,146 B2 | 11/2007 | Turner et al. | | |
| 7,384,737 B2 | 6/2008 | Barnes | | |
| 7,683,035 B1 * | 3/2010 | Erbacher | ............ | C12N 15/1003 424/450 |
| 7,745,116 B2 | 6/2010 | Williams | | |
| 7,901,889 B2 | 3/2011 | Christians et al. | | |
| 7,910,302 B2 | 3/2011 | Drmanac et al. | | |
| 7,910,354 B2 | 3/2011 | Drmanac et al. | | |

(Continued)

FOREIGN PATENT DOCUMENTS

| | | |
|---|---|---|
| WO | 2007/075873 A2 | 7/2007 |
| WO | 2007/075987 A2 | 7/2007 |

(Continued)

OTHER PUBLICATIONS

Buchholz, F. Current Opinion in Biotechnology 20 :383 (2009). (Year: 2009).*

(Continued)

*Primary Examiner* — Ethan C Whisenant

(74) *Attorney, Agent, or Firm* — David C. Scherer

(57) ABSTRACT

Methods are provided for reducing the complexity of a population of nucleic acids prior to performing an analysis of the nucleic acids, e.g., sequence analysis. The methods result in a subset of the initial population enriched for a target region, which is typically located within one or more target fragments. The methods are particularly useful for analyzing populations having a high degree of complexity, e.g., chromosomal-derived DNA, whole genomic DNA, or mRNA populations.

18 Claims, 11 Drawing Sheets

Specification includes a Sequence Listing.

(56) References Cited

U.S. PATENT DOCUMENTS

| | | | |
|---|---|---|---|
| 8,003,330 B2 | 8/2011 | Heiner et al. | |
| 8,143,030 B2 | 3/2012 | Maxham et al. | |
| 8,153,375 B2 | 4/2012 | Travers et al. | |
| 8,236,499 B2 | 8/2012 | Patel et al. | |
| 8,883,420 B2 | 11/2014 | Marillonnet et al. | |
| 9,528,107 B2* | 12/2016 | Pham | C12N 15/1072 |
| 9,938,590 B2* | 4/2018 | Pollner | C12Q 1/6837 |
| 2001/0031473 A1* | 10/2001 | Dattagupta | C12N 15/1003 435/6.18 |
| 2001/0041340 A1* | 11/2001 | Kingsmore | C12Q 1/6804 435/6.12 |
| 2001/0047091 A1* | 11/2001 | Miki | C07K 14/415 536/24.1 |
| 2002/0164634 A1 | 11/2002 | Patil et al. | |
| 2002/0182598 A1 | 12/2002 | Zhang et al. | |
| 2003/0059955 A1 | 3/2003 | Barndad | |
| 2004/0115616 A1 | 6/2004 | Holton | |
| 2005/0019776 A1 | 1/2005 | Callow et al. | |
| 2005/0069991 A1* | 3/2005 | Hyman | C12N 9/1205 435/91.2 |
| 2005/0100911 A1 | 5/2005 | Patil et al. | |
| 2005/0272065 A1* | 12/2005 | Lakey | C12Q 1/6858 435/6.12 |
| 2006/0040300 A1 | 2/2006 | Dapprich et al. | |
| 2007/0003938 A1 | 1/2007 | Fu et al. | |
| 2007/0031857 A1 | 2/2007 | Makarov et al. | |
| 2007/0161017 A1 | 7/2007 | Eid et al. | |
| 2007/0287151 A1 | 12/2007 | Linnarsson | |
| 2008/0090733 A1 | 4/2008 | Dapprich et al. | |
| 2008/0268508 A1* | 10/2008 | Sowlay | C12N 15/1096 435/91.2 |
| 2009/0029385 A1* | 1/2009 | Christians | C12Q 1/6869 435/6.12 |
| 2009/0047674 A1 | 2/2009 | Dapprich et al. | |
| 2009/0123913 A1* | 5/2009 | Barany | B82Y 5/00 435/6.14 |
| 2009/0162845 A1 | 6/2009 | Rabbani et al. | |
| 2009/0233291 A1 | 9/2009 | Chen et al. | |
| 2009/0263798 A1 | 10/2009 | Dapprich et al. | |
| 2009/0264299 A1 | 10/2009 | Drmanac et al. | |
| 2009/0298075 A1* | 12/2009 | Travers | C12Q 1/6869 435/6.12 |
| 2009/0305419 A1* | 12/2009 | Miller | C12N 15/907 435/455 |
| 2010/0081128 A1 | 4/2010 | Drmanac et al. | |
| 2010/0120098 A1 | 5/2010 | Grunenwald et al. | |
| 2010/0286070 A1 | 11/2010 | Verheyden et al. | |
| 2011/0009281 A1 | 1/2011 | Micklem et al. | |
| 2011/0033854 A1 | 2/2011 | Drmanac et al. | |
| 2011/0183320 A1 | 7/2011 | Flusberg et al. | |
| 2011/0281736 A1 | 11/2011 | Drmanac et al. | |
| 2011/0287512 A1* | 11/2011 | Paschon | C12N 15/62 435/196 |
| 2012/0071359 A1 | 3/2012 | Sun et al. | |
| 2012/0196279 A1 | 8/2012 | Underwood et al. | |
| 2012/0258868 A1 | 10/2012 | Sapolsky et al. | |
| 2012/0322666 A1 | 12/2012 | Pham et al. | |
| 2012/0322692 A1 | 12/2012 | Pham et al. | |
| 2013/0116130 A1 | 5/2013 | Fu et al. | |
| 2013/0177915 A1 | 7/2013 | Too et al. | |
| 2013/0323725 A1 | 12/2013 | Peter et al. | |
| 2014/0329282 A1 | 11/2014 | Nelson et al. | |
| 2015/0105275 A1 | 4/2015 | Wong et al. | |
| 2015/0315581 A1* | 11/2015 | Han | C12N 15/111 514/44 A |

FOREIGN PATENT DOCUMENTS

| | | |
|---|---|---|
| WO | 2007/076057 A2 | 7/2007 |
| WO | 2012/065043 A2 | 5/2012 |

OTHER PUBLICATIONS

Boom et al.,Rapid and Simple Method for purification of nucleic acids. Journal of Clinical Microbiology 28(3) :495-503 (Year: 1990).*
International Search Report and Written Opinion dated Jan. 20, 2014 for related case PCT/US2013/067867.
International Preliminary Report on Patentability dated May 14, 2015 for related case PCT/US2013/067867.
Akhmedov, et al. "Human 100-kDa Homologous DNA-Pairing Protein is the Splicing Factor PSF and Promotes DNA Strand Invasion," Nucleic Acids Res. (2000) 28(16):3022-30.
Barany, F. "The Ligase Chain Reaction in a PCR World," Genome Res. (1991) 1: 5-16.
Bi, et al. "Human and Yeast Rad52 Proteins Promote DNA Strand Exchange," Proc. Natl. Acad. Sci. U.S.A. (2004) 101(26):9568-72.
Callow, et al. "Selective DNA Amplification from Complex Genomes Using Universal Souble-Sided Adapters," Nucleic Acids Res. (2004) 32(2):e21.
Demidov, et al. "Duplex DNA Capture," Curr. Issues Mol. Biol. (2000) 2(1):31-35.
Dhopeshwarkar, et al. "Electrokinetic Concentration Enrichment within a Microfluidic Device Using a Hydrogel Microplug," Lab Chip (2005) 5:1148-1154.
Ferrin, et al. "Sequence-Specific Ligation of DNA Using RecA Protein," Proc. Natl. Acad. Sci. U.S.A. (1998) 95:2152-2157.
Gibson, et al. "Chemical Synthesis of the Mouse Mitochondrial Genome," Nature Methods (2010) 7:901-903.
Gibson, et al. "Enzymatic Assembly of DNA Molecules up to Several Hundred Kilobases," Nature Methods (2009) 6:343-345.
Honigberg, et al. "Ability of RecA Protein to Promote a Search fo Rare Sequences in Duplex DNA," Proc. Natl. Acad. Sci. U.S.A. (1986) 83:9586-9590.
Huang, et al. "Solid-Phase Purification of Gene Synthesis Products Using Magnetic Beads," Proc. of SPIE (2008) 7269:A1-11.
Jordan, et al. "Genome Complexity Reduction for SNP Genotyping Analysis," Proc. Natl. Acad. Sci. U.S.A. (2002) 99(5):2942-7.
Mertes, et al. "Targeted Enrichment of Genomic DNA Regions for Next-Generation Sequencing," Briefings in Functional Genomics (2011) 10(6):374-386.
Naumann, et al. "A Distinct DNA-Methylation Boundary in the 5'-Upstream Sequence of the FMR1 Promoter Binds Nuclear Proteins and is Lost in Fragile X Syndrome," Am. J. Hum. Genet. (2009) 85(5):606-616.
Noirot, et al. "DNA Strand Invasion Promoted by Escherichia coli ReeT Protein," J. Biol. Chem. (1998) 273(20):12274-80.
Rigas, et al. "Rapid Plasmid Library Screening Using RecA-Coated Biotinylated Probes," Proc. Natl. Acad. Sci. U.S.A. (1986) 83:9591-9595.
Rybalchenko, et al. "Strand Invasion Promoted by Recombination Protein β of Coliphage λ," Proc. Natl. Acad. Sci. U.S.A. (2004) 101(49):17056-60.
Taidi-Laskowski, et al. "Use of RecA Protein to Enrich for Homologous Genes in a Genomic Library," Nucleic Acids Res. (1988) 16(16):8157-8169.
Vieregg, et al. "Selective Nucleic Acid Capture with Shielded Covalent Probes," J. Am. Chem. Soc. (2013) 135(26):9691-9699.
Weisner, et al. "Purification of Mitochondiral DNA from Total Cellular DNA of Small Tissue Samples," Gene (1991) 98:277-281.
Wilkinson, et al. "Selective 2'-Hydroxyl Acylation Analyzed by Primer Extension (SHAPE): Quantitative RNA Structure Analysis at Single Nucleotide Resolution," Nature Protocols (2006) 1(3):1610-1616.
Xu, et al. "A Dynamic RecA Filament Permits DNA Polymerase-Catalyzed Extension of the Invading strand in Recombination Intermediates," J. Biol. Chem (2002) 277(16):14321-14328.
Zaghloul, et al. "Optimizing Anti-Gene Oligonucleotide 'Zorro-LNA' for Improved Strand Invasion into Duplex DNA," Nucleic Acids Res (2011) 39(3):1142-1154.
Zhou, et al. "Method to Purify Mitochondrial DNA Directly from Yeast Total DNA," Plasmid (2010) 64:196-199.
Eid, et al. "Real-Time DNA Sequencing from Single Polymerase Molecules," Science (2009) 323:133.

(56) References Cited

OTHER PUBLICATIONS

Engler, et al. "A One Pot, One Step, Precision Closing Method with High Throughput Capability," PLoS One 3 (2008) 3(11):e3647.
Sommer, et al. "Minimal Homology Requirements for PCR Primers," Nucleic Acids Research (1989) 17(16):6749.
Wang, et al. "Rolling Cirlce Amplification-Mediated Hairpin RNA (RMHR) Library Construction in Plants," Nucleic Acids Research (2008) 36(22):e149
Williams, et al. "Cloning Restriction Fragments That Promote Expression of a Gene in Bacillus Subtillis," J. of Bacteriology (1981) 146(3):1162.

* cited by examiner

↓ Anneal and ligate adaptors at 65°C

↓ Single-strand-dependent exonuclease treatment

↓ Gap repair

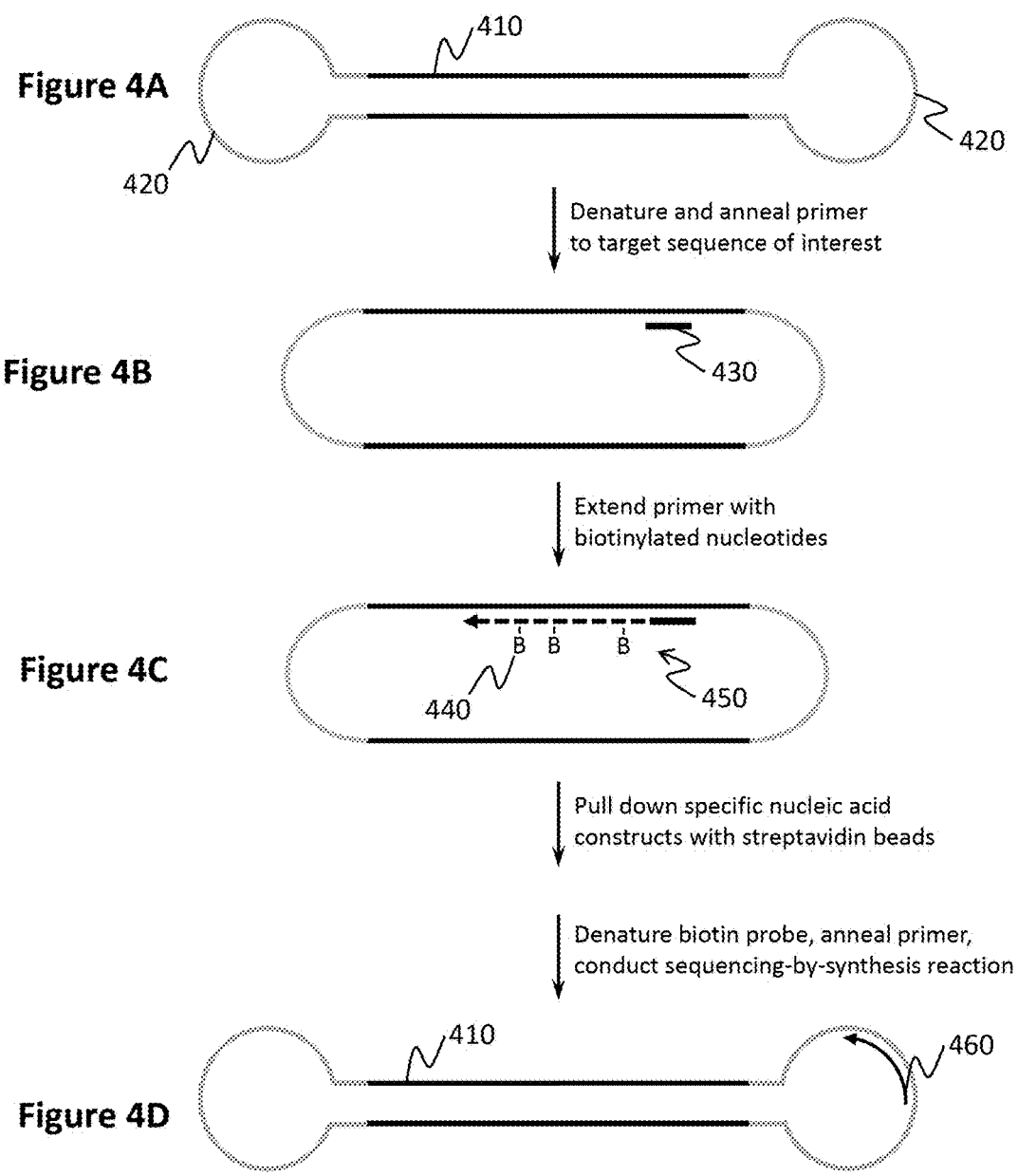

COMPOSITIONS AND METHODS FOR SELECTION OF NUCLEIC ACIDS

CROSS-REFERENCE TO RELATED APPLICATIONS

This application is a continuation of U.S. patent application Ser. No. 14/069,067, filed on Oct. 31, 2013, which claims the benefit of U.S. Provisional Application No. 61/721,339, filed on Nov. 1, 2012 and U.S. Provisional Application No. 61/789,354, filed Mar. 15, 2013, which are incorporated herein by reference in their entireties for all purposes. This application is further related to U.S. Provisional Application No. 61/721,206, filed Nov. 1, 2012; U.S. patent application Ser. No. 14/068,293, filed on Oct. 31, 2013; U.S. Provisional Application No. 61/617,999, filed Mar. 30, 2012; U.S. patent application Ser. No. 13/836,806, filed Mar. 15, 2013; U.S. Provisional Patent Application No. 61/799,237, filed Mar. 15, 2013; and U.S. patent application Ser. No. 13/363,066, filed Jan. 31, 2012, all of which are incorporated herein by reference in their entireties for all purposes.

STATEMENT REGARDING FEDERALLY SPONSORED RESEARCH

Not Applicable.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system, and is hereby incorporated by reference in its entirety for all purposes. The txt file submitted herewith contains only 6 KB file (01012704_2017-01-30 SeqListing.txt).

BACKGROUND OF THE INVENTION

It is often desirable to selectively isolate molecules present in a low concentration in a sample, e.g., to facilitate analysis of such molecules without the interference of other more prevalent components of the sample. For example, in the analysis of nucleic acid sequences, actively selecting a portion of the sample nucleic acid that comprises a region of interest can allow a researcher to focus their analytical efforts only on those portions of the nucleic acid sample. As such, the resulting "enriched" nucleic acid sample has a much higher proportion of nucleic acids having the region to be analyzed. Further, in some cases the concentration of a particular molecule in a sample is simply too low, rendering analysis impossible without some sort of concentration of the molecule.

Selectively enriching a sample for a molecule of interest can be performed in various ways known to those of skill in the art. For example, affinity tags have been used for purification of specific molecules of interest from a biological sample using an affinity technique. These tags are covalently or non-covalently linked to the molecules of interest. For example, an affinity tag can be incorporated into a protein of interest to form a fusion protein. The affinity tag further binds to an immobile phase, e.g., a substrate or matrix (e.g., within a column). Once bound, the substrate or matrix is washed to remove all unbound components of the sample leaving only those bound via the affinity tag. Often these tags are removable by chemical agents or by enzymatic means, such as proteolysis, which allows for removal of the selected molecules from the substrate or matrix while leaving the affinity tag behind. Once removed, the selected molecules can be further analyzed or otherwise manipulated.

With regards to isolation of specific nucleic acid sequence ("target nucleic acid") in a complex sample (e.g., a genomic DNA sample), various methods are known in the art. Notably, "hybrid capture" methods use a nucleic acid complementary to the sequence or sequences of interest to specifically hybridize to one or more target nucleic acids. However, where a region of interest represents a very small portion of the total sample, hybridization strategies can be difficult and require massive amplification of the original sample to provide enough of the region of interest to be efficiently selected. In some cases, identification of rare mutations within the region of interest is an object of a study, and since amplification strategies are known to introduce a small number of mutations into the resulting amplicons, these amplification-introduced mutations can complicate the identification of the true rare mutations present in the original sample, especially where single-molecule sequencing strategies are utilized. Accordingly, is desirable to provide reaction components that provide a way to select one or more regions of interest from a complex sample and isolate them from other molecules in the sample to facilitate their analysis, preferably without requiring amplification. The present invention provides these and other solutions.

BRIEF SUMMARY OF THE INVENTION

Methods are provided for reducing the complexity of a population of nucleic acids prior to performing an analysis of the nucleic acids, e.g., sequence analysis, cloning, amplification, etc. In preferred embodiments, the methods result in a subset of the initial population enriched for a desired region of interest. The methods are particularly useful for analyzing populations having a high degree of complexity, e.g., chromosomal-derived DNA, whole genomic DNA, or mRNA populations. In addition, such methods allow for analysis of pooled samples.

In preferred aspects, methods are provided for enrichment of a target region in a nucleic acid sample that comprise: a) fragmenting the nucleic acid sample to generate a mixture of double-stranded fragments, where a minority of the double-stranded fragments in the mixture comprise the target region, and a majority of the double-stranded fragments in the mixture do not comprise the target region; and b) selectively degrading the majority of the double-stranded fragments in the mixture that do not comprise the target region in the presence of the minority of the double-stranded fragments that comprise the target region, wherein the minority of the double-stranded fragments that comprise the target region are protected from the degrading, thereby enriching the mixture for the double-stranded fragments that comprise the target region. In preferred embodiments, type IIs restriction enzymes are used in the fragmenting to generate the double-stranded fragments, wherein the minority of the double-stranded fragments comprising the target region have known overhang sequences at both ends. In preferred embodiments, ligation of two stem-loop adapters to the double-stranded fragments that comprise the target region protects them from being degraded. Optionally, further enrichment is achieved by exposing the double-stranded fragments that comprise the target region to a primer and polymerase enzyme to generate a polymerase complex, and exposing the polymerase complex to a capture-hook oligonucleotide attached to a magnetic bead to selectively capture the polymerase complex. Preferably, the capture-hook oligonucleotide only captures an active polymerase complex by binding to a region of one of the stem-loop adapters that has been rendered single-stranded by the polymerase enzyme.

In certain aspects, methods are provided for enriching a target region in a nucleic acid sample. In some preferred embodiments, the methods comprise a) digesting the nucleic acid sample with a restriction enzyme that cuts a defined distance from its recognition site to produce a population of double-stranded nucleic acid fragments, wherein fragments containing the target region have known single-stranded overhangs on each end, each overhang being different; b) ligating two types of stem-loop adapters to the population of nucleic acid fragments, wherein one type of stem-loop adapter has a single-stranded overhang sequence complementary to a first of the known single-strand overhangs at one end of the fragment comprising the target region, and the other type of stem-loop adapter has a single-stranded overhang sequence complementary to a second of the known single-stranded overhangs on the other end of the fragment comprising the target region; and c) treating the sample with one or more exonucleases to digest the double-stranded nucleic acid fragments that have one or no stem-loop adapter linked thereto, thus enriching for the target region in the nucleic acid sample. Optionally, restriction enzymes chosen to cleave fragments over than the fragments comprising the target region are added to the population of fragments prior to or during said treating. A primer binding sequence is preferably present within at least one of the adapters, and can have a primer bound thereto. Such a primer can be complementary only to the adapter, or can also be complementary to a portion of the target region. In some embodiments, the primer comprises modified bases that hybridize to the portion of the target region. The fragments not digested in step c can be optionally subjected to a sequencing reaction, preferably a long-range sequencing reaction, which may be a sequencing-by-syntheis reaction, a nanopore-based sequencing reaction, a Sanger sequencing reaction, or other sequencing reaction. In some embodiments, the sequencing reaction generates redundant sequence information from single molecules of the fragments not digested in step c. The sample nucleic acids are not amplified in some embodiments, and in other embodiments they are amplified prior to the ligating, e.g., using a rolling-circle amplification method. The adding preferably comprises covalent attachment of stem-loop adapters to the fragment comprising the target region, and in especially preferred embodiments, two different stem-loop adapters are attached, e.g., via a ligation reaction. The sample nucleic acids can be native or amplified nucleic acids, genomic DNA, cDNA, cloned DNA, modified DNA, or any other nucleic acids that can be manipulated by the methods described herein. Further, in certain embodiments, rather than degrading the non-target fragments, they are treated with a terminal transferase to add a polyA tail, and the polyA tail is annealed to a polyT tail on a solid surface (e.g., microarray, magnetic bead, column, etc.) to allow pull-down of the non-target fragments and recovery of the target fragments that are still in solution because they are flanked by stem-loop adapters and therefore are not a substrate for the terminal transferase. Optionally, a ligase reaction can be performed to repair nicks in the double-stranded nucleic acid fragments prior to adding polyA tails in order to prevent addition of polyA tails at internal positions in the fragments.

In some aspects, methods for enrichment of a target region in a nucleic acid sample comprise: a) providing a driver population complementary to a target region in the nucleic acid sample; b) hybridizing the driver population to the target region the nucleic acid sample to generate driver-target complexes comprising a duplex region that comprises one strand of the target region and one strand from the driver population; and c) immobilizing the driver-target complexes and removing other nucleic acids in the nucleic acid sample, thereby enriching for the target region in the nucleic acid sample. In some embodiments, the driver population comprises an affinity tag and the immobilizing comprises binding of the affinity tag to a solid surface. In other embodiments, the driver population comprises a magnetic bead, and the immobilizing comprises binding of the magnetic bead to a magnetic surface. In certain embodiments, the driver population is coated with a strand exchange protein, e.g., RecA, RecT, Rad51/Rad52, human splicing factor PSF, protein beta of coliphage lambda, or a combination thereof. In some embodiments, the hybridizing takes place in the presence of one or more helicases and/or single-stranded DNA binding proteins. The driver population can comprise modified nucleotides that increase a melting temperature of the driver-target complexes, thereby increasing their stability during the immobilizing, e.g., locked nucleic acids (LNAs), protein nucleic acids (PNAs), or 2'-O-methyl nucleotides. In yet further embodiments, the driver-target complexes are treated with a polymerase enzyme prior to the immobilizing, wherein the polymerase enzyme synthesizes a nascent strand by extending the duplex region, and the nascent strand so synthesized can optionally comprise modified nucleotides that can be selectively immobilized, e.g., biotinylated nucleotides that can be bound to avidin or streptavidin during the immobilizing step. Preferably, the nucleic acid sample is subjected to a fragmentation reaction to generate double-stranded fragments, and stem-loop adapters are added to the double-stranded fragments to generate topologically-closed, double-stranded fragments, and further the topologically-closed double-stranded fragments are denatured prior to the hybridizing.

In further aspects, methods for enriching a target region in a nucleic acid sample comprise: digesting the nucleic acid sample to generate double-stranded fragments with sticky ends; b) annealing stem-loop adapters to a subset of the double-stranded fragments, the subset comprising the target region, wherein the annealing causes displacement of a short, single-stranded terminal region of the double-stranded fragments comprising the target region; c) treating the double-stranded fragments with a single-stranded exonuclease to degrade the displaced single-stranded terminal region; d) ligating the double-stranded fragments comprising the target region to the stem-loop adapters that are annealed thereto; and e) treating the double-stranded fragments with one or more exonucleases to digest the double-stranded nucleic acid fragments that have one or no stem-loop adapter linked thereto, thus enriching for the target region in the nucleic acid sample. In some such embodiments, a first strand of the stem-loop adapters is ligated to the double-stranded fragments prior to the single-stranded exonuclease treatment, and a second strand of the stem-loop adapters is ligated to the double-stranded fragments subsequent to the single-stranded exonuclease treatment.

In various embodiments described herein, enriched nucleic acids are subjected to one or more further analyses, e.g., sequencing reactions, a haplotype analysis, diagnostic tests, screening tests, prognostic tests, barcoding, or multiplexed analyses. The target region(s) can comprise any region(s) of interest to the practitioner of the instant invention, e.g., a full-length repeat region from a genomic sample, a promoter region controlling expression of a gene of interest (which may or may not comprising a full-length repeat region), target regions from multiple chromosomes, target regions from homologous chromosomes, imprinted genes, splice isoforms, heterochromatic regions, euchromatic regions, genic regions, non-genic regions, regulatory regions, cloned nucleic acids, native nucleic acids, amplified nucleic acids, full haplotypes for a gene of interest, full alleles for a repeat expansion region, or nucleic acids from multiple sources, e.g., different genes, tissues, individual (e.g., cases and controls), barcoded nucleic acids, full-length genes and the corresponding mRNA or cDNA sequences, and the like.

BRIEF SUMMARY OF THE DRAWINGS

FIGS. 4A-4D provide a graphical representation of one embodiment of an enrichment method described herein.

DETAILED DESCRIPTION

I. General

Figure 1:
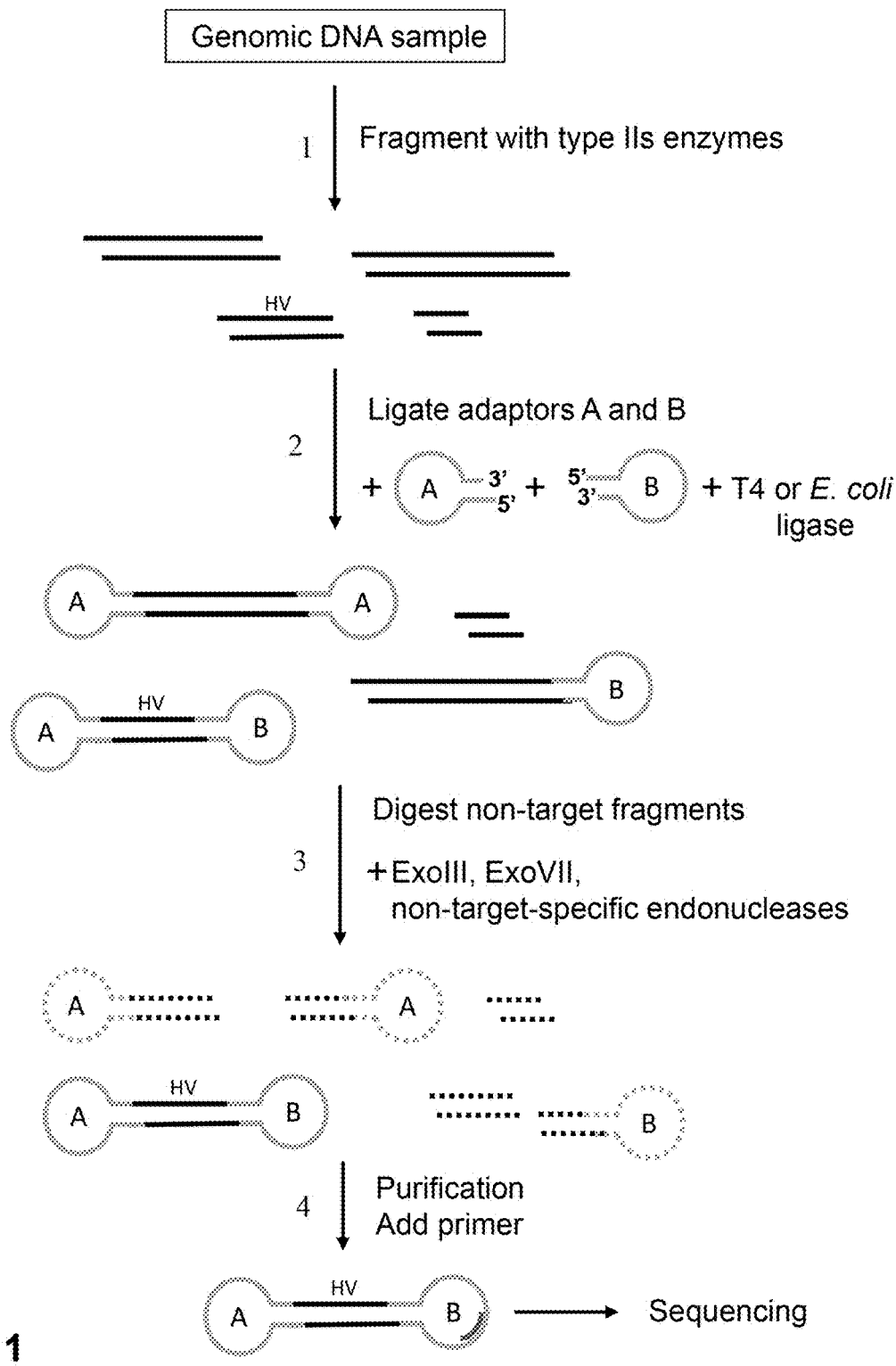
FIG. 1 provides an illustrative embodiment of a method of enriching for a target region of interest.

Unless defined otherwise, all technical and scientific terms used herein have the same meaning as commonly understood by one of ordinary skill in the art to which this invention belongs. Note that as used herein and in the appended claims, the singular forms "a," "an," and "the" include plural referents unless the context clearly dictates otherwise. Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. Although certain preferred embodiments are described in detail herein, one of ordinary skill in the art will readily recognize the applicability of the invention in other related embodiments, e.g., enrichment of target molecules other than nucleic acid molecules. Further, the enrichment methods herein can be used in combination with each other, or in combination with methods known to the ordinary practitioner, including but not limited to those described in: Huang, et al. (2008) SPIE 7269: A1-11; Mertes, et al. (2011) Briefings in Functional Genomics 10(6):374-386; Jordon, et al. (2002) Proc. Natl. Acad. Sci. USA 99(5):2942-7; Callow, et al. (2004) Nucl. Ac. Res. 32(2):e21; U.S. Patent Publication Nos. 20030059955, 20050100911, 20070003938, 20090162845, and 20100286070; U.S. Pat. No. 6,361,947; and U.S. Provisional Patent Application No. 61/799,237, filed Mar. 15, 2013, all of which are incorporated herein by reference in their entireties for all purposes.

Enriched compositions of the invention find particular utility in nucleic acid sequencing applications, especially where a region of interest is a minority species within a complex sample (e.g., genome). In such cases, the majority of sequencing data generated by sequencing the entire complex sample is not relevant to determining the sequence of the region of interest. As such, the value of the sequencing data generated is substantially increased where a majority of the complex sample is removed prior to sequencing, but where the region of interest is selectively retained. Sequencing after such an enrichment results in a higher proportion of the resulting sequence data being relevant to determining the sequence of the region of interest, since a higher percentage of the sequence reads are generated from the region of interest, e.g., by single-molecule sequencing. Many other applications will benefit from the enrichment strategies provided herein, e.g., cloning, amplification, diagnostics, prognostics, theranostics, genetic screening, and the like. In preferred embodiments, the enriched nucleic acids produced by the methods herein are used in single-molecule, real-time sequencing reaction, e.g., SMRT® Sequencing from Pacific Biosciences, Menlo Park, Calif. The use of other sequencing technologies is also contemplated, e.g., nanopore sequencing (e.g., from Oxford Nanopore), Solexa® sequencing (Illumina), tSMS™ sequencing (Helicos), Ion Torrent® sequencing (Life Technologies), pyrosequencing (e.g., from Roche/454), SOLiD® sequencing (Life Technologies), microarray sequencing (e.g., from Affymetrix), Sanger sequencing, etc. Preferably, the sequencing method is capable of sequencing long template molecules, e.g., >1000-10,000 bases or more. Preferably the sequencing method is capable of detecting base modifications during a sequencing reaction, e.g., by monitoring the kinetics of the sequencing reaction. Preferably the sequencing method can analyze the sequence of a single template molecule, e.g., in real time.

The present invention is directed to methods for analyzing nucleic acid samples and preferred compositions and methods for performing such analysis. These methods find particular utility when analyzing a small select portion ("target") of a complex sample, e.g., a single genomic region or locus, from a sample comprising the entire genome of an organism. In some aspects, a set of loci are selected to be enriched, e.g., where the set of loci are structurally or functionally related. Such target nucleic acid molecules can comprise both natural and non-natural, artificial, or non-canonical nucleotides including, but not limited to, DNA, RNA, LNA (locked nucleic acid), PNA (peptide nucleic acid), morpholino nucleic acid, glycol nucleic acid, threose nucleic acid, and mimetics and combinations thereof. The starting population of nucleic acids can be from any source, e.g., a whole genome, a collection of chromosomes, a single chromosome, or one or more regions from one or more chromosomes. It can be derived from cloned DNA (e.g., BACs, YACs, PACs, etc.), cDNA, or amplified DNA (by PCR, whole genome amplification, e.g., using Phi29 polymerase). Genomic nucleic acids can be collected from various sources; however, a genomic DNA sample is preferably isolated from RNA (by RNaseA+T1-treatment) and ssDNA. The enrichment of "native" nucleic acid targets, for sequence determination and base modification detection using single-molecule sequencing techniques (e.g., SMRT sequencing, nanopore sequencing, etc.), often requires ≥10 micrograms of human gDNA, which only has about 2-6 picograms of the targeted DNA fragment. For those samples when only a limited quantity of gDNA (sub-microgram) are available and base modification detection is not needed, a few nanograms of gDNA can be amplified using whole-genome linear amplification using a commercial kit (e.g., from Qiagen) to generate 20-50 μg of amplified nucleic acids, which can then be used in the targeted enrichment methods provided herein. However, since any base modifications are not preserved in the amplified nucleic acid, the enriched templates derived from amplified DNA cannot be used for kinetic-based base modification detection by SMRT sequencing, although other known methods for detection methylated bases can be used with such amplification, e.g., bisulfite sequencing, TAB-seq, and oxBS-Seq methods.

In certain aspects, the methods enrich complex nucleic acid samples for target nucleic acid molecules of interest. In certain embodiments, rather than attempting to remove the portion of interest from the complex sample, e.g., by using affinity tags linked to probes, the methods herein take a different approach and remove some or all of the unselected or undesired part of the sample from the portion of interest ("target"). This approach effectively reduces the complexity of the sample and enriches the sample for the portion of interest without requiring any complex affinity selection schemes. In certain embodiments, an enrichment comprises cleavage and/or degradation of non-target nucleic acids in the sample while the target nucleic acids are protected from degradation. In preferred embodiments, at least a 10-fold, 25-fold, 100-fold, 200-fold, 300-fold, 500-fold, 700-fold, 1000-fold, 10,000-fold, 20,000-fold, 50,000-fold, 100,000-fold, 200,000-fold, or greater molar enrichment of the target sequence of interest is achieved relative to the concentration of the target sequence in the original sample. In some embodiments, only fewer than 500, 400, 300, 200, 100, 50, or 20 loci are present or represented in a final, enriched mixture where the original, non-enriched mixture comprised greater than 1000, 10,000, 100,000, or 1,000,000 fragments of a complex nucleic acid sample, which potentially comprises thousands, millions, or more different loci.

The starting population of nucleic acids can be from any source, e.g., a whole genome, a collection of chromosomes, a single chromosome, or one or more regions from one or more chromosomes. It can be derived from cloned DNA (e.g., BACs, YACs, PACs, etc.), RNA (e.g., mRNA, tRNA, rRNA, ribozymes, etc.), cDNA, or a combination thereof. The starting population of nucleic acids is either native nucleic acids, e.g., genomic DNA, or amplified nucleic acids, such as those generated by PCR or whole genome amplification (WGA), e.g., using the Phi29 polymerase rolling circle method. The sample can be a metagenomic sample, e.g., an environmental or intestinal sample. Genomic nucleic acids can be collected from various sources including, but not limited to, whole blood, semen, saliva, tears, urine, fecal material, sweat, buccal cells, skin, and hair. The nucleic acids can be obtained from the same individual, which can be a human or other species (e.g., plant, bacteria, fungi, algae, archaea, etc.), or from different individuals of the same species, or different individuals of different species. Methods for generating a nucleic acid sample, e.g., from one of the sources listed above, is known and routine to those of ordinary skill in the art. Typically it involves cell lysis, stabilization and protection of the nucleic acids (e.g., from nuclease digestion), isolation of the nucleic acids from other components (e.g., proteins, carbohydrates, lipids, etc.) of the original sample, and optional fragmentation, e.g., by chemical, enzymatic, or mechanical means. The fragmentation can involve multiple strategies (e.g., staged or simultaneous fragmentation using multiple different strategies, enzymes, etc.) serves to reduce the size of the nucleic acids, which can facilitate subsequent analyses, e.g., by providing the nucleic acids with or modifiable to have termini appropriate for subsequent steps in the analysis, e.g., cloning, ligation of adapters, circularization, and the like. For example, the fragmentation can comprise a restriction enzyme digestion followed by a treatment to provide ends of a specific conformation, e.g., blunt, 3'-overhangs, or 5'-overhangs. In preferred embodiments, the overhangs are known and amenable to ligation to adapter sequences, e.g., stem-loop or hairpin adapters. Such adapters can be pre-treated to protect them from exonuclease degradation. For example, the presence of thiophosphates at the 5'-termini will prevent exonuclease degradation by a 5' to 3' exonuclease, such as T7 or lambda exonuclease. In some specific embodiments, the fragments can be treated to create long single-stranded overhangs, e.g., 10-50 bases in length. Further, where the overhang is longer than a complementary overhang of an adapter, the molecule can be subsequently treated to close any gaps remaining, e.g, by treatment with polymerase and ligase enzymes. In some embodiments, a size selection is performed to select a set of fragments that are of approximately the same size as the fragments comprising a target region. Size selection can be performed using standard methods, e.g., gel purification, density gradient separation, spin-column purification, chromatography, etc. In preferred embodiments, the amount of sample nucleic acid required for the methods provided herein is less than 10 micrograms, preferably less than one microgram, more preferably between 1-100 ng. Certain embodiments require only 50 ng or less of a sample nucleic acid for enrichment of a target of interest.

In certain aspects, a sample set of nucleic acids comprising target and non-target nucleic acids is subjected to a treatment prior to enriching for the target nucleic acids. In certain embodiments, the treatment serves to facilitate the subsequent enrichment. For example, adapters can be added to some or all nucleic acids in the sample set prior to enriching for the target nucleic acids. In some embodiments, a single adapter sequence is used to select only fragments having on overhang complementary to an overhang of the adapter at both ends. In other embodiments, two adapter sequences are used to select fragments having complements to the adapter overhangs at both ends. In especially preferred embodiments, adapter sequences are designed such that a first adapter will hybridize to a first end of a fragment of interest (target fragment) and a second adapter will hybridize to a second end of the target fragment. Subsequent treatment, e.g., with nucleases blocked by the adapters, is optionally performed to degrade fragments that do not have adapters linked to both ends.

In certain preferred embodiments, a sample set of nucleic acids is not amplified or cloned prior to enrichment and/or further analysis, e.g., sequence analysis. For certain applications, e.g., where epigenetic modifications are being analyzed (e.g., 5-mC, 6-mA, etc.), amplification generates amplicons that lack the modification that was present in the original sample set, e.g., where a modified base has the same binding specificity to a complementary nucleotide as does an unmodified base. For example, C, 5-MeC, and 5-hmC are all complementary to G. As such, amplification of a template nucleic acid having one of these modifications using unmodified nucleoside polyphosphates will generate amplicons lacking the modification found in the original template. Further, as noted above, amplification can introduce variations in the amplicons (e.g., via errors during PCR) such that their nucleotide sequence is not reflective of the original sample. As such, in preferred embodiments, nucleic acids to be enriched and/or otherwise analyzed are typically not amplified in the methods herein. Similarly, cloning of a target region into another organism often does not maintain modifications present in the original sample nucleic acid, so in preferred embodiments nucleic acids to be enriched and/or otherwise analyzed are typically not cloned in the methods herein. Rather, they are enriched directly from the original nucleic acid sample.

Many of the methods herein involve sequence-specific ligation of one nucleic acid (e.g., sample nucleic acid fragment) to another nucleic acid (e.g., adapter sequence). Ligation reactions can have a high level of fidelity measured by the ratio of the ligation rate between a correctly matched end overlap versus an incorrectly matched end due to complementarity between overhanging sequences. However, like most biochemical reactions, if given a sufficient amount of time the reaction will go to completion even when the conditions do not favor or nominally allow it. For example: ligating a 4-base overhang with 5'-ACAG-3' against another 4-base overhand 3'-TGAC-5' may proceed 10,000 times faster than against 3'-TGAG-5'. However, because ligation reactions are generally allowed to run to completion, if there is no alternative complementary sequence for the TGAG overhang it will eventually ligate to the 5'-ACAG-3' site even though the overhang sequences are mismatched. The result is an apparent very low level of fidelity based on the end-point with the reaction having gone to completion, even though the underlying biochemistry has very high fidelity and strongly favored the correct match.

A solution to this problem is to deliberately add competitor sequences that will ligate to off-target sites, thus making them unavailable for annealing to the adapter sequences designed to anneal preferentially to the target sites, thereby favoring ligation between these adapter sequences and the target sites. These competitors can be thought of as "antiligators" or "Alligators." In preferred embodiments, the off-target ligation event is different from the target ligation events in further ways that enhance the enrichment of the target nucleic acids. For example, in various methods described herein, ExoIII and ExoVII are used to digest fragments having free 3' or 5' ends. If the alligator-ligation product is a molecule having free ends but an on-target ligation product does not, then the exonuclease digestion eliminates the Alligator-ligation product but not interfere with the on-target ligation products. Another strategy for distinguishing the Alligator-ligation products from the on-target ligation products is to include a specific binding site in the Alligator-ligation product. For example, a biotin-derivatized base or a poly A or poly T tail in the Alligator competitors that ligate to the off-target fragments can be used as a hybridization binding site. Another approach is to make the adapters used in the on-target ligation reaction have a specific binding site that the Alligator competitors lack. Since only target fragments will be ligated to the on-target adapters, only they will be captured. The challenge in this strategy is where it is desired that the target fragment have adapters on both ends, because molecules that only ligate at one end, and therefore have only one adapter (with the binding site), will also be captured. In these cases, treatments can be performed to remove or degrade any captured molecules that have only one adapter. For example, the on-target adapters can have a stem-loop structure or modified bases or bulky groups that prevent degradation by exonuclease enzymes. Those that have only one adapter have only one end protected from degradation. The other end is therefore susceptible to exonuclease degradation, and this susceptibility can be used to remove these "half-ligated" target fragments from the mixture, thereby further enriching for the "fully-ligated" target fragments.

There are many different ways to create a population of Alligator molecules. In some embodiments, degenerate oligonucleotide synthesis is used to generate a diverse set of such molecules. Preferably, no Alligator molecule has a sequence that will efficiently ligate with the target nucleic acids, e.g., no Alligator molecule has a cohesive end comprising an overhang that is complementary to an end of a target fragments. In certain preferred embodiments, the population of Alligator molecules does not comprise any molecules that efficiently ligate to the target nucleic acids. For example, several pools of synthetic oligonucleotides can be generated. One such pool includes the following oligonucleotides: [ACG]NNN, N[ACT]NN, NN[CGT]N, and NNN[ACT] (using REGEX notation); or VNNN, NHNN, NNBN, and NNNH (using DNA ambiguity letter codes). This set of Alligator oligonucleotides includes ever possible 4-base oligonucleotide except for TGAG. It is more complicated to make a mixture that includes everything but two specific sequences, which requires more reactions, but can still be done with significantly fewer than all 255 combinations reflected. For example, a pool with everything except TGAT and GTCA can be made having the following: MNNN, NMNN, NNKN, and NNNS. This oligonucleotide set will include most of the combinations but will omit sequences like TTCA. The few missing sequences can be made in single reactions, or they can be grouped so that some degenerate bases can be used to cover more than one sequence in a single reaction.

Another method of eliminating unwanted Alligator oligos is to ligate them against a stoichimetrically limited population of on-target sequences. For example, if a pool of wholly degenerate oligonucleotides (NNNN) is made and there is a total of 256 nmol of oligo, then there is 1 nm (on average) of each individual type in the pool. If 3 nmol of a complement to TGAT and 3 nmol of complement to GTCA is added and ligated, the reaction will go to completion taking essentially all (99.99% of the TGAT and GTCA) as well as 4 nmols of other material with it. This will leave behind about 250 nmol of Alligator material that has been depleted for the two that are desired. This method can be varied according to the amount of "sorbent" sequence to use to adjust the stringency of the resulting mixture. In this method, some means of removing the sorbents is useful, for example biotinylated tags or poly T strands so that magnetic bead purification with streptavidin or polyA tails could be used to pull out the sorbents.

In other embodiments, the fact a few of the that NNNN will contain Alligators that will ligate to on-target materials is ignored. As long as the fraction of correct adapter to "on-target Alligator" is low, the total loss of yield will also be low. With 10,000 theoretical stringency there is some room to throw away a small amount of yield while still keeping the Alligator effect intact. There are many possible structures for the Alligator oligonucleotides. They can be single-stranded DNA just long enough to cover the overhang sequence. For example, a 4-base overhang is commonly generated by cleavage with type IIs restriction enzymes. In this case the Alligator sequence could be just NNNN, as above. Alternatively, it can be a duplex containing the degenerate bases plus a defined sequence at the ends to provide a better footprint for the ligase enzyme during the ligation reaction. As described above, the use of Alligator sequences in ligation reactions increases the specificity of ligation reactions used to target specific regions of interest in a nucleic acid sample.

In other aspects, subsequent analysis of enriched nucleic acids comprises sequencing using non-ligation-dependent methods of adding a binding site for a primer. For example, an enriched target molecule can be subjected to a terminal transferase reaction in the presence of A nucleotides to provide a long, 3'-terminal, polyA sequence at each end. In some embodiments, a polyT primer is bound to the polyA tail, and polymerase-mediated primer extension is performed. The primer extension can be for amplifying the sequence, or more preferably, is during a single-molecule sequencing-by-synthesis reaction. Alternatively or in addition, the polyA tail can be used as a binding partner for enrichment, e.g., by providing a polyT sequence on a surface (e.g., a magnetic bead). The polyA tailed molecules can be immobilized on the polyT-comprising surface for various purposes. In certain preferred embodiments, the polyA tail is used for both primer binding and immobilization to a bead or other surface. Specific uses for bead-bound sequencing templates are described at length in U.S. Patent Publication No. 20120322666, which is incorporated herein by reference in its entirety for all purposes.

II. Methods Utilizing Nuclease Degradation of Non-Target Nucleic Acids

As described briefly above, certain preferred embodiments of the methods provided herein enrich target nucleic acids, at least in part, by implementing the degradation of non-target nucleic acids. Such degradation is typically followed by a purification step to remove the products of the degradation, e.g., small fragments or free nucleotides, while retaining the target nucleic acids. The final pool need not be entirely free of non-target nucleic acids, but will be significantly enriched for the target nucleic acids.

In preferred embodiments, target nucleic acids are protected by adapters that are resistant to degradation by the nucleases to be used to remove non-target nucleic acids. Such adapters can be single-stranded or double-stranded, or may comprise both single- and double-stranded portions. (Methods for linking single-stranded or double-stranded oligonucleotides to the ends of nucleic acid fragments are well known to those of skill in the art.) Adapters that are resistant to endonuclease degradation don't contain recognition sequences for restriction endonuclease(s) used to cleave non-target nucleic acids. Adapters that are resistant to exonuclease degradation may comprise blocking groups at the single-stranded or double-stranded termini that are not susceptible to the exonuclease(s) used. In certain preferred embodiments, stem-loop (a.k.a. "hairpin") adapters are used. These adapters are single-stranded, but their termini are complementary such that the adapter folds back on itself to generate a double-stranded portion and a single-stranded loop. A stem-loop adapter can be linked to an end of a linear, double-stranded nucleic acid to protect the end from exonuclease degradation by removing the availability of the previously terminal nucleotides to the exonuclease. For example, where stem-loop adapters are joined to the ends of a double-stranded nucleic acid fragment, such that there are no terminal nucleotides (e.g., any gaps have been filled and ligated), the resulting molecule lacks terminal nucleotides, instead bearing a single-stranded loop at each end. The length of the original double-stranded nucleic acid to which the adapters are added can vary, but is preferably at least 200, 500, 1000, 3000, 5000, 7000, 10,000, 15,000, or 20,000 base pairs in length. The length of the insert depends primarily on the intended use, and in some embodiments is based upon the length of a region that is equal to or greater than the average read length in a sequencing technique to be used. In other embodiments, such as for redundant sequencing applications, the length of the insert is much smaller than the average read length to allow repeated sequencing of the molecule, e.g., in a "rolling-circle" manner, by a single polymerase enzyme.

In certain preferred embodiments, the adapters can have primer sequences pre-hybridized to them prior to ligation, e.g., where the fragments are to be subjected to a primer extension reaction (e.g., PCR, sequence-by-synthesis reaction, etc. However, such primers must be configured to survive any treatments performed on the nucleic acid sample prior to the primer extension reaction. For example, where a nuclease treatment will be performed the primer must be resistant to degradation, but still able to be extended, e.g., in a polymerization reaction. In alternative preferred embodiments, primer is not present on the adapter during the ligation reaction, but is added later, e.g., prior to the primer extension reaction. Methods for producing such double-stem-loop nucleic acid molecules are provided, e.g., in U.S. Pat. No. 8,153,375, which is incorporated herein by reference in its entirety for all purposes. For ease of discussion, most embodiments herein refer to stem-loop adapters to protect the ends of a target fragment, but it will be understood that stem-loop adapters are but one example of adapters that can be used in the methods herein.

One or both adapters can have primer binding sites, and during a subsequent primer-extension reaction primers on one or both adapters may be extended. In preferred embodiments only one primer is extended even in cases where two are present. In some preferred embodiments, a primer is complementary to and binds within the "loop" portion of a stem-loop adapter. However, in other embodiments, primers have a 3' end that is complementary to a 5' end of a strand of the target region, and so hybridize to the 5' end of a strand of the target region, and optionally also hybridize to at least a portion of the adapter ligated thereto. In some such embodiments, after stem-loop ligation and, preferably, after any nuclease degradation of non-target strands, the remaining fragments having stem-loop adapters at both ends are treated to denature the double-stranded target fragment. This treatment results in a single-stranded circle comprising both strands of the double-stranded fragment separated by the adapter sequences: . . . adapter 1-target strand 1-adapter 2-target strand 2 . . . , where each target strand is flanked by the two adapter sequences in a circular configuration. Denaturation of the target region renders the 5' end that is complementary to the primer available for primer binding. Since the primer will serve as an initiation point for extension if the 3' end is annealed to the target fragment, this provides a further selection for the target fragment. That is, even if some of the non-target fragments are ligated to adapters at both ends, it is extremely unlikely that they will also have a 5' end that is identical to that of the target fragment. As such, they will not support extension of the primer, even though the primer may anneal at its 5' end to the adapter sequence. As a result, where the sequencing of these fragments requires primer-extension, no sequence data will be generated from the non-target fragments.

Yet further, primers can comprise modified bases that enhance hybridization to the adapters and/or target fragments. For example, such modified bases can allow a primer to bind to a double-stranded sequence even without prior denaturation, e.g., by strand invasion. This can be accomplished where a primer binds more strongly than the complementary strand of the target fragment, for example, where it comprises modified nucleotides such as PNA (peptide nucleic acid) nucleotides, LNA (locked nucleic acid) nucleotides, O-methyl-modified nucleotides, and other modified nucleotides known in the art that have a greater affinity to a complementary base than does a canonical nucleotide. In further embodiments, known recombination enzymes can also be present to facilitate strand invasion, e.g., *E. coli* RecA and RecT proteins, yeast Rad 51 and Rad52 proteins, human splicing factor PSF, protein 3 from phage lambda, and other enzymes including helicases and single-stranded DNA binding proteins. Strand invasion can be further facilitated by addition of other protein factors, e.g., single-strand binding proteins such as *E. coli* SSB protein. Primers that are to be annealed prior to a nuclease degradation step are preferably resistant to the digestion, e.g. due to having a blocking group on any susceptible termini, or by using nucleases that do not cleave at a double-stranded/single-stranded junction. Where one or more endonucleases are used for the digestion, the annealing of the primer preferably does not create a recognition site for the endonuclease(s).

In certain aspects, a target region of interest is examined to identify restriction enzyme recognition sequences that flank the region. Alternatively, this information can be attained from a database comprising sequence information for the region of interest, e.g., by virtue of a known or previously sequenced reference sequence. Preferably, the region between the two restriction sites is from about 100 bp to about 10 kb, and even longer stretches are found between rare-cutting restriction enzymes. For example, NotI is a rare cutter with an eight-base recognition site, which will occur on average about once every 65,000 base pairs in a genome (assuming an average frequency of each type of canonical base of ¼). Other rare-cutting enzymes are known in the art and commercially available, including AbsI, AscI, BbvCI, CciNI, FseI, MreI, PalAI, RigI, SdaI, and SgsI. A software program, similar to the NEBCutter Version 2.0 from New England Biolabs, can optionally be used to find all the restriction enzyme cut sites within and flanking a target region. Choose a single restriction enzyme or a combination of restriction enzymes that can digest in the flanking regions close to the boundary of the target region. For digestion of native DNA, avoid using restriction enzyme s that are sensitive to modified base(s) (methylated CpG for mammalian DNA) at the restriction enzyme recognition sequence and the cutting sites; especially at both sites of the targeted fragment. The targeted DNA fragment will not be enriched if the chosen restriction enzyme(s) cannot digest efficiently at both sites of the fragment.

Subsequent cleavage of a nucleic acid sample comprising the target region will produce a pool of fragments, including the one with the target region. Addition of adapters having overhangs complementary to an overhang produced by the endonuclease in the presence of a ligase (e.g., T4 or *E. coli* ligase) will produce fragments having adapters linked at the ends that were cleaved by the endonuclease. The adapters can be present during the initial cleavage reaction, or can be subsequently added to the reaction mixture. Those fragments having cleavage sites at both ends that comprise overhangs complementary to the adapters, including the fragment containing the region of interest, will have an adapter at both ends. Where active restriction enzymes are present (preferably, in excess) during the ligase reaction, any non-adapter ligation events will be reversed, e.g., where two fragments anneal with one another rather than with adapters. Subsequent purification will remove the enzymes, excess adapters, and adapter-dimers formed during the reaction. Size-selection methods are especially preferred, e.g., Agilent® AMPure® bead kits (Beckman Coulter, Brea, Calif.). Optionally, the sample can also be subjected to commercially available size-selection strategies to isolate fragments having a size consistent with the known size of the fragment comprising the region of interest ("target fragment"). Such methods include, but are not limited to, bead-, gel-, chromatography-, and density-based methods, e.g., AMPure® bead-based methods. To select for only those fragments having an adapter on both ends, an exonuclease(s) (e.g., ExoIII and ExoVII is a preferred combination) can be added after the ligation reaction to degrade any nucleic acids that have a free terminal nucleotide. To further enrich for the target region, additional endonuclease(s) that do not cleave the fragment comprising the target region (or the adapter sequences) can be added during the original fragmentation, during the ligation reaction, or after the ligation reaction. If added during the original fragmentation or ligation reaction, the overhang left by the additional endonucleases must be distinct from that left by the nuclease whose recognition sequence flanks the target region. This will prevent ligation of the adapters to the overhangs created by the additional endonucleases. If they are added after the ligation reaction and subsequent removal of the adapters and ligase enzyme, the overhangs could be complementary to the adapters. In either case, additional terminal nucleotides will be exposed that are susceptible to exonuclease degradation, further allowing the removal of non-target nucleic acid fragments comprising only one or no adapter ligated from the pool of fragments. As will be apparent to those of skill in the art, in any of these reactions comprising multiple different enzymes acting simultaneously, the reaction conditions must support the activity of all enzyme present. As such, care must be taken when choosing various nucleases and ligases to ensure their reaction conditions are compatible. Where selected enzymes are not compatible, a staged approach can be implemented in which reaction conditions are adjusted to accommodate different stages in the reaction.

In certain preferred embodiments, two different endonucleases are chosen that flank the region of interest in the nucleic acid sample. Preferably, the region between the two restriction sites is from about 100 bp to about 10 kb, and can in some embodiments be even longer, depending on the frequency of the cleavage sites (e.g., greater than 10, 20, 30, 40, or 50 kb). The ability to enrich for very long regions is important because it allows haplotypes for whole genes, repeat regions, regulatory regions, etc. to be maintained in the enriched nucleic acid that will be subsequently analyzed. Further, the long regions can span genomic regions that are otherwise difficult to analyze, e.g., because of a highly repetitive or low-complexity (e.g., GC- or AT-rich) nature. Cleavage of the sample with two different endonucleases will produce a first subset of fragments having a cleavage site at only one end, a second subset of fragments having the same cleavage site at both ends, and a third subset of fragments having a different cleavage site at each end. The third subset of fragments comprises the fragment containing the target region ("target fragment"), as well as other non-target fragments; adapter-dimers (and excess adapters & enzymes) are removed by subsequent purification (e.g., using AMPure® beads) This strategy allows ligation of different adapters at each end of the target fragment. Subsequent exonuclease degradation will degrade all fragments that are not flanked by two adapters, whether they are the same adapter or different adapters at each end. As above, additional endonucleases can also be used to further degrade non-target fragments including some that have two adapters ligated, and this can provide additional termini that are not ligatable to the adapters and therefore are susceptible to the exonuclease degradation. As noted above, a size-selection strategy can optionally be used to further isolate fragments matching the expected size of the target fragment.

In some embodiments, different targets can be selected by dividing a nucleic acid sample into aliquots and subjecting the different aliquots to digestion with different combinations of endonucleases and ligation with compatible adapters, depending on the restriction sites flanking and internal to the different target regions of interest in each aliquot. Optionally, the aliquots can be recombined prior to further analysis, e.g., sequencing-by-synthesis. For example, they can be recombined after the adapters, ligase, and endonuclease enzymes are removed from each aliquot, whether before or after exonuclease digestion.

Although various kinds of restriction endonucleases can be used in the methods herein, further enrichment can be realized by using type IIs restriction enzymes. These enzymes cut at a site that is not within the recognition sequence, so can provide overhangs that are random. Typically, cleavage by type IIs restriction enzymes generates a three to four base overhang having a random sequence. Some preferred type IIs restriction enzymes generate longer random overhangs of five bases or more (e.g., HgaI), which provides an even more stringent selection since a random "five-mer" will occur less frequently on average than a shorter random sequence, and the complementary adapter will therefore be ligated to fewer non-target fragments. Preferred methods use type IIs restriction enzymes that recognize a specific sequence of five or more bases, and that generate nucleic acid fragments having overhangs of three or more bases outside of the recognition sequence. Where the sequence around a target region is known, the overhangs generated by a type IIs restriction enzyme is also known. This knowledge allows the design of adapters specific for the overhangs generated around the target region. Table I provides some examples of type IIs restriction enzymes, including their recognition sequence, cut site, overhang produced, and the average fragment size based on the estimated frequency of the recognition sequence. Others are known in the art, including but not limited to BsaI, BfuAI, FokI, BaeI, and AcuI.

TABLE I

Exemplary Type IIs Restriction Enzymes

| RE | Sequence | Cut site | Overhang | Av. Frag Size (bp) |
|---|---|---|---|---|
| Bsm AI | GTCTC | G T C T C N/N N N N (SEQ ID NO: 1)<br>C A G A G N N N N N/ (SEQ ID NO: 2) | 5' - NNNN | 1024 |
| Sfa NI | GCATC | G C A T C N N N N N/N N N N (SEQ ID NO: 3)<br>C G T A G N N N N N N N N N/ (SEQ ID NO: 4) | 5' - NNNN | 1024 |
| Bsa I | GGTCTC | G G T C T C N/N N N N (SEQ ID NO: 5)<br>C C A G A G N N N N N/ (SEQ ID NO: 6) | 5' - NNNN | 4096 |
| Bsm BI | CGTCTC | C G T C T C N/N N N N (SEQ ID NO: 7)<br>G C A G A G N N N N N/ (SEQ ID NO: 8) | 5' - NNNN | 4096 |
| Bsp MI | ACCTGC | A C C T G C N N N N/N N N N (SEQ ID NO: 9)<br>T G G A C C N N N N N N N N/ (SEQ ID NO: 10) | 5' - NNNN | 4096 |
| Sap I | GCTCTTC | G C T C T T C N/N N N (SEQ ID NO: 11)<br>C G A G A A G N N N N/ (SEQ ID NO: 12) | 5' - NNN | 16384 |
| Hga I | GACGC | G A C G C N N N N N/N N N N N (SEQ ID NO: 13)<br>C T G C G N N N N N N N N N N/ (SEQ ID NO: 14) | 5' - NNNNN | 1024 |

Since the type IIs restriction enzymes create random overhangs, any particular overhang sequence is only created at a small portion of the total cut sites. Where the overhangs flanking the region of interest are known, adapters can be used that will ensure the target fragment is capped by adapters at both ends, and therefore protected from exonuclease treatment. Since not all cut sites will be linked to adapters, e.g., those that do not create overhangs complementary to the adapters, there is an additional enrichment for the target fragment. The number of fragments having both termini capped with adapters is much fewer than the number of fragments having none or only one adapter ligated at an end.

In preferred embodiments, a first adapter is complementary to a type IIs cut site upstream of a target region, and a second adapter is complementary to a type IIs cut site downstream of the target region. Given the randomness of the overhang generated by the type IIs restriction enzymes, these flanking cut sites may be created by the same or different type IIs enzymes, depending on the nucleotide sequence of the sample nucleic acid and the availability of the enzymes, e.g., from New England Biolabs and other commercial vendors. Ligation of the adapters to a nucleic acid sample digested with the chosen type IIs restriction enzyme(s) results in a set of molecules having none, one, or two adapters ligated thereto. Some of the molecules ligated to the first adapter at one end and the second adapter at the other end comprise the target region. If the frequency of the complementary overhangs in the sample fragments is very low, there may be very few fragments with both adapters linked thereto. Preferably, the adapters render the ends of the fragments resistant to exonuclease degradation, either by the inclusion of blocking groups or by a lack of terminal nucleotides, e.g., as in stem-loop or hairpin adapters. Optionally, additional restriction enzymes can be used that have recognition sequences that are absent from the region of interest, but that occur in other parts of the genome. Preferably, these restriction enzymes have defined overhangs that are not complementary to the adapters. These additional restriction enzymes would serve to further reduce the size of the non-target fragments. Subsequent exonuclease treatment degrades all fragments with a free terminus leaving only those that have two stem-loop adapters, one on each end.

This type IIs restriction digestion and adapter ligation method provides a powerful way to enrich for fragments of interest in a complex nucleic acid sample, e.g., a genomic nucleic acid sample. For example, if a human genome is subjected to digestion with Sfa NI and subsequently annealed to one adapter having a specific four-base overhang, ~2.9 million fragments (~1 kb average fragment size) will be generated and ~11,400×(2 ends per fragment)=~22, 800 of them will be annealed to the adapter, at least at one end. If a second adapter having a specific four-base overhang is also used, the number of fragments that will have hybridized to the two different adapters (one at each end) is expected to be only about 50×(2 ends per fragment)=100. Similarly, for the same human genomic sample, digestion with Bsa I results in ~732,400 fragments (~4 kb average size), ~2860×(2 ends per fragment)=~5720 of which will hybridize to a single adapter having a specific four-base overhang, and ~12×(2 ends per fragment)=~24 of which will hybridize to two adapters having specific and different four-base overhangs (one at each end). Yet further, Sap I digestion of a human genomic sample provides approximately 183,100 fragments of about 16 kb average size; a single adapter having a specific three-base overhang will hybridize to ~2860×(2 ends per fragment)=~5720 fragments, and two adapters having different specific three-base overhangs will hybridize to ~45×(2 ends per fragments)=~90 fragments. This huge reduction in sample complexity is extremely useful for analyzing a specific region of interest in a large, complex, nucleic acid sample.

FIG. 1 illustrates an exemplary preferred embodiment of the invention. A prophetic genomic DNA sample comprises a gene having a hypervariable region, and a researcher needs to determine the nucleotide sequence of the hypervariable region. Single-molecule sequencing is chosen to determine the nucleotide sequences of individual molecules of this target region so that sequence variations can be determined for each molecule. In a first step, the genomic DNA sample is fragmented (1) by restriction enzyme digestion using a type IIs restriction enzyme having recognition sequences that flank a target region (labeled HV) within a gene of interest to leave cut sites having random four-base overhangs. Adapters (labeled A and B) having overhangs complementary to the two cut sites generated by the restriction enzymes that flank the target region are ligated to the fragments produced in the cleavage reaction using a T4 or *E. coli* ligase enzyme (2). The fragments comprising the HV target region ("target fragments") will comprise a different adapter on each end. Some non-target fragments will also be flanked by two adapters, some will have only one adapter, and some will not be ligated to any adapter. Since the ligase and endonucleases both function efficiently in the same reaction buffer, the reactions 1 and 2 can be performed simultaneously.

After the ligation reaction has proceeded long enough to reasonably expect that all compatible overhangs have been linked to complementary adapters, two exonucleases (ExoIII and ExoVII) and a set of endonucleases are added to the reaction mixture (3). The endonucleases are chosen to not have recognition sequences within the target fragment or the adapters, but do cleave some of the non-target fragments in the mixture. The exonucleases degrade those fragments cleaved by the endonucleases, as well as any other fragments that have terminal nucleotides not protected by an adapter. After the final digest with the exonucleases and endonucleases, the reaction mixture is subjected to an AMPure bead-based purification process to remove free adapters, adapter-dimers, enzymes, and the nucleic acid products of the final digest, e.g., free nucleotides and small nucleic acid fragments (4). The nucleic acid fragments having adapters at both ends are recovered after the purification and subjected to a single-molecule sequencing reaction.

Optionally, additional enrichment can be performed after exonuclease degradation of non-target fragments that have a free terminus. For example, in some embodiments, the resulting adapter-protected constructs are subjected to further type IIs endonuclease digestion to provide specific known overhanging sequences that flank a target region internal to the first type IIs cut sites. The additional endonuclease digestion provides a second round of ligation to a different set of specific overhang sequences using a new set of hairpin adapters, e.g., prior to exonuclease treatment. Any constructs that do not reveal overhanging sequences complementary at both ends to the new set of adapters will retain terminal nucleotides susceptible to exonuclease degradation after the ligation step. This additional cleavage/ligation/digestion process is essentially a repeat of the first iteration, but provides an additional enrichment because it requires two additional regions of known sequence flanking the target region. This additional round of enrichment is beneficial where the first cleavage/ligation/digestion process captured a larger proportion of non-target sequences than is desirable. This can occur, for example, when the type IIs cleavage sites that flank the target region produce only a small overhang since other cleavage sites that are not near the target region are more likely to have the same overhang than if the overhang sequence were longer.

In related embodiments, a type II restriction enzyme is used to fragment a nucleic acid sample to generate a mixture of fragments, some of which have a target nucleic acid region for which enrichment is sought. The type II restriction enzyme chosen for the fragmentation provides fragments having 5'-ends that are susceptible to single-strand exonuclease activity, such that exposure to a 5'-3' exonuclease (e.g., T7 or lambda exonuclease) results in 3' overhangs on the fragments. Stem-loop adapters, as described elsewhere herein, added to or already present in the mixture have 3' overhangs that are complementary to the 3' overhangs flanking the fragments comprising the target nucleic acid region. Once bound, these adapters serve as priming sites for a polymerase enzyme, which extends the adapters into the fragment until the gaps between the 3'-ends of the adapters and the recessed 5'-ends of the fragment are filled with newly added nucleotides. A ligase connects the newly synthesized 3'-ends of the adapters to the recessed 5'-ends of the fragment, thereby protecting the 5'-ends from further degradation by the exonuclease. Fragments that do not receive adapters at both ends will continue to be degraded by the exonuclease. In preferred embodiments, the exonuclease has no or very weak endonuclease activity and is not highly processive, such that the polymerase can catch up with it and the ligase can connect the adapter strand to the fragment strand before the exonuclease has degraded more than 20, 30, 40, or 50 nucleotides of the 5'-terminus at each end of the fragment comprising the target region. Preferably, the polymerase used to extend the 3'-end of the adapters has no or very weak strand-displacement activity so that it does not begin to displace the 5'-end of the strand of the fragment, since this would likely inhibit ligation of the 3'-end of the adapter strand to the 5'-end of the fragment strand. In certain embodiments, the Phusion® polymerase is used for extension of the adapter 3'-overhangs. In especially preferred embodiments, the 3'-overhang of the adapters comprise at least 10, 15, 20, 25, or 30 bases that are complementary to the 3'-overhangs of the fragment comprising the target region. As such, typically two different adapters are ligated to a single fragment, one complementary to each end. Long complementary regions are preferred as they increase the specificity and stability with which the adapters bind only to the target fragment. For shorter overhangs, e.g., where only a shorter sequence is known at the ends of the fragment, tighter-binding nucleotide analogs (e.g., 2'-O-methyl nucleotides) are optionally included in the adapter overhangs to compensate for the shorter hybridized region. In specific embodiments, the reaction is carried out at a temperature that reduces secondary structure of the single-strand overhangs of the adapters and fragments, while still supporting the exonuclease, polymerase, and ligase activities. For example, a temperature of 40-60° C., more preferably 45-55° C., and even more preferably about 50° C. is appropriate in certain embodiments. In some preferred embodiments, Taq ligase is used to connect the adapter and fragment strands, since this ligase efficiently operates at such elevated temperatures. Following adapter hybridization, extension, and ligation, the mixture can be subjected to further digestion using exonuclease enzymes and, optionally, one or more endonucleases having a recognition sequence known to be absent from the target fragment. Further purification processes can be subsequently performed to remove free adapters, adapter-dimers, enzymes, and the nucleic acid products of the final digest, e.g., free nucleotides and small nucleic acid fragments. The nucleic acid fragments having adapters at both ends are recovered after the purification and subjected to further analysis, e.g., sequencing, cloning, amplification, etc. Alternatively or additionally, they can be subjected to selection using capture-hook-based methods, as described elsewhere herein.

Although the methods herein do not require amplification of the target nucleic acid, in some preferred embodiments a single-stranded circular molecule can be subjected to rolling circle amplification to generate a strand comprising multiple complementary copies of the single-stranded circle. This process increases the amount of target nucleic acid available for further analysis, which can be especially important where the amount of the original sample nucleic acid is extremely limiting. The rolling-circle mode of amplification is preferable to conventional PCR, the latter of which can introduce and perpetuate changes in the population of amplicons generated that cannot be distinguished from true variants in the original template strands. In contrast, rolling-circle replication creates multiple complementary copies of the original template, and while it is possible that changes can occur during synthesis, these changes are not perpetuated since the newly synthesized strand is not used as a template strand. As such, any random changes introduced will not be replicated in additional molecules, and true variants will be readily distinguishable. Of particular interest is the analysis of highly repetitive regions, and in particular the ability to analyze these regions as a single target nucleic acid. The methods herein can be used to enrich for a full-length repeat region, which preserves the haplotype information and allows a true measure of the number of repeats in the region, as well as any repeat interruptions therein. In some embodiments, promoter or other regulatory regions are also included in the target region, which are analyzed together in a single target nucleic acid. In such embodiments, any amplification should be performed with a polymerase enzyme that can faithfully produce a complementary strand within a repeat region. As such, a preferred polymerase for rolling-circle amplification is as Phi29 (Φ29) DNA polymerase, which has an extremely long read length and can readily process highly repetitive nucleic acid regions. Such amplification is preferably performed using the whole genomic sample, e.g., prior to any enrichment, but is optionally used at a later stage in the enrichment process, and is applicable to extremely small amounts of sample nucleic acids, e.g., 1-10 ng quantities. Although such amplification does not maintain the modification patterns present in the original template, the method can optionally be used with other methylation sequencing strategies where such information is desirable. For example, other methods such as bisulfite sequencing, TAB-seq (from Wisegene, Chicago, Ill.), and oxBS-Seq (oxidative bisulfite sequencing) depend upon PCR to amplify the treated nucleic acids prior to sequencing. The methods herein can be used to enrich for target regions that can be treated by these methylation-detection methods, but amplified using the rolling-circle amplification strategy rather than PCR, and subsequently further analyzed, e.g., subjected to a sequencing reaction.

In certain preferred embodiments, additional enrichment for a target region can be achieved through the methods described in U.S. patent application Ser. No. 13/427,725, filed Mar. 22, 2012 and incorporated herein by reference in its entirety for all purposes. The methods and compositions described therein are directed to isolating nucleic acids or polymerase-nucleic acid complexes, and utilize the ability of a polymerase having strand displacement activity to open up a double-stranded region (e.g., the "stem" of a stem-loop structure and/or a double-stranded target region) to expose a sequence within the double-stranded region, i.e., to render it single-stranded. This single-stranded sequence is targeted and captured using a "capture-hook" oligonucleotide that is complementary to the sequence. Once a polymerase begins to unwind the double-stranded portion by synthesizing a nascent strand using a first strand of the duplex, the sequence on the second strand of the duplex is rendered single-stranded, and this is the strand that is complementary to the capture-hook oligonucleotide; since it is now single-stranded, it is available for hybridization to the capture-hook molecule. This method provides a further enrichment where the capture-hook oligonucleotide is complementary to a sequence specific to the target fragment, since other non-target molecules that survived the nuclease digestion are unlikely to also comprise the target-specific sequence and so will not anneal to the capture-hook oligonucleotide. To expose enough of the target fragment to ensure adequate specificity, the polymerase may open the double-stranded region of the target fragment at least 10, 20, 30, 40, or even 50 bases, and the capture-hook oligonucleotide can be complementary to all or only a portion of the opened target region. The capture-hook molecule is typically able to be linked to a solid surface (e.g., a bead or column) to allow the target fragment to be immobilized. In certain preferred embodiments, the capture-hook oligonucleotide comprises a region complementary to an oligonucleotide bound to a bead or other surface. For example, the capture-hook oligonucleotide can comprise a polyA region that can bind to a polyT region of a magnetic-bead-bound oligonucleotide. Typically, the sequence for the surface-bound oligonucleotide is chosen to be a sequence that is not complementary to the target fragments. Only those polymerase-nucleic acid complexes hybridized to a "capture-hook" oligonucleotide are captured on the magnetic beads, and the non-target fragments can then be removed by standard methods, e.g. washing. The target fragments are subsequently removed from the capture-hook oligos and subjected to further analysis, e.g., sequence analysis.

In some cases, non-target fragments have sequence complementary to a surface-bound oligonucleotide to which a capture-hook oligonucleotide hybridizes. For example, non-target fragments from homopolymer regions of a genome can bind a poly-dT oligo on a magnetic bead and be purified along with (or instead of) target fragments bound to the capture-hook oligonucleotides having a polyA-region. To prevent this, following polymerase-mediated separation of the fragments, the mixture is exposed to the substrate-bound oligonucleotide in the absence of the capture-hook oligonucleotides to capture any molecules that are complementary thereto, which can then be removed. After removal of these non-specific complexes, the capture-hook oligonucleotides specific for the opened target fragments are added. Newly added substrate-bound oligonucleotides are used to purify the capture-hook oligonucleotides hybridized to the target fragments without interference of non-target fragments complementary to the substrate-bound oligonucleotides. Methods involving the pre-addition of the substrate-bound oligonucleotides generally require that these oligonucleotides not be complementary to the opened target fragments; otherwise, these target fragments would also be removed along with the non-target fragments.

Figure 10B:
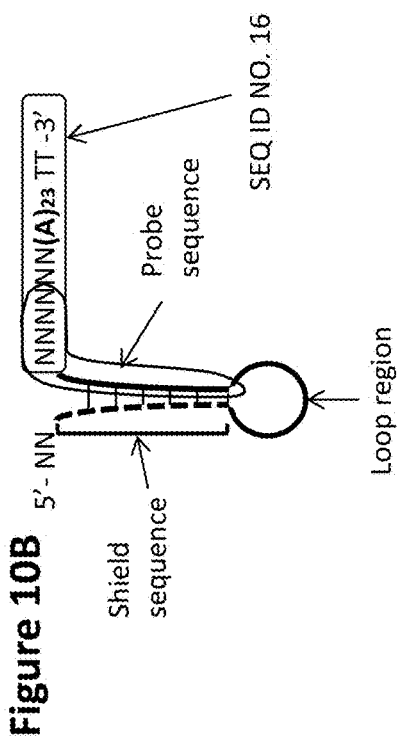
FIGS. 10A-10C provide illustrative embodiments of capture-hook oligonucleotides.
Figure 10A:
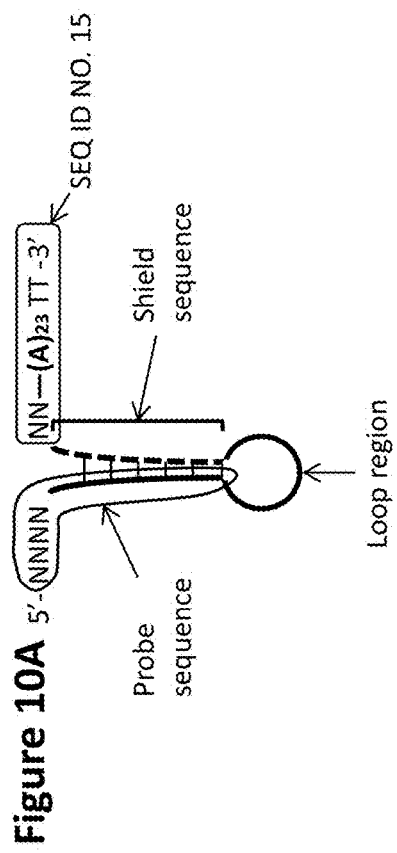
Figure 10C:
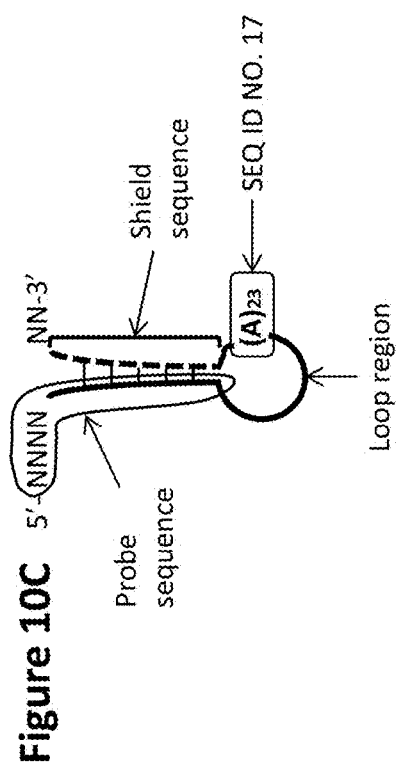

In yet further embodiments, a capture-hook oligonucleotide comprises not only a first region comprising sequence complementary to a target fragment ("probe sequence") and a second region comprising sequence complementary to a substrate-bound oligonucleotide, but also a third region comprising sequence complementary to the first region. For example, the third region can function as a "shield sequence" to increase sequence selectivity, similar to the shielded covalent probes described by Vieregg, et al. (2013, J. Am. Chem. Soc. 135 (26): 9691-9699), which is incorporated herein by reference in its entirety for all purposes. In contrast to the probes of Vieregg, however, the capture-hook oligonucleotides are typically not covalently attached to the target fragments, and usually include a region complementary to a substrate-bound oligonucleotide. The shield sequences are typically 5-15 bases in length, and provide more specific hybridization to the target fragments in the region opened by the polymerase enzyme. In certain preferred embodiments, the capture-hook oligonucleotide folds over on itself to form a hairpin structure in which the first and third regions (probe and shield sequences, respectively) are annealed together. The sequence of the second region complementary to the substrate-bound oligo (e.g., a polyA region) can be at or near the 3'-terminus of the capture-hook oligo, or can be within the single-stranded "loop" region of the hairpin structure. The sequence of the first region complementary to the target fragment is preferably at or near the 5'-terminus, but can be nearer the 3'-terminus, as long as it is still on the 5'-side of the second region. Various capture-hook oligo conformations are shown in FIG. 10, each having the probe sequence circled and the shield sequence shown as a dashed line. FIG. 10A illustrates a conformation in which the probe sequence is near the 5'-terminus, a polyA region is near the 3'-terminus, and the shield sequence is near the polyA region. FIG. 10B illustrates a conformation in which the shield sequence is near the 5'-terminus, a polyA region is near the 3'-terminus, and the probe sequence is near the polyA region. FIG. 10C illustrates a conformation in which the probe sequence is near the 5'-terminus, the shield sequence is near the 3'-terminus, and a polyA region is in the single-stranded loop of the hairpin. These specific constructs are provided as exemplary embodiments, and modifications to these structures can be made without departing from the spirit and scope of the instant disclosure.

Although preferred embodiments of capture-hook oligonucleotides hybridize to a region near the end of a target fragment and near an adapter region where a polymerase enzyme can bind a primer and begin synthesis, in some embodiments a capture-hook oligonucleotide binds further away from the adapter region and more centrally within the target fragment. In some embodiments, multiple different capture-hook oligonucleotides are used to anneal to a single target fragment, thereby providing multiple links to the substrate-bound oligo to enhance capture and retention. In further embodiments, multiple different capture-hook oligonucleotides are used to anneal to different target fragments from a sample nucleic acid, e.g., where it is desirable to sequence all of the target fragments in a single sequencing reaction. In yet further embodiments, a target fragment capped by hairpin adapters is subjected to rolling-circle replication to generate a concatemer comprising repeating complementary copies of the adapter-linked fragment. Multiple capture-hook oligonucleotides can hybridize to this concatemer, since each concatemer will have multiple copies of the sequence to which the capture-hook oligonucleotide is complementary. Each capture-hook oligonucleotide bound provides an additional region that can bind to the substrate-bound oligonucleotides, thereby creating a more stable connection to the substrate. The unbound, non-target fragments and be removed to leave only the target fragments bound. Optionally, the nascent, concatemeric strands can be degraded to recover only the original target fragment capped by the hairpin adapters.

Various affinity capture methods can also be used to further enrich a nucleic acid sample for a target region or fragment of interest. Certain embodiments utilize a stem-loop adapter having one or more affinity tags, e.g., biotinylated bases, where an overhang of the stem-loop adapter is complementary to an overhang created at a restriction endonuclease cut site near a target region. Ligation of the stem-loop adapter having the affinity tag(s) ("tagged adapter") allows fragments linked to the stem-loop adapter to be immobilized and fragments lacking the tagged adapters to be washed away. The immobilization is a result of the affinity tag(s) on the adapter binding to an agent, typically where the agent is bound to a solid surface, e.g., a bead (such as a magnetic or charged bead), column, wall or floor of a reaction container, or the like. Depending on the size and complexity of the starting nucleic acid sample, multiple different fragments may be retained, but the removal of a large number of other fragments will provide a significant increase in the enrichment of the fragments comprising the target region. Following removal of the fragments lacking the tagged adapter, the fragments that are retained are released and subjected to endonuclease digestion (type II or type IIs), stem-loop adapter ligation, and subsequent exonuclease and, optionally, endonuclease degradation to further enrich for the target fragment(s).

Figure 2:
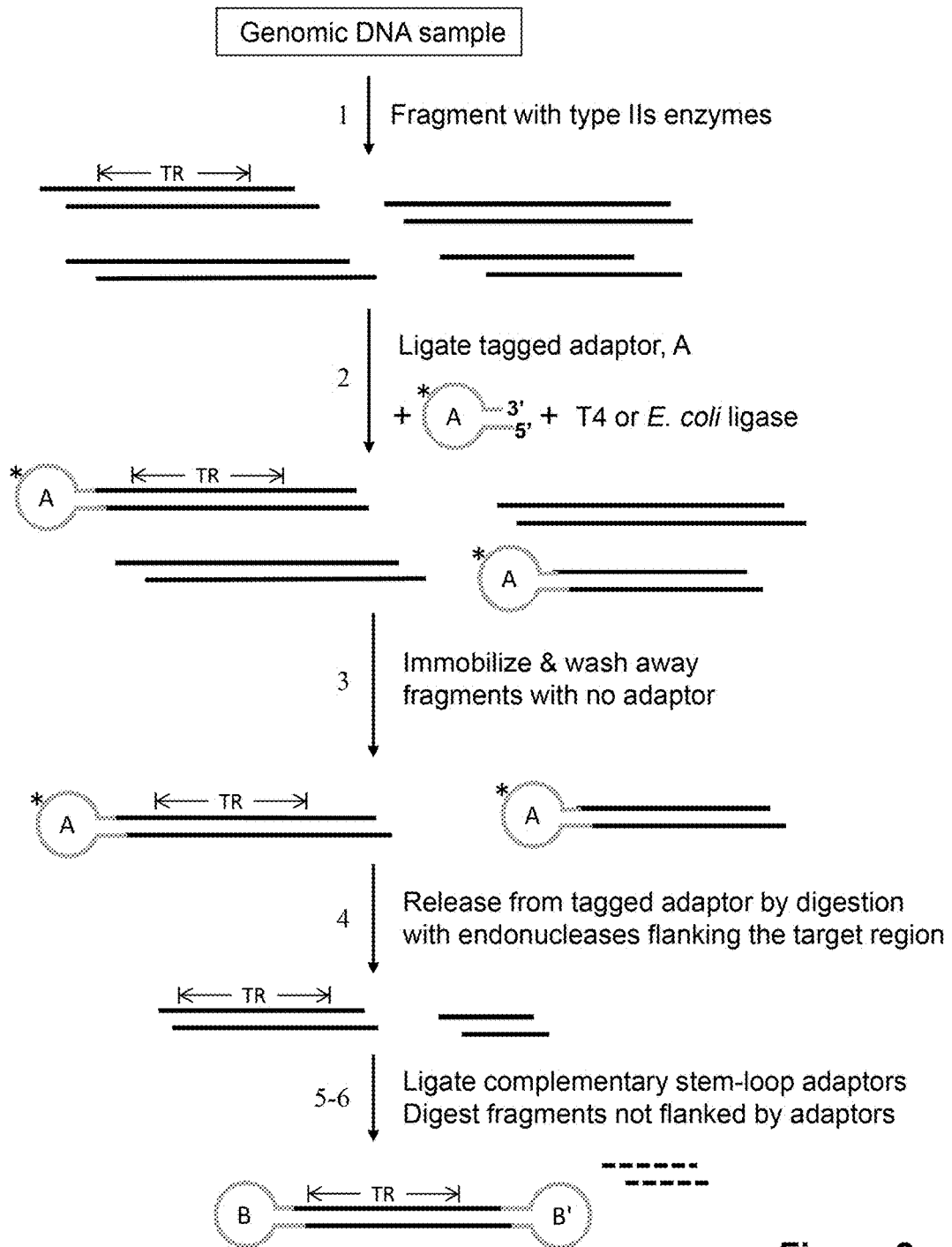
FIG. 2 provides an exemplary embodiment using tagged adapters.
Figure 3A:
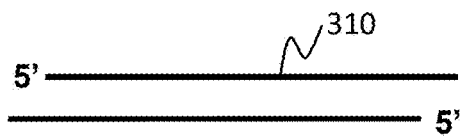
FIGS. 3A-3D provide a graphical representation of one embodiment of an enrichment method described herein.
Figure 3B:
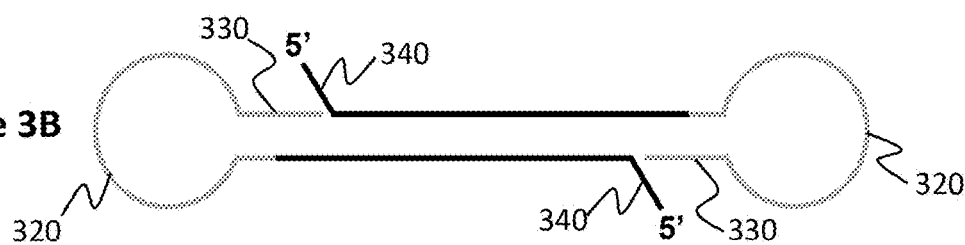
Figure 3C:
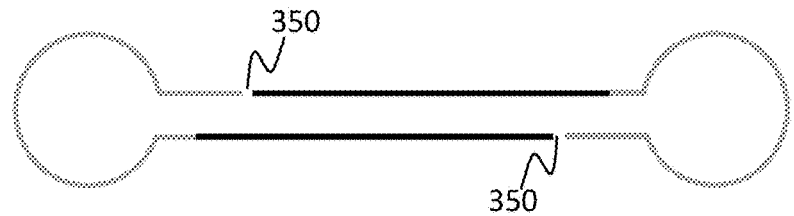
Figure 3D:

FIG. 2 provides an exemplary embodiment using tagged adapters. In step 1, a genomic DNA sample is digested with a type IIs restriction enzyme to provide random single-stranded overhangs at the cut sites. The overhang near the target region (TR) is known. At step 2, a tagged adapter (A) is ligated to fragments having an overhang complementary to an overhang of the adapter, including the fragment comprising the target region. The tag (*) is used to immobilize any fragment ligated to the tagged adapter, and the remaining unligated fragments are removed from the mixture in step 3. In step 4, the immobilized fragments are released from the tagged adapter by digestion with one or more endonucleases that flank the TR, and any other immobilized fragments having recognition sites for at least one of those endonucleases will also be cut, releasing non-target fragments into the mixture. Stem-loop adapters (B, B') having overhangs complementary to overhangs at the cut sites of the endonucleases flanking the TR are ligated to the fragments, and the fragment comprising the TR is therefore capped at both ends with a stem-loop adapter at step 5, and step 6 comprises digestion of the fragments not capped at both ends with exonuclease(s), and optionally also with endonucleases that do not cleave the target fragment. Although the final preparation may comprise non-target fragments having adapters at both ends, it will be significantly enriched for the fragments comprising the target region. The resulting enriched preparation can then be further analyzed, e.g., by sequencing.

This method can be modified in various ways. For example, although the initial fragmentation preferably comprises digestion with a type IIs restriction enzyme having an overhang that is complementary to an overhang of the tagged adapter, other enzymes can also be used. For example, a rare type II cutter can be used where a recognition site is near, but not within, the target region. Preferably, the rare cutter is used in conjunction with one or more additional endonucleases that do not cut within the target region to decrease the size of the resulting fragments. A tagged adapter having an overhang complementary to the overhang generated by the rare cutter is ligated to the mixture of fragments generated by the rare cutter and additional endonuclease(s). The infrequent cutting by the rare-cutting enzyme means that only a small proportion of the fragments will have an overhang complementary to the tagged adapter, allowing removal of the majority of non-target fragments from the mixture.

Another modification is that the tagged adapter could be retained on the selected fragments where the tag can be removed to leave the adapter in a condition that can be processed by a polymerase enzyme. If the tag can be removed without rendering the adapter unsequenceable, then it can be used to block exonuclease at that end of a target fragment and only the opposite end of the fragment needs to be ligated to another stem-loop adapter. In certain related embodiments, the tagged adapter and an adapter at the opposite end of the target fragment are both ligated to the mixture of fragments prior to the affinity-based selection. Endonuclease digestion can be performed to generate specific overhangs at both ends of a target fragment, with one end complementary to the tagged adapter and the other end complementary to a second stem-loop adapter present in the reaction. Preferably, additional endonucleases are included that do not cut the target region and do not leave overhangs complementary to either adapter. The tagged adapters are immobilized, thereby immobilizing the target fragments (which have an adapter at both ends) and other non-target fragments having the tagged adapter, but not necessarily an adapter at a second end. Following removal of non-immobilized fragments, the tagged adapters are removed from the surface (e.g., bead, etc.) and the mixture is subjected to exonuclease treatment to digest any fragments not having an adapter at both ends. In this way, the target fragment is enriched in the mixture of fragments.

In embodiments in which the target (and some non-target) fragments are removed from the tagged adapter by endonuclease digestion, this step can be performed using type II or type IIs restriction enzymes, as long as the enzymes chosen do not cut within the target region. Preferably, only one is used for this step to decrease the numbers of non-target fragments released. Once the released fragments are recovered, they can be subjected to an additional endonuclease digestion to provide an overhang on the opposite side of the target region. Alternatively, digestion both upstream and downstream of the target region may occur simultaneously, e.g., when the fragments are released from the tagged adapters, either using the same endonuclease (cleaving both upstream and downstream of the target region) or using two different endonucleases. Where the same type II endonuclease is used to cut at both ends of the target region, the same stem-loop adapter can be ligated to both ends. Where different type II endonuclease cuts at each end, or where type IIs endonucleases are used that provide different overhang sequences at each end, two different adapters are ligated to the two different termini of the target fragments. Ligation of stem-loop adapters complementary to identical or different overhangs flanking the target region occurs prior to degradation of fragments having terminal nucleotides, i.e., not ligated to a stem-loop adapter. As noted elsewhere herein, one or more exonucleases can be used for this final degradation, and endonucleases that do not cut the target region can optionally be used, as well. The cut sites and overhangs for restriction enzymes are widely known and available to the ordinary practitioner, e.g., from the manufacturer of the enzymes.

Many types of affinity tags can be used in the tagged adapters of the invention. Preferred affinity tags that covalently associate with their binding partner include those known to those of ordinary skill in the art. While covalent interactions are preferred, highly stable non-covalent interactions are also contemplated for use with the methods herein, including but not limited to, biotin (which binds to avidin and streptavidin), and others. Stable, non-covalently associating binding pairs can include, but are not limited to, antibodies that stably bind their antigens and protein receptors that stably bind their binding partners. For example, in certain embodiments, a protein that specifically binds to a sequence of an adapter serves as a "tag" and an antibody for that protein is immobilized on a bead or other solid surface. Binding of the antibody to the protein immobilizes the adapter and any fragment ligated thereto. Proteins that bind to specific sequences in nucleic acids include, e.g., transcription factors, repressors, methyltransferases, etc. Yet further, affinity tags also include hybridization-based tags, such as oligonucleotides complementary to immobilized or immobilizable nucleic acids. Various types of affinity tags are also discussed in greater detail in U.S. Pat. No. 7,745, 116, U.S. Provisional Application No. 61/721,206, filed Nov. 1, 2012, U.S. patent application Ser. No. 14/068,293, filed on Oct. 31, 2013; U.S. patent application Ser. No. 13/427,725, filed on Mar. 22, 2012; all of which are incorporated herein by reference in their entireties for all purposes.

Various modifications can be made to the methods described herein. For example, although type II and type IIs restriction enzymes are discussed at length, use of a "ZFN," or zinc finger DNA-binding protein nuclease, such as those commercially available from Sangamo BioSciences (Richmond, Calif.). ZFNs can be engineered so that their zinc finger domains bind specifically to a particular nucleotide sequence of interest, thereby directing the nuclease activity to that sequence. For example, a first ZFN can be engineered to bind and cleave a particular locus that is upstream of a target region, and a second ZFN can be engineered to bind and cleave a locus that is downstream of the target region. Treatment of a nucleic acid sample will result in the production of a fragment comprising the target region, as well as other fragments that do not comprise the target region. The fragments can optionally be subjected to a size selection to isolate only fragment of approximately the same size as the target fragment. The fragments remaining can be ligated to adapters, and optionally subjected to various nuclease digestions to remove some of the non-target fragments, as described elsewhere herein. The fragments remaining, which will include target fragments, can then be further analyzed, e.g., by sequencing. For more information on ZFNs, see U.S. Patent Publication Nos. 2009/0305419 and 2011/0287512, incorporated herein by reference in their entireties for all purposes.

In certain embodiments of the methods herein, exonuclease degradation is not used to degrade non-target fragments, but instead such fragments are subjected to treatment with terminal transferase in the presence of dATP to create polyA tails on all 3' termini present in the mixture of fragments. This treatment takes place after ligation of flanking adapters, so the ends of the target region are protected from polyA addition. Optionally, after ligation and prior to polyA tailing, the mixture of fragments can be treated with one or more endonucleases that do not cut within the target region. This will provide additional termini on non-target fragments that are available for polyA addition. An optional step can also be performed to repair any internal nick sites in the fragments, which could also be subject to polyA addition. Often the nick is repaired during the ligation of the stem-loop adapters by the ligase enzyme. Other repair enzymes (e.g., polymerases used in DNA repair) may also be used to ensure that the fragments are free of nicks and gaps prior to polyA addition. Following polyA tail addition, the fragments are exposed to immobilized polyT oligonucleotides (e.g., on beads, a column, or other solid surface), which will hybridize to the polyA tails and thereby immobilize the tailed fragments. The non-tailed fragments, including the target fragment, remain in solution and can be recovered and subjected to further manipulations or analysis, e.g., sequencing.

Depending upon the concentration of the nucleic acid sample to be subjected to the enrichment procedures described herein, it may be beneficial to add non-target "carrier" nucleic acids to enhance the nuclease and/or ligase reaction. These reactions can be inefficient where the amount of nucleic acids present is too low. By addition of non-target nucleic acids, the concentration of the nucleic acid sample is raised to increase the efficiency of one or more steps on the method. Ironically, addition of carrier effectively "un-enriches" the sample for the target region prior to the enriching procedure, however, can result in production of a more enriched sample by the end of the procedure. In preferred embodiments, the non-target nucleic acids added are preferably lacking recognition sites for the endonucleases used to generate the cuts flanking the target region, although in some embodiments they do comprise recognition sites for other endonucleases used to degrade non-target nucleic acids. In some embodiments, these additional non-target nucleic acids are linked to affinity tags to allow their efficient removal from the nucleic acid sample once there is no more need for a higher nucleic acid concentration. In some embodiments, the carrier nucleic acids lack an affinity tag that is linked to target fragments, so that they can be removed with other non-target nucleic acids during the enrichment procedure. Different types of carrier nucleic acids are known and used in the art, e.g., DNA from lambda phage, plasmid DNA, synthetic oligonucleotides, etc. In certain embodiments, a double-stranded circular carrier is used, e.g., plasmid DNA. Preferably, the double-stranded circular carrier is treated prior to use with one or more exonucleases to ensure there are no 3' or 5' ends that could interfere with the enrichment procedure, e.g., by linking to adapters intended for the nucleic acids being enriched. This also ensures that the carrier will not be degraded in any exonuclease treatments that may be included in the enrichment process. Preferably, the carrier does not comprise nucleic acid sequences that are selectable in (or would otherwise interfere with) the enrichment procedure, e.g., by being identical to target sequences, driver sequences, or oligos (e.g., comprising homopolymer regions) linked to substrates used to pull down the target fragments. The target fragments can be purified away from the remaining carrier molecules by virtue of an affinity tag or driver-hybridization procedure, or, optionally, by specific cleavage of the carrier once it is no longer needed, followed by exonuclease digestion.

Various methods can be used to determine the effectiveness of the enrichment procedure. For example, in certain preferred embodiments, relative fold-enrichment is calculated by the following steps. First, the ratios of [target fragments]/[non-target fragments] for the sample prior to enrichment is estimated. In some cases, the ratio for the original sample (i.e., pre-enrichment) is based on the theoretical digestion by the restriction endonuclease(s) used, assuming 100% digestion efficiency and that all four canonical bases are evenly distributed in the sample (e.g., 25% of each). Alternatively or additionally, where sequence data for the entire sample is available, the ratio of target:non-target fragments can be based on the number of sequencing reads mapped to the target region over the total number of sequencing reads for the sample. The ratio for the enriched sample is based on sequencing data generated using the enriched sample, and is preferably computed as the number of sequencing reads mapped to the target region divided by the total number of sequencing reads in all. In alternative embodiments, the number of sequencing reads mapped to the target region can be compared to those mapped to the non-target regions in the sample. The fold-enrichment is calculated by dividing the ratio for the enriched sample by the ratio for the non-enriched sample.

Determination of a specific yield of the fragments capped at both ends by an adapter in the enriched sample can comprise use of various commercially available nucleic acid quantitation systems, e.g., spectrophotometry or fluorimetry (e.g., using a Qubit® system). The measure of the amount of double-stranded nucleic acids in the enriched sample relative to the total amount of nucleic acids in the non-enriched sample is one measure of the yield of fragments provided by the enrichment method. However, this yield may include some quantity of non-target fragments that have also been ligated to two adapters, so will not necessarily reflect the amount of target fragments that are recovered.

In other aspects, enrichment of specific sequences of interest is achieved through circularization of fragments generated from a sample source, where the circularization reaction is dependent upon the presence of specific sequences known to flank a region of interest and does not rely on stem-loop or hairpin adapters. In brief, fragments comprising the region of interest are circularized by hybridization to a selector probe that is complementary to the end of the desired fragment. A final step of ligation creates a covalently closed circular construct. The original fragment can be single-stranded, or double-stranded. For a single-stranded fragment (SSF), a single-stranded oligo having one end complementary to one end of the SSF, and the other end complementary to the other end of the SSF, would bring the two ends together. Where the oligo has the two complementary regions immediately adjacent to one another, a ligation step connects the ends of the SSF to create a single-stranded circular molecule. Alternatively, where the oligo has the two complementary regions separated by some number of bases, the gap formed between the ends of the SSF after annealing to the oligo is filled in by extension of the 3'-end of the SSF prior to the ligation step. For a double-stranded fragment (DSF), the 5' ends would be degraded a short distance prior to adding a double-stranded adapter having a first 3' overhang at a first end that is complementary to a first 3'-overhang on a first end of the DSF. Similarly, the double-stranded adapter has a second 3' overhang at a second end that is complementary to a second 3'-overhang on a second end of the DSF. Typically, an extension reaction would extend the 3' ends of the adapters once annealed to the ends of the DSF, and a subsequent ligation reaction would create a double-stranded circle. For specific enrichment of a region of interest, both the SSF and DSF fragments must have known sequences at the ends, and these sequences must be unique enough that their selection results in enrichment of the region of interest to a desired level. Following circularization of the SSF or DSF, nuclease treatment degrades the nucleic acids that are not circularized, i.e., that do not have the defined sequences on the ends that are complementary to the adapter used to circularize the desired fragments. This provides a mixture enriched for the sequences of interest.

In certain embodiments, the resulting circular molecules are amplified to further enrich for the presence of the region of interest. For example, a single-stranded circular molecule can be subjected to rolling circle amplification to generate a strand comprising multiple complementary copies of the single-stranded circle. This mode of amplification is preferable to conventional PCR, which can introduce and perpetuate changes in the population of amplicons generated, and these changes cannot be distinguished from true variants in the original template strands. In contrast, rolling-circle replication creates multiple complementary copies of the original template, and while it is possible that changes can occur during synthesis, these changes are not perpetuated since the newly synthesized strand is not used as a template strand. As such, any random changes introduced will not be replicated in additional molecules, and true variants will be readily distinguishable. These complementary copies can be sequenced and the sequence data analyzed to determine, by complementarity, the sequence of the original SSF. For a double-stranded circle, the construct can be linearized, either by repeating the initial fragmentation reaction that generated the original set of fragments. This step would remove the adapter and linearize the fragments. Subsequent PCR with primers complementary to the known ends of the fragment would provide amplification of the desired sequences and a greater fold-enrichment in the mixture. Alternatively, the central portion of the double-stranded adapter can comprise a restriction site to allow linearization of the construct, and the PCR primers can be complementary to sequences within the double-stranded adapter, sequences in the original fragment, or complementary to both (e.g., anneals across the junction between the adapter sequence and the fragment sequence. Amplification will increase the amount of the desired nucleic acid in the mixture, further diluting any contaminating non-target sequences that survived the nuclease treatment.

In yet further aspects, a branch-capture reaction (BCR) is used to enrich a mixed nucleic acid population for target regions of interest. BCR is a molecular biology technique that allows capture of genomic DNA fragments for ligase-mediated PCR and cloning (see, e.g., Barany, F. (1991) Genome Research 1:5-16). The method requires a sample nucleic acid to be treated to produce restriction fragments terminating in an overhang. A displacer oligonucleotide and a linker oligonucleotide form an adapter having a biotin tag on the linker oligonucleotide, and the displacer oligonucleotide, being complementary to the overhanging strand ("first strand"), anneals at high temperature (65° C.) to the first strand and displaces a portion of the recessed strand ("second strand") at the terminus of the fragments. The linker oligonucleotide is linked to the end of the first strand using a thermostable ligase with high specificity. The displacer oligonucleotide is subsequently extended to fully displace the second strand, which generates a blunt end at the opposite end of the fragment. A blunt-ended adapter is ligated to the newly generated blunt end and the biotin-labeled strand (the first strand ligated to the biotin-labeled linker oligonucleotide) is captured using a binding partner for biotin, e.g., streptavidin. A first primer specific for the region of the first strand complementary to the displacer is annealed to the first strand and extended to generate a nascent strand complementary to the captured strand, thereby creating a double-stranded molecule (captured strand and nascent strand) with a 3'-overhang at one end, the overhang being the original linker oligonucleotide sequence. PCR is subsequently performed using both the first primer and a second primer complementary to the 3'-end of the nascent strand.

A related but novel method is provided herein that provides enrichment of target regions using stem-loop adapters that displace a portion of one strand at an end of a nucleic acid fragment. The method is illustrated in FIG. 3 and begins with providing a double-stranded fragment (310) comprising a target region, where the fragment has termini with known sequences that flank the target region and, preferably, also have 3' overhangs. Stem-loop adapters (320) having 3' overhangs (330) complementary to the known terminal sequence of the strand comprising the 3' overhangs are introduced to the fragments under high temperature conditions (e.g., 65° C.), where the portion of the 3' end of the fragment that is complementary to the 3' overhang of the adapter extends into the duplex portion of the fragment. Annealing of the 3' overhang of the adapter to the fragment partially displaces the other strand having the recessed 5' terminus. The 3' terminus of the fragment is ligated to the 5' terminus of the adapter, also at high temperature. The displaced portion (340) is digested by a single-stranded exonuclease, e.g., ExoT, to leave a nick (350) which is repaired by a second ligase reaction using either the same or a different ligase as was used in the first ligation. Alternatively, an enzyme cocktail can be added to not only repair the final gap, but also to repair other damage that might be present in the target region, e.g., the PreCR® Repair Mix from New England Biolabs, Ipswich, Mass.). Following repair of the final gap, the newly formed molecule (360) comprises the target region and no terminal nucleotides. Subsequent nuclease treatment (e.g., with ExoIII and ExoVII) removes all other non-target molecules and unligated adapter sequences, thereby enriching the mixture for the target region-containing constructs. Since attachment of adapter sequences to both ends is dependent upon complementarity to the adapter overhang sequences, only regions flanked by sequences complementary to the adapter sequences will have adapters added to both and, in doing so, be protected from the nuclease degradation.

In further aspects, biotinylated probes can be used to select specific target regions to generate nucleic acid compositions enriched for the target regions. In preferred embodiments, no amplification is required during the enrichment process, so any modifications in the target nucleic acids are preserved for further analysis. Such embodiments typically comprise the following general steps: (1) use a hybridization-based approach to obtain an enriched single-stranded nucleic acid from a biological sample; and (2) convert the enriched single-stranded nucleic acids into double-stranded molecules. One strand of the double-stranded (or "duplex") molecules is native nucleic acids from the original sample, having any additional modifications (e.g., methylated nucleotides) present in the original sample. The other strand is synthesized in vitro, and so comprises only the types of nucleotides present in the synthesis reaction, e.g., typically canonical, non-modified nucleotides.

Optionally, further manipulations can be performed, e.g., where required for additional analytical techniques. For example, in certain embodiments the double-stranded molecules are converted into sequencing templates, such as those used in single-molecule sequencing that link both strands of the duplex together. This can be accomplished by attaching a hairpin or stem-loop adapter to one or both ends of the duplex molecules. In particularly preferred embodiments, the duplex is converted into a SMRTbell™ template, as described elsewhere herein, and in U.S. Pat. No. 8,153,375, incorporated herein by reference in its entirety for all purposes.

In an exemplary process, nucleic acids isolated from a biological source are fragmented, treated to create blunt ends, and the resulting fragments are subjected to a ligation reaction to link adapters to the ends. Each adapter comprises two strands that are hybridized together to form a stem-loop structure having a double-stranded terminus at the end of the "stem" that is capable of being ligated to the ends of the fragments. A first strand of the adapters has a central region that is complementary to the 3' end such that the 3' end folds back and anneals to the central region in cis to form a molecule having a single stranded loop and a stem portion with a 5' single-stranded overhang. The second strand of the adapters is complementary to the 5' single-stranded overhang. Annealing of the strands together therefore provides a stem-loop adapter having a nick at the location where the 3' end of the first strand and the 5' end of the second strand are adjacent, but not linked, to one another. The second strand also preferably comprises a convertible nucleotide, internally located, the purpose of which is further described below. Once the adapters are added to the end of the fragments, a denaturation step is performed to separate the duplexes into single-stranded molecules, each with a first strand of the adapter linked at the 3' end and a second strand of the opposite adapter linked at the 5' end.

Converting the duplex to a single-stranded molecule provides access to driver or "bait" molecules that hybridize and provide an affinity selection for those comprising target regions of interest, as described further elsewhere herein. For example, oligonucleotides having affinity tags attached thereto can be annealed to the single-stranded target molecules and the tags used to immobilize the target molecules so the on-target molecules can be removed from the mixture. The oligonucleotides can be RNA, DNA, or analogs or mimetics thereof, and the tags can be any that have a sufficiently strong binding to allow removal of non-target molecules. For example, the Agilent® SureSelect® platform uses biotinylated RNA polymers as the bait molecules and streptavidin as the binding partner to immobilize the target fragments on beads in solution.

After the target fragments are isolated from the non-target fragments, the driver/bait oligonucleotides are removed, e.g., by denaturation. The resulting single-stranded molecule comprises the first strand of the adapter on the 3' end, and the 3' end of the adapter strand is looped back and annealed in cis to a central portion of the adapter strand. A polymerase enzyme is used to convert the single-stranded molecule to a double-stranded molecule by extending the 3' end of the first strand of the adapter and generating a complementary nascent strand. In some embodiments, a second hairpin structure is desired on the terminus corresponding to the 3' end of the extended strand. Various ligation methods can be used, but in certain preferred embodiments a cohesive end is generated by degrading the 5' strand back to the position of the convertible nucleotide mentioned above as being at an internal position in the second strand of the adapter. This strategy avoids the use of restriction endonucleases that could cut the target nucleic acid sequence. For example, a deoxyuridine nucleotide within the second strand can be converted to an abasic site using uracil DNA glycosylase, and the abasic site subsequently excised from the molecule using an AP-lyase activity (e.g., from *E. coli* endonuclease III (Nth) protein) that leaves a ligation-competent end comprising a 5' phosphate group immediately downstream of the excision event. Since sequence of the resulting 3' overhang is known since it is complementary to the known sequence of the second strand of the adapter. As such, this cohesive end can be ligated in trans to an adapter (e.g., hairpin or stem-loop adapter) having a 3' overhang complementary thereto. Preferably, a ligase only capable of ligating sticky ends is used, e.g., NAD-dependent ligases such as *E. coli* or *T. aquaticus* DNA ligases. Where the adapter is a stem-loop or hairpin adapter, the resulting molecules are closed having no terminal nucleotides, and are therefore immune to exonuclease digestion. As such, subsequent exonuclease treatment is typically used to remove any contaminating (non-target, excess adapters, etc.) nucleic acids. The final mixture comprises only molecules that are resistant to such treatments, and is enriched for the target molecules by virtue of the selection step.

Various modifications to the above-described method are contemplated. For example, the adapter strands and/or driver (bait) molecules can comprise various types of nucleotides or analogs thereof, including but not limited to DNA, RNA, LNA, PNA, chimeric biopolymers, phosphorothioate-containing nucleotides, and combinations thereof. Further, different modifications can be present at the 5' end of the second adapter strand to prevent ligation to the 3' and of the first adapter strand. Only one strand of the sample nucleic acid fragment can be selected by constructing the adapters such that they only ligate to the desired strand, e.g., through 5' or 3' modifications. Different convertible nucleotides could be used other than deoxyuridine, e.g., deoxyinosine, thiolated or halogenated bases, RNA bases, methylated bases, and the like. These provide for targeting by different nucleic acid modifying enzymes or combinations thereof. In some embodiments, the adapter sequences can be tagged with an affinity or reactive moiety (e.g., biotin, azide, etc.) to allow for purification of the adapter and accompanying sample nucleic acid. These moieties can be added to either the adapters added prior to enrichment, those added after the enriched molecules are converted to double-stranded form, or both. The enrichment strategy can be solution-based (e.g., Agilent® SureSelect® system, IDT® NGS target capture, etc.) or can be array-based (e.g., NimbleGen® or Affymetrix® systems, etc.). Likewise, the driver/bait molecules can comprise tags other than biotin, and the tagging can occur via reactive groups such as an azide, primary amine, thiol, or halogenated base. In addition, the sample nucleic acid can be subjected to treatment prior to attaching adapters or at other points in the process. In some embodiments, modifications present in the sample nucleic acid are further modified, e.g., by treatment with one or more enzymes, thereby converting them to a different or altered modification that can be analyzed at a later time. For example the different or altered modification can serve as a proxy for the original modification, which may be difficult to detect prior to the treatment.

III. Additional Methods for Capture of Target Nucleic Acids

Certain preferred embodiments of the methods provided herein enrich target nucleic acids, at least in part, by "capturing" them in a manner that allows their isolation from some or all of the non-target nucleic acids in a sample. Capture of target sequence facilitates targeted sequencing of specific regions of a genome, chromosome, metagenomic, or other nucleic acid sample. Further, since it is desirable to retain base modifications (e.g., methylation, adenylation, damaged bases, glucosylated bases, etc.) present in a sample nucleic acid molecule for further analysis (e.g., direct detection during a sequencing reaction), capture methods that do not rely on amplification of the sample nucleic acids are of particular interest. Where nucleic acids from different sources are to be pooled prior to further analysis, barcode adapters specific for each source are preferably linked to all nucleic acids from that particular source. This allows identification of the source of a particular sequence read from a subsequent pooled sequencing reaction by virtue of detecting the sequence of a barcode identifying the source. This multiplexing can combine various types of sources, e.g., different individuals in a population, different tissues in an individual, different portions of a genome, and the like.

In certain embodiments, adapters are added to the sample nucleic acids to link the 3' and 5' termini at each end, e.g., by addition of hairpin or stem-loop adapters. The resulting construct comprises a double-stranded portion that includes the original sample nucleic acid flanked by the adapters, and separation of the strands of the double-stranded portion results in a single-stranded circular molecule having both strands of the original nucleic acid in a single, contiguous strand. These constructs are further described elsewhere herein. Once formed, the adapter-flanked molecule is subjected to a treatment that separates the complementary strands of the double-stranded insert to allow binding of one or more oligonucleotide primers that are complementary one or more regions of interest in the original sample nucleic acids. Similar to the driver molecules described above, the primers will only bind to molecules that have the complementary sequences, and therefore that comprise a region of interest. Following annealing of the primers, primer extension is carried out in the presence of biotinylated (or otherwise affinity tagged) nucleotide analogs such that the nascent strand generated comprises biotin tags (or other affinity tags) that can be used in a subsequent affinity purification step. For example, only the constructs that have a tagged extension product will be immobilized, e.g., on a bead, surface, column, etc., that is coated with a binding partner for the tag. For example, to immobilize a biotin tagged product, a bead coated with avidin or streptavidin can be used. Nucleic acids that are not immobilized or "captured" are removed by conventional methods, e.g., washing/buffer exchange, spin column, chromatography, etc. Once isolated, the biotin-tagged extension product can be removed, e.g., by denaturation, and the resulting isolated nucleic acid pool is enriched for the one or more regions of interest targeted by the oligonucleotide probes. This enriched pool is subsequently subjected to further analysis, e.g., sequencing, preferably with no amplification and/or removal of the adapter sequences.

FIG. 4A-4D provides a graphical representation of one embodiment of the method described above. FIG. 4A illustrates a nucleic acid construct having a double-stranded sample nucleic acid insert (410) flanked by two stem-loop adapters (420). FIG. 4B shows the same construct after denaturation and addition of an oligonucleotide primer (430) that targets a region of interest. The target primer is extended using nucleotides that are linked to biotin tags (440) to generate the construct shown in FIG. 4C having a biotin-labeled extended primer (450). Subsequent pull-down of the biotin-labeled construct allow removal of non-target-containing nucleic acids (not shown). Subsequently, the biotin-labeled extension product (450) is removed from the construct by denaturation, and a sequencing primer (460) is annealed to at least one of the stem-loop adapters to arrive at the construct in FIG. 4D. This construct is shown under non-denaturing conditions, so the two strands of the double-stranded insert (410) have annealed together again. This complex can be subjected to further analysis, e.g., sequencing-by-synthesis, amplification, etc. Although not shown here, in some preferred embodiments, addition of the sequencing primer occurs coincident with addition of a polymerase enzyme, resulting in a template/primer/polymerase enzyme complex that is appropriate for a sequencing-by-synthesis reaction.

The above-described method provides several advantages to the ordinary practitioner. First, adapter ligation is more efficient with higher concentrations of nucleic acid insert, so by linking the adapter to the entire pool of sample nucleic acids prior to enrichment, the ligation reaction is improved. Second, the presence of both strands of the double-stranded insert in the construct keeps them linked together, allowing analysis that can associate data from one strand with data from the other. For example, where modifications are detected the practitioner can determine whether the modifications occur on only one or both strands. Further, because the method does not require amplification of the sample nucleic acids, this modification information is preserved in the enriched pool of nucleic acids for subsequent analysis, and is particularly suitable for kinetics-based detection during single-molecule, real-time, polymerase-mediated sequencing reactions (e.g., SMRT® Sequencing, Pacific Biosciences, CA). More information on detection of modifications during sequencing reactions is provided in detail, e.g., in International Application Publication No. WO 2012/065043 A2 and U.S. Provisional Application Ser. No. 61/721,206, filed Nov. 1, 2012, both of which are incorporated herein by reference in their entireties for all purposes.

Although biotinylated nucleotides are used to generate the extended primer in the specific example provided above, other types of capturable modifications can be incorporated into these nucleotides, as long as they don't prevent the primer extension reaction. These capturable modification systems include binding partners, such as biotin/streptavidin or biotin/avidin; antigen/antibody interactions; and can also include covalent interactions. The latter system can be beneficial to ensure removal of the tagged, extended primer from the enriched sample nucleic acid constructs because after removing the extended primers from the constructs, the primers will remain bound to the solid surface, bead, etc., which facilitates their removal from the mixture. Where the bond is noncovalent there is a higher likelihood that some of the tagged primers may remain in the solution with the enriched constructs during the subsequent analysis.

Although the method above describes linking of stem-loop adapters to both ends of a double-stranded sample nucleic acids, the method does not require that both ends be linked to adapters. In some embodiments, only one end is linked, which will also preserve the connection between both strands of the original nucleic acids. In fact, neither end needs to be linked to a stem-loop adapter if this connection is not needed or desired. In some embodiments, the connection can be maintained by adding barcode adapters to one or both ends. The sequence of the barcode detected during a subsequent sequencing reaction can be used to link the data from the two strands during data analysis in embodiments in which both strands are targeted by the oligonucleotide probes. In yet further embodiments, only a single strand is isolated and sequenced, and the sequence of the other strand is determined based on the complementarity between the two strands. In some embodiments, e.g., where modifications need not be preserved for further analysis, the enriched nucleic acids can be subjected to amplification to increase the total amount of nucleic acid in any subsequent procedures. For example, primer-binding sites in adapter regions can be used to PCR amplify the portion of the nucleic acid construct that they flank.

As noted above, more than one oligonucleotide probe can be used to select desired regions of a nucleic acid sample. In some embodiments, one probe anneals to a first strand of a region of interest and a second probe anneals to the complementary strand. Alternatively or in addition, probes can target different regions within a single contiguous nucleic acid sequence, e.g., along a single gene, chromosome, regulatory region, repeat region, and the like. Yet further, probes can target multiple different regions that share a characteristic of interest, e.g., involvement in a biologic pathway (e.g., metabolism, transcriptional regulation, carcinogenesis, endocrine response, etc.) under investigation. Primers can also target specific alleles of interest, e.g., by being complementary to one or more SNP positions known to be within the particular allele of a gene. These primer targeting methods can be used in combination, as well. Further, the methods herein may be usefully combined with those of U.S. Patent Publication Nos. 20060040300, 20080090733, and 20090263798, the disclosures of which are incorporated herein by reference in their entireties for all purposes.

In some embodiments, regions of interest ("target regions") can be captured using molecular inversion probes. Briefly, molecular inversion probes are oligonucleotides having termini that are complementary to regions flanking a region of interest in a sample nucleic acid molecule such that when annealed to the sample nucleic acid the termini of the probe are oriented toward each other with a gap between them. Because of this orientation, extension of the 3' end of the probe "fills in" the gap with a sequence of nucleotides complementary to the target region in the sample nucleic acid, and subsequent ligation circularizes the probe, effectively "capturing" sequence correlating with the target region into a single-stranded circular molecule. In some embodiments, treatment with one or more nucleases degrades all non-circularized probes so only the circularized ones remain for further analysis. Alternatively or in addition, the gap-filling operation is performed with tagged nucleotides to allow capture of the extended probes with a binding partner, e.g., on a bead, column, or other surface. In other embodiments, a tag sequence is incorporated into the probe itself to allow pull-down of all probes whether or not they were extended and ligated. However, in combination with nuclease treatment, only probes that are circularized will be preserved for further analysis, e.g., sequence analysis.

In some embodiments, the terminal regions of the probe include restriction sites to allow cleavage of the double-stranded portion formed by extension of the 3'-end of the probe on the sample nucleic acid, which can then be further manipulated as a double-stranded, linear molecule, e.g., by addition of adapters (as discussed elsewhere herein) and/or further analysis. For example, in some such embodiments the circularized probes are subjected to the pull-down operation while still bound to the nucleic acid samples prior to the restriction digestion. In other embodiments, the restriction digestion is performed prior to capture of the double-stranded product of the cleavage. The latter method is most appropriate where there is no exonuclease treatment performed that could degrade the linear, double-stranded nucleic acid molecule. In either case, the double-stranded nucleic acid generated will comprise one strand of the sample nucleic acid that includes the target region, and a second strand from the probe that includes the region synthesized during the extension reaction that is complementary to the target region.

In some embodiments, the circularized probe is isolated while still bound to the sample nucleic acid, and subsequently subjected to a nicking reaction to provide a 3' terminus at or within a few bases of an end of the double-stranded portion formed between the probe and the target nucleic acid. For example, a nickase recognition sequence can be integrated into the probe design such that it occurs near the 3' end of the probe. The resulting 3' end generated in the probe is suitable for initiation of a polymerase-mediated sequencing reaction using a polymerase capable of strand displacement. This strategy places the sequencing polymerase in position to cross the target region during the sequencing reaction, thereby providing a sequencing read for the target region of the sample nucleic acid.

In certain alternative embodiments, a target region can be captured that is not located between the two regions complementary to the probe termini, i.e., where the target region is outside of the region complementary to the extended probe. For example, where nuclease treatment is not used to remove unligated probes and the annealing of the probe to the sample nucleic acid is sufficiently stable, no ligation reaction is performed and the nick produced by the extension of the 3' end of the probe is retained. Tag-based capture of the resulting unligated probe/target hybrid molecule is performed, and the nick serves as a binding site for a strand-displacing polymerase, which is positioned to sequence a target region that is adjacent to the region complementary to the 5' end of the probe. A benefit to this strategy is that the presence of the 5' end of the probe annealed to the sample nucleic acid prevents the initial extension reaction from extending into the target region, thereby positioning the initiation site for a sequencing polymerase upstream of the target region for which sequence data is desired.

In yet further embodiments, a fluidic system can be used to separate tagged target molecules from untagged, non-target molecules. Such tags are sometimes referred to as "drag tags" and separate target from non-target by controlling their passage through the fluidics system, e.g., by slowing passage, quickening passage, or redirecting passage. In some strategies, a tag is a charged particle linked to a portion of a target molecule, but not linked to non-target molecules. For example, the charged particle can be linked to an oligonucleotide that is complementary to target fragments, but not non-target fragments. A pool of tagged, target fragments and untagged, non-target fragments are placed in a channel of a microfluidics device having a current flow such that negatively charged molecules will move toward the (+) end of the channel. In some embodiments, the charged particle has a positive charge large enough to direct the movement of the tagged molecules toward the (−) end of the channel, while the untagged molecules, which naturally have a negative charge, move toward the (+) end of the channel. After allowing sufficient time for migration to the (−) end, the target molecules are removed from the (−) end of the channel. Alternatively, the charged particle can have a negative charge that is sufficient to pull the target fragments more quickly to the (+) end than the untagged molecules. After allowing sufficient time for migration of the tagged molecules to the (−) end, but insufficient for migration of the untagged molecules, the target molecules are removed from the (+) end of the channel. In both scenarios, the target molecules are separated from the non-target molecules, resulting in an enrichment of the target molecules in the final mixture removed from the microfluidic channel. In related embodiments, a magnetic particle can be used to tag the target molecules rather than a charged particle, and a magnetic field can be used to separate the tagged molecules from the untagged molecules. In some embodiments, a combination of current and magnetism is used. For example, a magnetic tag is linked to target fragments, a current is applied that pulls all nucleic acids toward the (+) end of a channel, and a magnet is used to pull the tagged fragments toward the opposite end of the channel, where the magnetic field is stronger than the current. In yet further embodiments, the channel is placed in a vertical position and the tags are particles that have a mass that pulls the tagged molecules toward the bottom of the column while the untagged molecules move toward the (+) end of the channel, which is oriented upward. This method uses both charge-based and gravity-based strategies to separate target from non-target molecules.

While some methods comprise pre-attaching the tags to the target molecules prior to transferring the target and non-target molecules to a fluidics system, other methods comprise attaching the tags during the separation process, e.g., within the channel of a fluidics system. For example, the tags can be flowing through a channel and the untagged target and non-target fragments added to the channel, e.g., via a port on the side of the channel. The tags in the channel attach to the target molecules, but not the non-target molecules, resulting in a change of the movement of the target molecules that causes their separation from the non-target molecules, e.g., in the charge-based, magnetic field-based, and/or gravity-based methods described above. For example, where a positively charged tag is used, it can be continually flowing toward the (−) end of the channel, e.g., from a large vessel in fluid communication with the (+) end of the channel. The untagged nucleic acids are moving toward the (+) end of the channel, in the opposite direction as the tags. When a tag encounters a target molecule, it attaches to the target and reverses its direction so that it begins to flow toward the (−) end of the channel, where it is eventually collected. In a similar embodiment, magnetic tags are present in the channel with the untagged molecules. When a tag encounters a target molecule, it attaches to the target. After a length of time sufficient for binding of tags to targets, an electric field is applied to pull untagged molecules in one direction and, simultaneously, a magnetic field is applied to pull tagged molecules and unbound tags in the opposite direction, thereby separating tagged from untagged molecules.

While the above methods refer microfluidics systems, it will be understood that these systems can comprise fluids of varying densities and viscosities, including gels, oils, and other polymer-containing fluids. Further, the flows of molecules can be changed in various ways, e.g., by introducing or changing a rate of fluid flow, a strength of current flow, a strength of magnetic pull, or a combination thereof, during the course of the separation process. For example, a magnetic or electric field can be constant, pulsed, or can otherwise vary during the course of the separation. In some embodiments, only a single tag is sufficient to separate target from non-target, but in other embodiments separation required binding of multiple tags to a single target molecule. For example, where the target is a highly repetitive region, a non-target region may comprise one of the repetitive sequences. To ensure that only the highly repetitive region is captured, the separation required binding of multiple tags, ensuring that multiple copies of the repeat region are present in the molecules that are eventually recovered. These methods can be used in combination with other fluid-based separation techniques known in the art, e.g., Dhopeshwarkar, et al. (2005) Lab Chip 5:1148-1154, which is incorporated herein by reference in its entirety for all purposes.

IV. Methods Utilizing Tester-Driver Strategies

In certain aspects, the present invention provides tester-driver strategies to enrich a nucleic acid sample for a modification of interest. As used herein, a "tester" nucleic acid population is a set of nucleic acid molecules comprising target nucleic acid molecules and non-target nucleic acid molecules. In contrast, a "driver" nucleic acid population comprises nucleic acid molecules that can bind, e.g., hybridize, to select nucleic acid molecules in the tester population, e.g., preferably either the target nucleic acids or the non-target nucleic acids in the tester population, but not both. (Driver nucleic acids are sometimes also referred to as "bait" nucleic acid molecules.) Hybridization between the tester and driver populations followed by a selection for tester molecules that hybridize to driver molecules allows separation of target from non-target nucleic acid molecules from the tester population. The driver nucleic acids often hybridize to the target nucleic acids in the tester population, and the selection allows retention of the target nucleic acids and removal of the non-target nucleic acids. In other embodiments, the driver nucleic acids hybridize to the non-target nucleic acids, allowing removal and subsequent analysis of the "free" target nucleic acids. As such, a tester-driver strategy can comprise either a positive or negative selection, or in some cases both a positive and a negative selection can be performed, e.g., sequentially using two or more different driver populations. Further, tester and driver molecules can be any type of nucleic acid molecule described herein, e.g., DNA, RNA, DNA/RNA hybrids, nucleic acids with modified bases, nucleic acids with tags or barcodes, etc. The length and base composition of the driver molecules can also be varied, depending on the type of sequence to be captured. For example, capture of a highly repetitive sequence may require a longer driver sequence that includes both a flanking sequence and a portion of the repeat region, or may be long enough to select a particular haplotype that spans two or more variable base positions. In certain embodiments, driver sequences are used within larger constructs, such as within capture-hook oligonucleotides, which are described in detail elsewhere herein.

In certain embodiments, pools of driver molecules are typically created where selection a set of target sequences is desired. For example, a pool of driver molecules can select organelle-specific genomes, e.g., mitochondrial or chloroplast genomes. Such a pool of driver molecules would include only sequences unique to the organelle genome, e.g., that are absent from the nuclear genome. In other cases, a pool of driver molecule can select only nucleic acids originating from a particular chromosome or set of chromosomes. This can be particularly useful for analysis of very small chromosomes, such as chromosomes 21, 22, and Y, since they represent such a small proportion of the total nucleic acids in the cell. A pool of driver molecules can select a particular set of mRNAs by comprising sequence complementary to regions unique to the set of mRNAs. For example, an appropriate driver can comprise a 5' polyT sequence adjacent to a region complementary to the portion of the desired mRNA adjacent to its 3' polyA tail. Yet further, given the increasing interest in noncoding or "junk" DNA, driver pools can be used to specifically select sequences within these regions of the genome, which have traditionally been excluded from such analysis. Often, such noncoding regions are highly repetitive, so in some methods a driver population comprises highly repetitive sequence that can bind stably to repeat regions and allow their capture and isolation from non-repeat regions. In additional embodiments, two different types of nucleic acids can be selected using a driver population having sequences that are complementary to both types of nucleic acids, e.g., both genomic DNA and RNA transcripts. For example, a driver population that comprises molecules complementary to the sense strand of exonic regions in a gene of interest can select not only the genomic DNA, but also any RNA transcripts of these regions. By using such a driver population to select both the genomic DNA and RNA transcripts, the practitioner generates a pool of enriched DNA and RNA for the same genomic region, which can be used to simultaneously evaluate both the gene sequence and the expression level of the gene. In certain aspects, the sequences generated from the genomic DNA in the pool is distinguished from the RNA-derived sequences by virtue of the different characteristics of genomic and transcript nucleic acids, e.g., the presence or absence of intronic sequence, polyA tail, 3'- and 5'-untranslated regions, etc. Further, the amount of genomic sequence generated from the DNA/RNA mixture can serve as a baseline to evaluate the level of expression of the gene, i.e., for a given exon the ratio of DNA-derived sequence to RNA-derived sequence is a measure of the expression level of the gene. Essentially, any pool of fragments having sequences that do not occur or are extremely infrequent in non-target fragments can be selected using a driver-based methodology, as long as the sequences can hybridize in a stable and specific manner to the driver molecules.

In certain preferred embodiments, nucleic acids in a driver population comprise a tag or other moiety to facilitate selection and/or retention of the tester-driver hybrid complexes. For example, a biotin tag can be linked to nucleic acids in the driver population so that tester-driver hybrid complexes can be captured by binding to a binding partner for biotin, e.g., streptavidin, which is bound to a solid surface, e.g., a bead or column. In other embodiments, the driver population is attached to a solid surface prior to the capture reaction, e.g. via a tag or, optionally, can be synthesized directly on a surface. In yet further embodiments, the driver fragments are linked to oligonucleotides that are complementary to oligonucleotides on a solid surface, similar to the capture-hook oligonucleotides discussed elsewhere herein. Such a solid surface can be, for example, a microarray, column, or bead. In certain preferred embodiments, the solid surface is a magnetic bead, which allows capture of driver-containing complexes using a magnet or magnetic device. The bound tester-driver complexes are separated from the unbound nucleic acids, e.g., by washing, and can be eluted from the surface for further processing or analysis. Alternatively or additionally, the unbound nucleic acids that were removed from the bound complexes may be subsequently processed or analyzed. In some embodiments, the driver population is subjected to amplification prior to tester-driver hybridization and enrichment. In preferred embodiments, the tester population is not amplified before the tester-driver hybridization and enrichment. Tags that allow the capture and, therefore, the separation of tester molecules that comprise sequence complementary to the driver from tester molecules that do not, are well known in the art and preferred tags include affinity tags, such as biotin and avidin, or a derivative thereof (e.g., streptavidin, etc.). Specific examples of reactive functionalities for associating an affinity tag to a binding partner are provided in Table I, herein. In some embodiments, the captured tester molecules are fully single-stranded, but in some preferred embodiments they are substantially double-stranded with only the ends single-stranded and available to hybridization to a driver molecule. This maintains the native composition of both strands of the tester molecule, while allowing hybridization-based capture by driver molecules complementary to terminal portions of the tester molecules.

Where the tester and/or driver populations are provided as double-stranded nucleic acids, they are combined and typically denatured to allow hybridization of tester to driver. Various strategies can be used to facilitate annealing of a driver population, e.g., denaturation of the tester population prior to annealing the driver population, or use of modified nucleotides within the driver population including, but not limited to, tighter binding O-methyl nucleotides, locked nucleic acids (LNAs), peptide nucleic acids (PNAs), and others known to those of skill in the art. For example, where the tester is double-stranded, the driver can be provided in single-stranded form and, optionally, can comprise nucleotides that facilitate strand invasion and/or have a tighter hybridization to a single strand of the tester nucleic acid than the complementary strand has. In some embodiments, amplification of the driver population (prior to combining the driver and tester populations) comprises incorporation of such tighter-hybridizing nuclotides or nucleotide analogs into the driver amplicons, or, alternatively, chemical synthesis of such driver molecules.

The strand invasion can also be facilitated by addition of a strand invasion protein, such as RecA or RecT protein. RecA is an *E. coli* DNA-binding protein whose primary role is to initiate strand exchange during homologous recombination. RecA promotes invasion of a RecA-coated 3'-terminal single-stranded nucleic acid into a duplex DNA molecule having a strand complementary to the RecA-coated strand. In the cell, this allows a chromosome to be used as a template for strand repair of another chromosome that is its homolog. Similarly, RecT is another *E. coli* protein involved in homologous recombination. RecT binds both single- and double-stranded DNA and is believed to promote strand invasion of a single-stranded DNA into a homologous duplex molecule. Other proteins known to promote strand-invasion include, but are not limited to yeast Rad51/Rad52 proteins, human splicing factor PSF, and protein beta of coliphage lambda. These strand-invasion activities of these proteins can be used to enhance the binding of single-stranded driver molecules to duplex tester molecules, and more information on them is replete in the literature, e.g., in Noirot, et al. (1998) J. Biol. Chem. 273(20): 12274-80); Bi, et al. (2004) Proc. Natl. Acad. Sci. USA 101(26):9568-72; Akhmedov, et al. (2000) Nuc. Ac. Res. 28(16):3022-30; Xu, et al. (2002) J. Biol. Chem. 277(16): 14321-14328; and Rybalchenko, et al. (2004) Proc. Natl. Acad. Sci. USA 101(49):17056-60, all of which are incorporated herein by reference in their entireties for all purposes. In certain embodiments, following capture and isolation the enriched nucleic acids can be released from the recombinase-coated driver molecule by removal of a necessary cofactor, e.g., ATP in the case of RecA.

Other types of proteins that can be used to promote binding of driver molecules to tester molecules, especially where the driver molecules are single-stranded and the tester molecules are double-stranded, include helicases and single-stranded DNA binding proteins (SSBs). Helicases are a class of enzymes that unwind double-stranded DNA. Using a helicase, or related protein, can unwind the double-stranded region of a duplex molecule, e.g., in a double-stranded fragment capped by stem-loop adapters), thereby increasing the accessibility of a target region in a tester molecule to a driver molecule complementary thereto. Single-stranded DNA binding proteins can help to keep a duplex region unwound, further increasing accessibility of the target region.

In certain preferred embodiments, the driver comprises modified nucleotides that increase annealing to the target region, which can be beneficial where the driver must displace SSB proteins in order to bind. For example, modified nucleotides within the driver molecules can increase the melting temperature of the annealed driver/tester complex. Some examples are locked-nucleic acids (LNAs), protein-nucleic acids (PNAs), 2'-O-methyl nucleotides, etc. PNAs and LNAs, for example, have been used to promote strand invasion of a single-stranded DNA into a segment of double-stranded DNA. This strategy makes the interaction with the single-stranded DNA more favorable or stable than the interaction with the complementary strand in the double-stranded DNA. As such, hybridization with a driver molecule will be more likely to result in annealing and pull-down of the desired tester molecules containing the target sequence.

In some embodiments, polymerase extension is used to further stabilize the tester/driver complex to increase the efficiency of the capture reaction. For example, the strands of a double-stranded tester molecule that comprises a stem-loop adapter at both ends can be separated by annealing a primer to one of the loop regions and extending the primer using a polymerase. The primer extension reaction preferably only extends the primer half the way around the template, i.e., to the second adapter sequence. The extension reaction can proceed only partway to the second adapter, as long as the target sequence complementary to the driver molecule is rendered single-stranded and therefore accessible for hybridization. As such, the strand (or part of the strand) of the duplex portion that is processed by the polymerase will become double-stranded as the complementary strand in the tester molecule is displaced. It is the displaced strand that is the single-stranded portion to which the driver will anneal in order to capture the tester molecule. In some preferred embodiments, a pause or stop site is engineered into an adapter opposite where the primer is bound to ensure that the polymerase processes only a single strand of the double-stranded portion during the extension reaction, i.e., that it does not continue around the opposite adapter and begin processing the other strand of the duplex. Such a pause or stop site can be a modified nucleotide (e.g., linked to a bulky group, abasic site, a base requiring a non-canonical base that is not in the reaction mixture to be incorporated in the nascent strand, etc.) or bound agent that blocks further progression of the polymerase enzyme, e.g., a modified primer that cannot be displaced by the polymerase. Preferably, the pause site is reversible, to allow progression of the same or a different polymerase enzyme in a subsequent reaction, e.g., for sequencing-by-synthesis. In some cases, the pause is chemically induced, e.g., by addition of agents that cause the polymerase to pause. For example, certain divalent cations, e.g., $Ca^{2+}$, do not support polymerization, so addition of such cations (and/or removal of those that do support polymerization, e.g., with a chelating agent) can provide a temporary pause that is reversible by addition of the needed cations and/or the removal of those that inhibit polymerization. In other embodiments, the polymerase used for the initial extension is sensitive to the pause site, but a different polymerase capable of bypassing the pause site is used for any subsequent polymerase-dependent reactions, e.g., amplification or sequencing. Various methods for including pause or stop sites into a nucleic acid molecule are described in detail in U.S. Pat. Nos. 7,901,889, 8,153,375, and 8,143,030, the disclosures of which are incorporated herein by reference in their entireties for all purposes.

In preferred embodiments, the tester population is a population of double-stranded fragments to which stem-loop (a.k.a., "hairpin") adapters have been added at both termini, thereby capping the ends. These tester nucleic acids therefore comprise a double-stranded tester fragment in a topologically closed construct, such that denaturation or unwinding of the double-stranded portion generates a single-stranded circular tester molecule. As described elsewhere herein, these molecules are beneficially used as nucleic acid sequencing templates for use in polymerase-mediated, sequencing-by-synthesis methods because they allow both strands to be sequenced repeatedly as the polymerase translocates around the topologically closed template performing "rolling-circle" synthesis. The nascent strand so generated comprises complements to both strands of the original double-stranded fragment, and where the synthesis can be monitored in real-time, the sequence of nucleotide incorporation events provides, by complementarity, the nucleotide sequence of both strands of the original tester nucleic acid. For more information on these types of sequencing templates, see, e.g., U.S. Pat. No. 8,153,375, which is incorporated herein by reference in its entirety for all purposes.

Further, linking the two strands of a target nucleic acid has the added benefit of locking the two strands together since even upon strand separation the strands remain linked. The driver nucleic acids bind within the tester fragments to provide select these fragments from other fragments in the mixture, and such driver nucleic acids can be used as probe sequences within capture-hook oligonucleotides, as described in detail elsewhere herein. It is also contemplated that the driver nucleic acids can be used as primers for subsequent analysis, e.g., amplification and/or polymerase-mediated sequencing-by-synthesis in which the target nucleic acids serve as the template nucleic acids.

In yet further embodiments, a tester nucleic acid capped by hairpin adapters is subjected to rolling-circle replication to generate a concatemer comprising repeating complementary copies of the adapter-linked fragment. Multiple driver nucleic acids can hybridize to this concatemer, since each concatemer will have multiple copies of the sequence to which the driver nucleic acids are complementary. Each driver nucleic acid bound provides an additional affinity tag or other selectable moiety that can be used to purify the rolling-circle complex. The tester fragments that are not bound by the driver molecules are removed to leave only the selected tester fragments, which are now enriched in the population. Optionally, the nascent, concatemeric strands can be degraded to recover only the original tester nucleic acids fragment capped by the hairpin adapters. As noted above, various strategies can be used to enhance binding of driver to tester, e.g., driver molecules with enhanced binding, use of strand-exchange and/or single-stranded binding proteins, and the like.

Target sequences captured in these methods can be used directly in further analytical reactions, e.g., sequencing reactions, or can be subjected to further manipulations such as amplification, cloning, and the like. For example, where the fragments captured are single-stranded nucleic acids, a complementary strand can be generated, e.g., by random primed synthesis or using specific primers that bind to adapters at the ends of the fragments. Such adapters can be added before or after capture, but are preferably added prior to denaturation and sequence capture.

TABLE I

| Reactive functionality | Complementary group | The resulting bond |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides/imides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |

TABLE I-continued

| Reactive functionality | Complementary group | The resulting bond |
|---|---|---|
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols (amines) | thioethers (alkyl amines) |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonyl halides | amines/anilines | sulfonamides |

V. Targeted Fragmentation Using Zorro-LNA Oligonucleotides

In certain aspects of the invention, a fragmentation strategy is dependent upon the strand-invading properties of "Zorro-LNA" oligonucleotides. A Zorro-LNA is a z-shaped LNA (locked nucleic acid) construct whose ends have the potential to specifically bind to opposite strands of a DNA duplex. Locked nucleic acids, or LNAs, have stronger binding to single-stranded nucleic acids than do oligonucleotides comprising only canonical nucleotides. As such, strand invasion reaction can be facilitated by using an LNA oligonucleotide rather than a canonical oligonucleotide. Zorro-LNAs can bind within a duplex, with one end hybridized to one strand, and the other end hybridized to the other strand, thereby separating the duplex and forming "bubble" within which the Zorro-LNA is positioned. Typically, the central portion of as Zorro-LNA is a linker portion connecting the two ends; however, some Zorro-LNAs comprise two oligos that are hybridized together in the central portion to leave two single-strand overhangs at the ends that will hybridize to the two strands of the duplex. They can be designed to flank a target region by using end sequences that are homologous to known sequences outside of but proximal to the target region. Longer homologous sequences are preferred, since they are less likely to find other complements within a sample. With the Zorro-LNAs bound to the flanking regions, the single-stranded bubbles formed are susceptible to cleavage by a single-strand specific endonuclease, e.g., Si nuclease. The nucleic acid is cut, thereby creating a fragment comprising the target region. Optional size selection can follow, as well as additional manipulations (e.g., adapter ligation, nuclease treatment, etc.) and analyses (e.g., sequencing, cloning, amplification, etc.). The Zorro-LNAs can be specific for the target region, or can be nonspecific to randomly digest the sample nucleic acid. In some embodiments, a combination of specific and nonspecific Zorro-LNAs are used, where the nonspecific Zorro-LNAs are selected so that they will not cleave within the target region and/or create overhang sequences that match those of the specific Zorro-LNAs that bind to the flanking regions around the target region. For more information on Zorro-LNAs, see Zaghloul, et al. (2011) Nuc. Ac. Res. 39(3): 1142-54, which is incorporated herein by reference in its entirety for all purposes.

VI. Applications

Many research and diagnostic assays require sequence information for a particular locus of interest or just a few loci in a large number of individual samples. Sequencing a full genome, especially a large genome like the human genome, for each of multiple samples (e.g., from patients, subjects from case-control studies, etc.) in order to sequence the locus of interest is not economically feasible. Therefore, an efficient and cost-effective targeting method for enrichment of the region of interest in a complex genome is desirable and is provided by the instant application. It is also particularly challenging to provide enriched targeted templates for sequencing that comprise native DNA for epigenetic study since many reported target enrichment methods require some DNA amplification or cloning before, during, or after the enrichment (hybrid capture, PCR amplification, molecular-inversion-probes selection, etc.). In some cases, the goal of a study is the identification of rare mutations or counting the number of repeats in a repeat region of interest, and since PCR amplification is known to introduce errors into the resulting amplicons and has difficulty producing amplicons from highly repetitive nucleic acids, it can complicate the identification of true sequences in the original sample.

Isolation of molecules containing a region of interest that exists in low concentrations in a highly complex sample is challenging, and often there is not enough enriched nucleic acid to perform the additional analyses, e.g., sequencing, without PCR amplification. The instant invention provides an enrichment method for a single genomic region or locus of interest from a complex sample, e.g. a whole genome sample, without any amplification. In preferred embodiments, the enriched templates are native DNA that can be used for mutation detection, allelic difference determination, and direct methylation analysis by SMRT® sequencing, e.g., as further described in U.S. Patent Publication No. 2011/0183320, incorporated herein by reference in its entirety for all purposes. This enrichment methodology, termed the TTPS enrichment method (Targeted Template Protection & Selection), was applied to various different loci, including the FMR1 locus from human gDNA samples, and it exhibited good performance as measured by parameters such as sensitivity, specificity, sequence coverage, reproducibility, ease of use, cost, the amount of DNA and methylation detection.

The enriched compositions described herein are particularly useful in nucleic acid sequencing reactions, e.g., polymerase-mediated, template-dependent synthesis of nucleic acids, which can be observed using real-time techniques for a variety of desired goals, including in particular, determination of information about the template sequence. A number of methods have been proposed for determination of sequence information using incorporation of fluorescent or fluorogenic nucleotides into the synthesized strand by a DNA or other polymerase, and the compositions of the invention are applicable to these methods. While several of these methods employ iterative steps of nucleotide introduction, washing, optical interrogation, and label removal, preferred uses of these compositions utilize "real-time" determination of incorporation. Such methods are described in detail in, for example, U.S. Pat. Nos. 7,056,661, 7,052,847, 7,033,764 and 7,056,676, the full disclosures of which are incorporated herein by reference in their entirety for all purposes.

Briefly, such methods observe an immobilized polymerase/template/primer complex as it incorporates labeled nucleotide analogs. Using optical techniques that illuminate small volumes around the complex with excitation radiation, e.g., TIRF methods, optical confinements like Zero Mode Waveguides (ZMWs) (See, U.S. Pat. Nos. 6,917,726, 7,013,054, 7,181,122, 7,292,742 and 7,170,050 and 7,302,146), and the like, one can identify incorporation events based upon the optical signature of their associated fluorophore, as compared to non-incorporated, randomly diffusing labeled nucleotide analogs. By providing each different type of nucleotide with a distinguishable fluorescent label, e.g., having a distinguishable emission spectrum, one can identify each base as it is incorporated, and consequently read out the sequence of the template as the nascent strand is created against it. By utilizing the compositions of the invention, negative impacts of the fluorescent label on the polymerase or other components of the labeled complex (See, e.g., published U.S. Patent Application No. 2007/0161017), can be reduced or eliminated by moving the label portion away from the reactant portion and consequently, the active site of the enzyme, or other sensitive portions of the complex.

In some embodiments, the methods herein are used to enrich target nucleic acids from complex samples, e.g., metagenomic samples. Metagenomic samples include, but are not limited to, environmental samples such as soil, water, and air; agricultural samples such as produce and meat; industrial samples such as generated waste; and biological samples such as forensic collections and bacterial mixtures. The methods are especially beneficial where the target nucleic acids are a minority species in a mixture of nucleic acids. For example, where the sample is blood collected from an infected human individual the enrichment can separate human nucleic acids from "non-human" nucleic acids that may be present, e.g., by capturing the known human nucleic acids and separating them from the non-human nucleic acids. The isolated non-human nucleic acids can be subsequently analyzed to determine their source, e.g., one or more pathogenic organisms. Similarly, where it is desired to determine whether a sample comprises a particular minority species, the minority species can be specifically captured, isolated from the rest of the nucleic acids in the sample, and subsequently detected.

Enriched nucleic acid mixtures are useful for many applications apart from sequence analysis, as well as those that include, but go beyond, simple sequence analysis. Certain nonlimiting examples include cloning of a target region, amplification of a target region, separation of nucleic acids from different sources in a complex sample, and the like. Further, such enriched samples are desired for identifying genetic determinants of disease or other disorders, e.g., through prognostic or diagnostic applications. Such targeted biomedical applications are particularly useful for enriching for a gene or genes known to provide a biological basis for a genetic disorder, whether it is a susceptibility or a resistance phenotype, preferably without needing to clone the gene or genes. These gene or genes, once identified and their roles in the disorder understood, can also be used in theranostic applications, for example, in the development of small-molecule-based (e.g., drugs, pro-drugs, etc.) and nucleic-acid-based therapies (e.g., RNAi, antisense oligonucleotides, etc.). Other uses for the enriched nucleic acid mixtures provided by the instant invention will be recognized by those of ordinary skill in the art, as many of the applications are standard in the field of biomedical application, but up until now have suffered from the inability to enrich and analyze large and/or modified nucleic acid fragments, so much genetic information, such as haplotype alleles and base modification data, could not be studied. The methods herein provide new and useful methods for such large and/or modified nucleic acids, thereby generating new possibilities for targeted biomedical applications. Additional compositions, methods, and systems that can be used with those provided herein, or that will benefit from those provided herein, include those described in the following publications, all of which are incorporated herein by reference in their entireties for all purposes: U.S. Pat. Nos. 7,476,503, 7,476,504, 7,935,310, 7,995,202, 8,193,123, 7,715,001, 7,901,889, 7,906,284, 8,003,330, 8,236,499, 8,153,375, and 8,247,216; U.S. Patent Publication Nos. 2010/0221716, 2010/0323912, 2010/0311061, 2012/0071359 and 2012/0115736; and U.S. application Ser. No. 13/363,066 (filed Jan. 31, 2012), Ser. No. 13/427,725 (filed Mar. 22, 2012), Ser. No. 13/429,019 (filed Mar. 23, 2012), Ser. No. 61/617,999 (filed Mar. 30, 2012), and Ser. No. 61/658,747 (filed Jun. 12, 2012).

The methods herein are useful for enriching a nucleic reaction mixture for genomic regions comprising repetitive sequences, such as triplet repeats associated with genetic disorders including, but not limited to, fragile X syndrome, fragile X-associated tremor/ataxia syndrome (FXTAS), amyotrophic lateral sclerosis (ALS), autism, various cancers, myotonic dystrophy, ataxias, epilepsy, Huntington's disease, and others known in the medical field, many of which are neuromuscular or spectrum disorders. The repeat regions can occur in coding and/or noncoding regions, and the repeats vary in size in different regions, e.g., they can be trinucleotide repeats, tetranucleotide repeats, hexanucleotide repeats, etc. The ability to select an entire repeat region, including some flanking sequence on each side, allows the researcher to analyze the entire region as a whole. Such analysis can include determining the number of repeats, detection of modified bases, and identification of interruptions in the repeat region. Yet further, any interruptions identified can be mapped to a specific homolog, e.g., the maternally-derived or paternally-derived chromosome. This has important carrier information for maternal carriers who pass on expanded repeats much less frequently if they have an interruption, and this knowledge can be used in pre-conception genetic screening to compute probabilities that an expanded repeat region will be transmitted to an offspring. Further, since many repeat expansion disorders have a later age-of-onset, complete sequence and modification information can also inform with regards to a carrier's risk of developing the disorder, predict age-of-onset and severity, and may also be used in determining an appropriate treatment plan to prevent, delay, or reduce the severity of the disorder. An individual tested typically either has a family history of the disorder or is displaying signs or symptoms of the disorder, and the results of the testing are useful for determining whether early intervention is appropriate at a clinical level. Such an individual can be, for example, a newborn baby, a child, or an adult.

A haplotype for the entire region is generated that includes not only sequence information, but also base modification information. This haplotype will likely be predictive of efficacy of various potential treatments for the disorder. For example, pharmaceutical companies are developing drugs for treating individuals with fragile X syndrome, ALS, and other repeat expansion disorders. In some instances, the same repeat expansion can underlie multiple clinically distinct disorders. For example, ALS and frontotemporal dementia (FTD) both exhibit a strong association with a repeat expansion of a hexanucleotide sequence (GGGGCC) at a specific locus (9p21) on chromosome 21. The ability to specifically enrich this region from whole genomic DNA and analyze it in a long-read sequencing strategy will provide a means to predict susceptibility to or aid in the diagnosis of these disorders. The complete haplotype information along with past drug response data can be used to predict the efficacy of the drug treatment in future patients having the same or a similar haplotype for the repeat region. As such, the haplotype is not only predictive of susceptibility to the disorder, but also efficacy of various treatment options.

Yet further, the methods herein can be used for enriching a nucleic acid sample for multiple different regions, e.g., corresponding to multiple different genes within a metabolic pathway of interest. As noted elsewhere herein, where sources are to be combined prior to analysis (e.g., "multiplexed"), barcodes can be added so the data from the subsequent analysis can be parsed and linked back to the original sources. In some such embodiments, target regions represent a set of genes involved in a biological pathway of interest, e.g., oncogenesis. Adapters specific for each target region comprise barcodes, and these barcodes can provide different types of source information. For example, they can identify the particular target gene region, the tissue type from which the nucleic acid was isolated, or the individual from which the nucleic acid was obtained. In some embodiments, the individual is not identified, but the disease state of the individual is, which is useful for performing multiplexed case-control studies in which nucleic acids from cases and controls are pooled prior to analysis. Since the biological basis for many disorders involves many different genes, it is desirable to multiplex the analysis of a set of genes (a "gene panel") associated with a given disease or disorder. In these applications, each different gene can be provided a different barcode, and/or the barcodes can instead distinguish between tissue sources, patients, disease status, and the like. Yet further, both genomic DNA and mRNA can be isolated and subjected to analysis, where both the genomic sequence information as well as the full-length transcript and/or splice-isoform data generated can better inform the clinician about the disease state of the patient. In such applications a barcode is helpful to distinguish between genomic nucleic acids and transcript sequences, since they can be identical in sequence, at least in exonic regions.

Mosaicism in an individual can also be studied using the methods herein. Mosaicism is a condition in which two or more genetically distinct cell populations exist in an organism. It can be caused by unequal distribution of genetic material during mitosis such that the daughter cells produced are not identical. Those daughter cells replicate to create populations of cells that are genetically distinct from one another. This phenomenon is commonly observed in highly repetitive regions of a genome, since these regions are often not replicated correctly during cell division. As such, daughter cells can have more or fewer repeats than the parental cells, and they in turn can divide to produce cells that have further differences in copy number. Mosaicism can present in a tissue-specific way, such that a first tissue type in an organism can have a different number of repeats than a second tissue type in the same organism, e.g., where the first and second tissue types are from first and second progenitor cells that differed in the number of repeats each contained. Further, the type of tissue in which a deleterious repeat polymorphism (e.g., repeat expansion) occurs is key to whether the individual will present with a genetic disorder, and the specific type of disorder to which they are potentially susceptible. For example, a repeat expansion in brain tissues may cause a neurological disorder, while one in breast tissue causes breast cancer. The ability to target a repeat region from a particular tissue, enrich for that repeat region, and perform single-molecule sequencing on the region allows the researcher to determine the genotype for that tissue, and that information can be used in prognostic and diagnostic applications for a genetic disorder associated with the repeat region. Comparison of the repeat region from one tissue (e.g., skin) to the repeat region from another tissue (e.g., blood) can also be informative, providing data for which tissue types have expanded repeat regions, and how they can be differently expanded depending on the tissue in which they are being replicated. This is valuable information in the study of repeat-related disorders, and contributes to determination of a genetic cause of a disorder and development of genetic screening tests, and potentially provides insight into how such a disorder can be prevented and/or treated.

VII. Kits

The compositions of the invention are optionally provided in kit form, including various components of an overall analysis in combination with instructions for carrying out the desired analysis. In particular, such kits typically include the compositions of the invention (e.g., adapters, restriction endonucleases, exonucleases, etc.), including at least one, but preferably multiple types of labeled nucleotide analogs of the invention, e.g., A, T, G and C analogs. Each of the different types of labeled nucleotide analogs in the kit will typically comprise a distinguishable labeling group, as set forth above. In addition to the analog compositions, the kits will optionally include one or more components of a polymerase complex, including, for example polymerase enzymes, such as any of a number of different types of strand displacing polymerase enzymes. Examples of such polymerases include, e.g., phi29 derived polymerases, and the polymerase enzymes described in, e.g., Published International Patent Application Nos. WO 2007/075987, WO 2007/075873 and WO 2007/076057, the full disclosures of which are incorporated herein by reference in their entirety for all purposes.

Additional reaction components are also optionally included in such kits, such as buffers, salts, universal priming sequences for initiation of synthesis, and the like. In addition, in particularly preferred aspects, the kits of the invention will typically include a reaction substrate that includes reaction regions for carrying out and observing the synthesis reactions for identification of sequence information. Such substrates include, e.g., multi-well micro or nano plates, as well as arrayed substrates, e.g., planar transparent arrays that include discrete reaction regions defined by, e.g., structural, chemical or other means. For example, patterned arrays of complexes may be provided disposed upon planar transparent substrates for observation. Alternatively and preferably, the substrate component comprises an array or arrays of optically confined structures like zero mode waveguides. Examples of arrays of zero mode waveguides are described in, e.g., U.S. Pat. No. 7,170,050, the full disclosure of which is incorporated herein by reference in its entirety for all purposes.

Examples

1. Enrichment of Specific Regions of Human Mitochondrial DNA

Human liver DNA, comprising both genomic DNA and circular mitochondrial DNA, was subjected to an enrichment procedure intended to target a 1023 bp region in mitochondrial DNA (16 kb) between HV1 and HV2 ("HV" stands for "hypervariable). Two methods were used to enrich a sample for this region. The first used type II restriction enzymes and the second used type IIs restriction enzymes. In the first case, after determining recognition sites for type II restriction endonucleases in the mitochondrial DNA region of interest, BamHI and PvuII were used to fragment the liver DNA sample. This digestion produces many fragments, including a 4963 bp fragment from the mitochondrial genome comprising the HV1-1023 bp-HV2 region flanked by 1717 bases on one end and 2223 bases on the other end. The BamHI cut site has a four-base overhang, and the PvuII cut site is blunt-ended. Two different stem-loop adapters were linked to the ends of the fragments, one having a blunt end for ligation to the blunt ends created by the PvuII enzyme, and one having overhangs compatible with the overhangs generated by BamHI. As such, the target fragment created by the ligation reaction comprised the "PvuII adapter" at one end and the "BamHI adapter" at the other end.

In the second case, after determining recognition sites for type IIs restriction endonucleases in the mitochondrial DNA region of interest, SfaNI was selected to generate ~2.9 million fragments averaging ~1 kb in size, including a 1464 bp fragment comprising the HV1-1023 bp-HV2 region flanked by 160 bases on one end and 281 bases on the other end. There are 23 SfaNI cleavage sites in the mitochondrial DNA. SfaNI-cleavage results in random four-base overhangs at the ends of the fragments generated. Two stem-loop adapters with defined four-base overhangs (5'-TATA and 5'-TCCA) were ligated to the fragments. This ligation was expected to generate only about 50 different fragments having both adapters, one at each end.

Following ligation of stem-loop adapters to both the first pool of fragments generated using the type II restriction enzymes and the second pool of fragments generated using the type IIs restriction enzymes, the two mixtures were treated with various endonucleases that do not cleave human mitochondrial DNA, e.g., SalI, MluI, XmaI, and NruI, but may cleave some of the fragments with adapters linked thereto that originated from the genomic DNA. The mixtures were further treated with ExoIII and ExoVII to digest all fragments having a susceptible terminus, e.g., one that is not capped with a stem-loop adapter. Following the nuclease treatment, the two mixtures were subjected to a purification procedure using an Agencourt® AMPure®system (Beckman Coulter, Brea, Calif.) to remove small fragments, free adapters, and adapter-dimers, were any formed. As a further experiment, fragments generated with the type IIs restriction enzymes were also ligated to stem-loop adapters, but subsequently digested with only the exonucleases to determine whether the addition of the endonuclease to the final digest provided for further enrichment of the 1464 bp target fragment; the resulting mixture was subjected to the same purification procedure. The three resulting purified mixtures, as well as a control pool of liver DNA fragments that were not enriched for the target region (but were ligated to adapters, exposed to exonucleases, and purified), were subjected to single-molecule, real-time, sequencing reactions.

Figure 5:
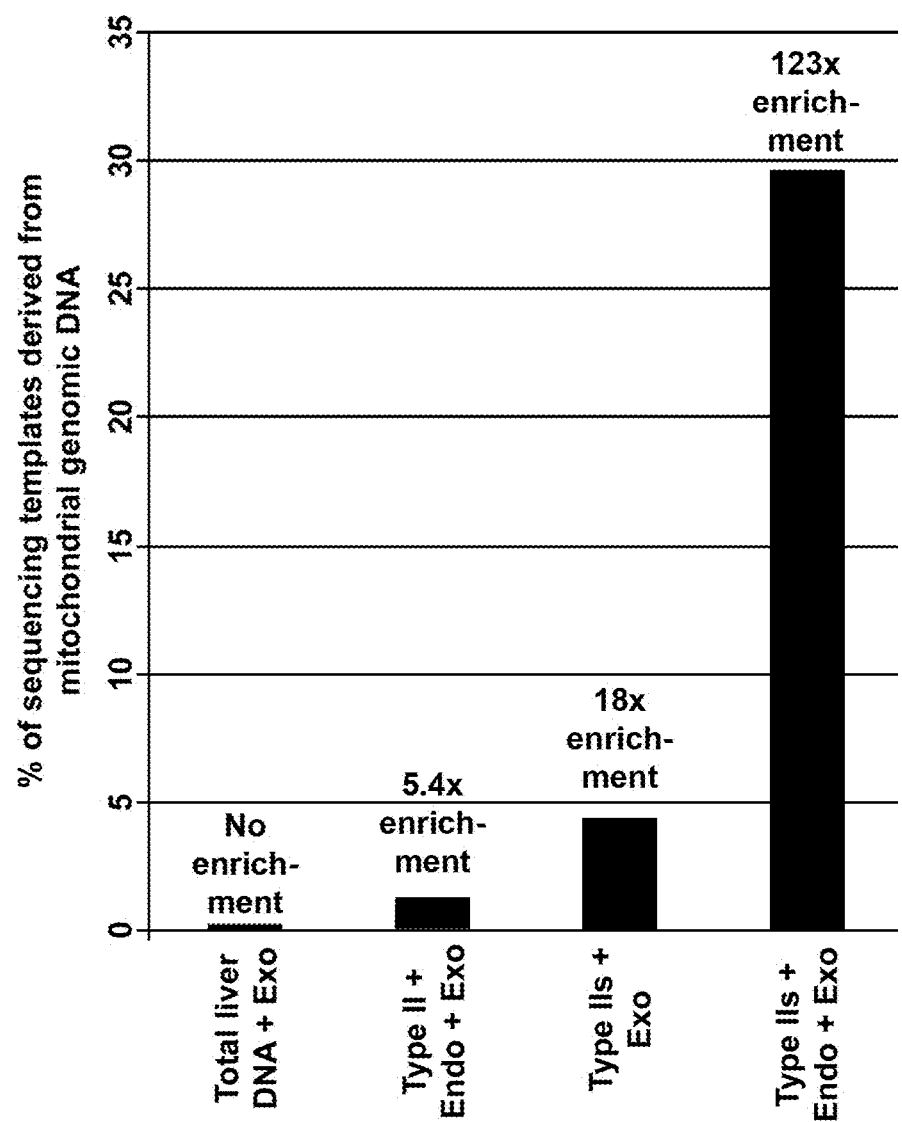
FIG. 5 provides a graphical representation of sequencing data generated from human liver DNA.
Figure 6:
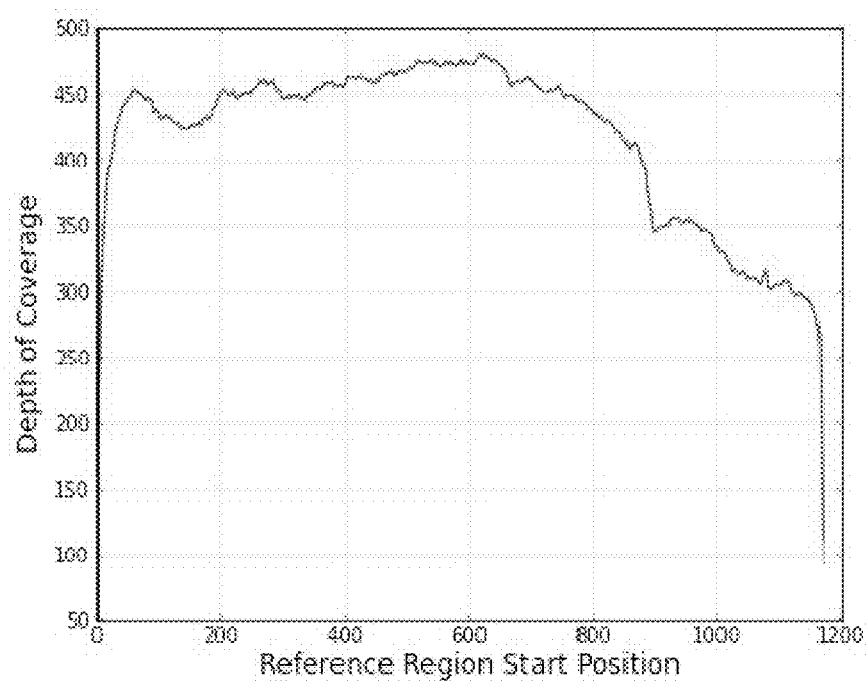
FIG. 6 illustrates the depth of coverage for the sequencing data from a nucleic acid sample enriched for human mitochondrial DNA.

The enrichment procedure utilizing the type II restriction endonucleases resulted in a nucleic acid sample with ~5.4-fold enrichment for the 4963 bp target region. Approximately 1.25% of the resulting sequence reads were from this region. The enrichment procedure utilizing the type IIs restriction endonucleases, stem-loop adapter ligation, and exonuclease digestion (but no further endonuclease digestion) resulted in a mixture of fragments having ~18-fold enrichment for the 1464 bp target region and >4% of the resulting sequence reads were from this region. Finally, the enrichment procedure utilizing the type IIs restriction endonucleases, stem-loop adapter ligation, and a combination of endonuclease and exonuclease digestion resulted in a mixture of fragments having ~123-fold enrichment for the 1464 bp region target fragment. Approximately 30% of the resulting sequence reads were from this region, and these reads provided ~400-fold coverage of this region. By comparison, with no enrichment only about 0.25% of the sequence reads generated from the liver DNA sample were sequence reads from the mitochondrial target region. FIG. 5 provides a graphical representation of these data. Fold enrichment was calculated by comparing the percentage of sequence reads generated from mitochondrial DNA in the non-enriched sample to the percentage of sequence reads generated from mitochondrial DNA in the enriched sample. For example, for the enrichment procedure utilizing the type IIs restriction endonucleases, stem-loop adapter ligation, and a combination of endonuclease and exonuclease digestion, single-molecule sequencing of the enriched sample provided 670 reads from mitochondrial DNA and 1,597 reads from non-mitochondrial DNA, which is 29.6%. In contrast, the non-enriched sample provided only 67 out of 27,544 reads from mitochondrial DNA, which is 0.24%. The ratio of the percent of mitochondrial-DNA reads for the enriched sample over the non-enriched sample, 29.6/0.24=123.33 fold enrichment. The depth of coverage for the sequencing data from the enriched sample is illustrated in FIG. 6.

All the sequencing templates were generated from nanogram amounts of isolated liver DNA. For example, 30 ng of human liver DNA was used to generate the non-enriched control templates; 612 ng was used to generate the mixture comprising the 4963 bp target fragment; and 114 ng was used to generate the mixture comprising the 1464 bp target fragment.

2. Enrichment of Entire Mitochondrial Genome

Human liver DNA, comprising both genomic DNA and circular mitochondrial DNA, was subjected to an enrichment procedure to target the entire human mitochondrial genome. In this procedure, whole human DNA (genomic and mitochondrial DNA) was subjected to digestion with PvuII and HpaI (both of which cleave to leave a blunt end), and then ligated to a blunt-ended stem-loop adapter to generate a pool of genomic and mitochondrial DNA fragments having a blunt-ended adapter linked to both ends. Based on restriction endonuclease mapping, this digestion was expected to generate four specific fragments from the mitochondrial DNA with fragment sizes 3041, 4323, 2392, and 6813. These four fragments covered the entire human mitochondrial genome. Following ligation, a second endonuclease reaction was performed in which the fragments were treated with seven restriction endonucleases that do not have recognition sequences in mitochondrial DNA, e.g., BglII, XmaI, SalI, DrdI, MluI, NruI, and PvuI. As such, only genomic DNA fragments were cleaved to leave exonuclease-susceptible ends. Subsequent exonuclease treatment digested any fragments that did not ligate at both ends to a stem-loop adapter, and any fragments that were cleaved during the second endonuclease reaction. Following the nuclease treatment, the sample was subjected to a purification procedure using an Agencourt® AMPure® system (Beckman Coulter, Brea, Calif.) and subsequently subjected to single-molecule, real-time sequencing.

Enrichment of an entire mitochondrial genome from a sample that includes both genomic and mitochondrial DNA was also performed using type IIs restriction enzymes. BsmBI leaves a random four-base overhang, and BspQI leaves a random three-base overhang. These two enzymes were used to fragment the sample nucleic acids, and the resulting fragments were exposed to T4 ligase in the presence of two stem-loop adapters having specific four-base or three-base overhangs that are complementary to the overhangs expected for the mitochondrial fragments. This digestion resulted in ~915,000 genomic fragments lacking an adapter on at least one end, ~670 genomic fragments having an adapter at both ends, and four mitochondrial fragments having fragment sizes 3471, 4075, 7320, and 1703 and an adapter at both ends. The mixture was subjected to endonuclease digestion with enzymes that do not cleave mitochondrial DNA (e.g., BglII, XmaI, SalI, DrdI, MluI, NruI, and PvuI), but do cleave any of the genomic fragments having the recognition sequence. Exonuclease treatment degraded all fragments that have a susceptible terminus, whether because no adapter ligated to it, or due to the endonuclease digestion following ligation. Following the nuclease treatment, the sample was subjected to a purification procedure using an Agencourt® AMPure® system (Beckman Coulter, Brea, Calif.) and subsequently subjected to single-molecule, real-time sequencing.

3. Targeted Human P16 Promoter Enrichment

The promoter for the P16 gene is located on human chromosome 9, from position 21964038 to position 21970038 (the P16 gene is mapped at positions 21957751-21964038). Human genomic DNA isolated from HeLa cells was digested with HgaI to produce genomic fragments having random five-base overhangs. This set of fragments included a 1089 bp fragment extending from positions 21965023 to 21966112, and which comprises the P16 promoter region. This digestion generated ~2.9 million fragments averaging 1 kb in size. Two different stem-loop adapters having defined five-base overhangs (5'-CTCGC and 5'-CTCAC) were ligated to these fragments, and it was predicted that only three of these fragments would have complementary overhangs such that the first adapter was ligated to one end and the second adapter was ligated to the other end. Subsequent treatment with some of the ~106 restriction endonucleases that do not cleave the 1089 bp fragment of interest and exonucleases (ExoIII and ExoVII) degraded fragments that were cleaved by the endonucleases and/or that were not capped at both ends by adapters. Following the nuclease treatment, the sample was subjected to a purification procedure using an Agencourt® AMPure® system (Beckman Coulter, Brea, Calif.) and subsequently subjected to single-molecule, real-time sequencing.

4. Enrichment and Sequencing of D-Loop Region on Agu Mitochondria from Pig Genomic DNA Sample A known ~1.3 kb region of mitochondrial DNA, the D-loop, was enriched from a genomic DNA sample from the Okinawan native pig, the agu. The agu genome contains about three billion base pairs, and the agu mitochondrial genome contains about 16,000 base pairs. Three different embodiments were used to enrich for and sequence the D-loop region. First, a nucleic acid sample containing both genomic and mitochondrial genomes was digested using BsmAI, a type IIs restriction enzyme that produces fragments having random four-base overhangs. This digestion produces ~2.9 million fragments, including a 2.4 kb fragment of the mitochondrial genome containing the 1,331 base pairs of the D-loop region flanked by 981 base pairs on one end and 61 base pairs on the other end of the fragment. The 2.9 million fragments generated in the digestion were subjected to a ligation reaction in the presence of T4 ligase and two different stem-loop adapters having different four-base overhangs, specifically, 5'-AAGA and 5'-TTCC. This ligation resulted in the production of ~45 thousand different fragments (~1/256) having only one of the adapters ligated to an end, ~88 different fragments (~2/65,536) having the same adapter ligated to both ends, and about 88 different fragments (~2/65,536) having one adapter on one end and the other adapter on the other end. The resulting mixture was treated with exonucleases (ExoIII and ExoVII) to digest linear fragments having no adapters or only one adapter. The mixture was also treated with endonucleases that do not have a recognition sequence within the 2.4 kb fragment comprising the D-loop region of interest, including, e.g., XmaI and BspQI. The endonuclease treatment provided additional exonuclease-sensitive termini to facilitate degradation of nucleic acids outside of the 2.4 kb fragment of interest. Following the nuclease treatment, the sample was subjected to a purification procedure using an Agencourt® AMPure® system (Beckman Coulter, Brea, Calif.). Only about 200 different fragments were recovered, including the 2.4 kb fragment of interest, and these fragments were subjected to single-molecule, real-time sequencing.

The second and third embodiments were similar to the first, but used different type IIs restriction enzymes. Using a combination of BsmAI and TspRI yielded a 1.43 kb fragment containing the 1,331 base pairs of the D-loop region flanked by 37 base pairs on one end and 61 base pairs on the other end of the fragment. Alternatively, using only BsaI yielded a 4.5 kb fragment containing the 1,331 base pairs of the D-loop region flanked by 2678 base pairs on one end and 522 base pairs on the other end of the fragment. In both cases, two different stem-loop adapters were used having four-base overhangs known to be complementary to the fragment of interest such that the fragment was flanked by one of the overhangs at one end and the other overhang at the other end. Also in both cases, ExoIII, ExoVII, and a set of restriction endonucleases were used to cleave and degrade fragments other than the desired fragment containing the D-loop region. Following the purification procedure, the resulting pool of fragments having adapters linked to both ends, which included the fragment of interest comprising the D-loop region, were subjected to single-molecule, real-time sequencing.

5. Enrichment and Sequencing of Targeted "CGG Repeat" Fragment of Human FMR1 Gene The human FMR1 gene codes for the "fragile X mental retardation protein" or FMRP, which is essential for normal cognitive development. The FMR1 gene is found on the long (q) arm of the X chromosome at position 27.3, from base pair 146,699,054 to base pair 146,738,156, and it contains a region comprising a CGG trinucleotide repeat. In most people, the CGG trinucleotide is repeated in the gene approximately 5-44 times. Expansion of the CGG repeat region can lead to various neurological conditions, including fragile X syndrome, mental retardation, autism, and Parkinson's disease. The number of repeats in the CGG region is directly related to the development of these disorders, with 55-200 repeats considered "premutation" and greater than 200 repeats considered a full mutation. The ability to count the number of repeats is therefore of value in determining the genetic predisposition of an individual, but enriching one region of one gene in a human genome is without PCR amplification, which can add or delete repeats in the resulting amplicons, is a challenge.

The goal of this study was to develop an enrichment strategy for the FMR1 region that did not require amplification to provide a long template molecule comprising the entire CGG repeat region and any base modifications therein.

In a first experimental strategy, a human genomic DNA sample was purified to remove trace amounts of RNA and ssDNA, and was digested to completion using excess restriction enzyme(s). In particular, the CGG region of the FMR1 gene was enriched by subjecting human genomic DNA to digestion with HgaI to produce genomic fragments having random five-base overhangs. This set of fragments included a 1195 bp fragment that comprises the CGG region of the FMR1 gene flanked by 359 bp at one end and 926 bp at the other end. This digestion generated ~2.9 million fragments averaging 1 kb in size. Two different stem-loop adapters having defined five-base overhangs (5'-CCGGG and 5'-GTGAA) were ligated to these fragments, and it was predicted that only three of these fragments would have complementary overhangs such that the first adapter was ligated to one end and the second adapter was ligated to the other end. Subsequent treatment with ~78 restriction endonucleases that do not cleave the 1089 fragment of interest and exonucleases (ExoIII and ExoVII) degraded fragments that were cleaved by the endonucleases and/or that were not capped at both ends by adapters. Following the nuclease treatment, the sample was subjected to a purification procedure using an Agencourt® AMPure® system (Beckman Coulter, Brea, Calif.) and subsequently subjected to single-molecule, real-time sequencing.

Figure 7:
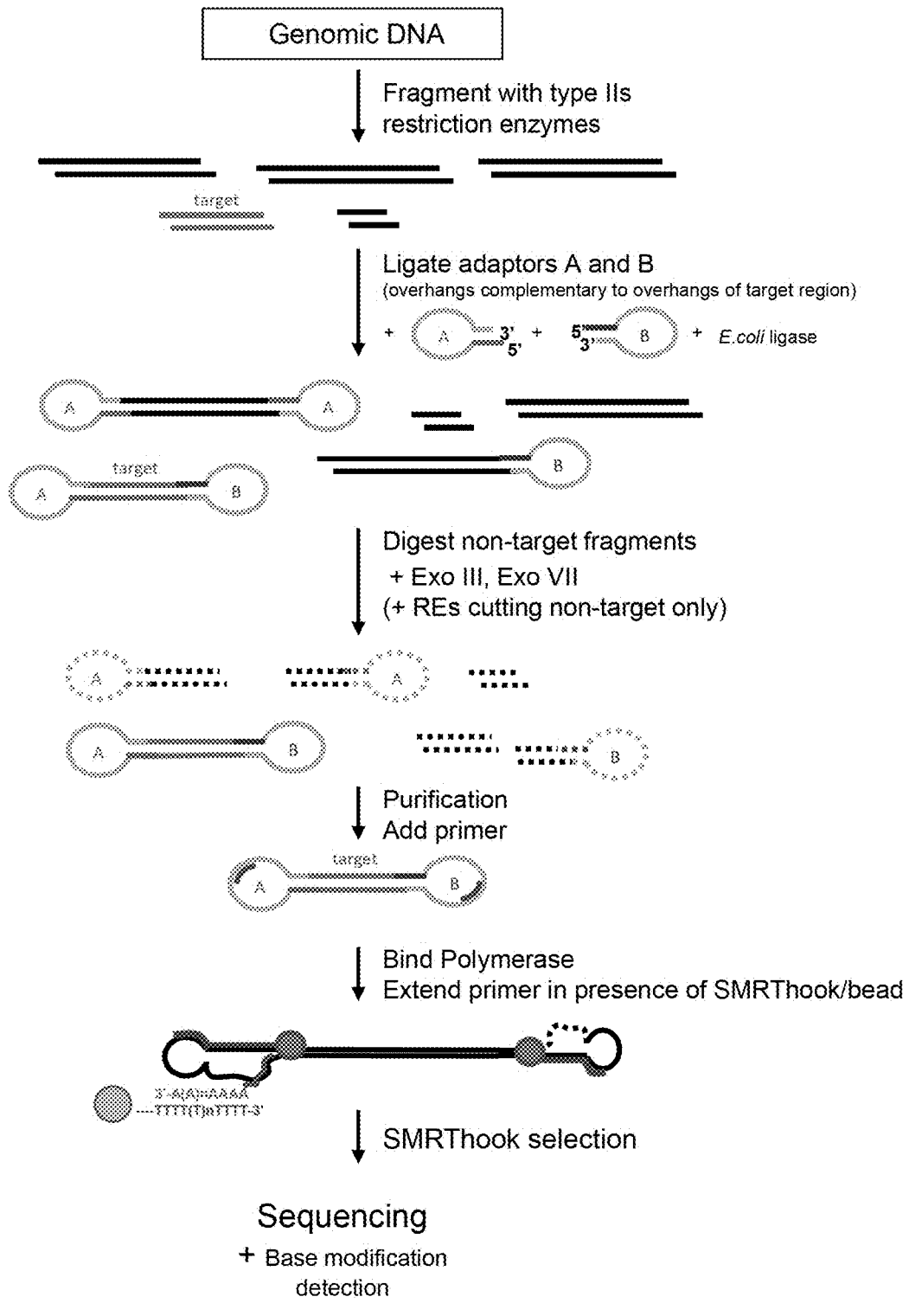
FIG. 7 illustrates an experimental strategy for enriching a target nucleic acid according to an embodiment provided herein.

A second experimental strategy is illustrated in FIG. 7. As in the first strategy, human genomic DNA samples were purified to remove trace amounts of RNA and ssDNA, and were digested to completion using excess restriction enzyme(s). In the second strategy, the CGG region of the FMR1 gene was enriched by subjecting human genomic DNA to digestion with about 5 units of BsmAI (from NEB), a type IIs restriction enzyme, per microgram of gDNA using NEBuffer 4. The digestion, carried out on about 20 µg/mL DNA, was done at 55° C. for ~16 hrs. to produce ~2.9 million different genomic fragments having random four-base overhangs. This set of fragments included a 1.1 kb "FMR1 fragment" that comprises the CGG region of the FMR1 gene flanked by 718 bp at one end and 334 bp at the other end. The completion of restriction enzyme digestion was verified by PCR using sets of primers across the restriction enzyme cut sites and monitoring the relative quantity of PCR products generated for unfragmented gDNA alone versus restriction-enzyme-digested gDNA. The target FMR1 fragments were isolated from other fragments in the mixture that were either greater than 3 kb or less than ~500 bp using an AMPure® magnetic-bead-based purification system according to manufacturer's instructions. The DNA fragments were further purified by two subsequent 75% ethanol washes, and were eluted from beads using 10 mM Tris-HCl, pH 8 (or EB buffer from Qiagen).

As illustrated in FIG. 7, two different stem-loop adapters having defined five-base overhangs (5'-CTGT and 5'-AATG) were ligated to these fragments using E. coli ligase. These overhangs were complementary to the overhangs produced at the ends of the target fragment by the type IIs restriction enzyme digestion. It was predicted that only about 88 of the genomic fragments produced by the digestion (including the target fragment) would have complementary overhangs such that the first adapter was ligated to one end and the second adapter was ligated to the other end. An excess of these two stem-loop adapters, relative to the concentration of DNA fragments in the purified sample containing the targeted fragment, were annealed to the ends of fragments, and E. coli ligase (NEB) was used to covalently link the adapters to the fragments using NEB-supplied 10× E. coli ligase buffer. The ligation tube was incubated for ~16 hours to produce a small number of fragments having an adapter at both ends and many thousands of non-target fragments having only one adapter. Millions of non-target fragments remained free of any adapter.

Subsequent treatment with a set of restriction endonucleases that do not cleave the 1.1 kb fragment of interest (including BsmAI) and exonucleases (ExoIII and ExoVII) degraded fragments that were cleaved by the endonucleases and/or that were not capped at both ends by adapters. Since the BsmAI recognition site is outside of the FMR1 fragment, the active BsmAI that remained in the preparation significantly reduced (by ~75%) the number of non-target molecules that were ligated to the adapter sequences. The final enrichment was estimated to be ~66,000-fold in ~20 ng of enriched nucleic acids. Following the nuclease treatment, the sample was subjected to a purification procedure using an Agencourt® AMPure® system (Beckman Coulter, Brea, Calif.), and primer was annealed to the single stranded DNA region on at least one of the stem-loop adapter. The primer was used for polymerase binding and was extended by the polymerase during subsequent DNA synthesis. The ratio of primer concentration to the target fragment or "template" concentration was optimized such that all templates with hairpin adapters were expected to have at least one or two primers per template. The templates having one or two primers annealed thereto are termed "primed templates." A polymerase enzyme was added to the primed templates in slight excess, e.g., 3-10×, to produce polymerase-template complexes having polymerase bound at the 3'-end of the primer.

The target fragments were further enriched using a bead-based hybridization strategy termed "capture-hook enrichment." Capture-hook enrichment and related enrichment strategies and can be used with the methods herein are further described in U.S. patent application Ser. No. 13/427,725, filed Mar. 22, 2012. Briefly, the polymerase was allowed to begin processing the double-stranded FMR1 fragment, which revealed single-stranded sequence in the strand that was displaced by the polymerase. Reaction conditions were controlled such that the polymerase only processed about 30-50 bases of the template before being stopped, e.g., by addition of EDTA. Magnetic beads present in the mixture were linked to single-stranded oligonucleotides (capture-hook oligonucleotides) that were complementary to about 15-25 bases of the single-stranded sequence revealed by polymerase strand displacement, and these oligonucleotides hybridized to this single-stranded sequence of polymerase-template complex, thereby attaching it to the magnetic bead. This magnetic-bead-linked complex was introduced to a substrate that specifically bound to the polymerase enzyme, pulling the complex off the bead and onto a reaction site where polymerase-mediated, single-molecule sequencing was observed in real time by "SMRT Sequencing." The capture-hook oligos were complementary to at least a portion of the FMR1 target fragment, so other non-target fragments still present were unlikely to bind to the capture-hook oligo and were removed from the mixture, e.g., by washing the immobilized magnetic beads. The retained complexes attached to the beads, comprising highly enriched target templates, were subjected to single-molecule, real-time sequencing reactions on a PacBio® RS system. The results of the additional capture-hook enrichment method showed that the numbers of sequenced non-target templates were reduced from hundreds to 20 or less.

Figure 8:
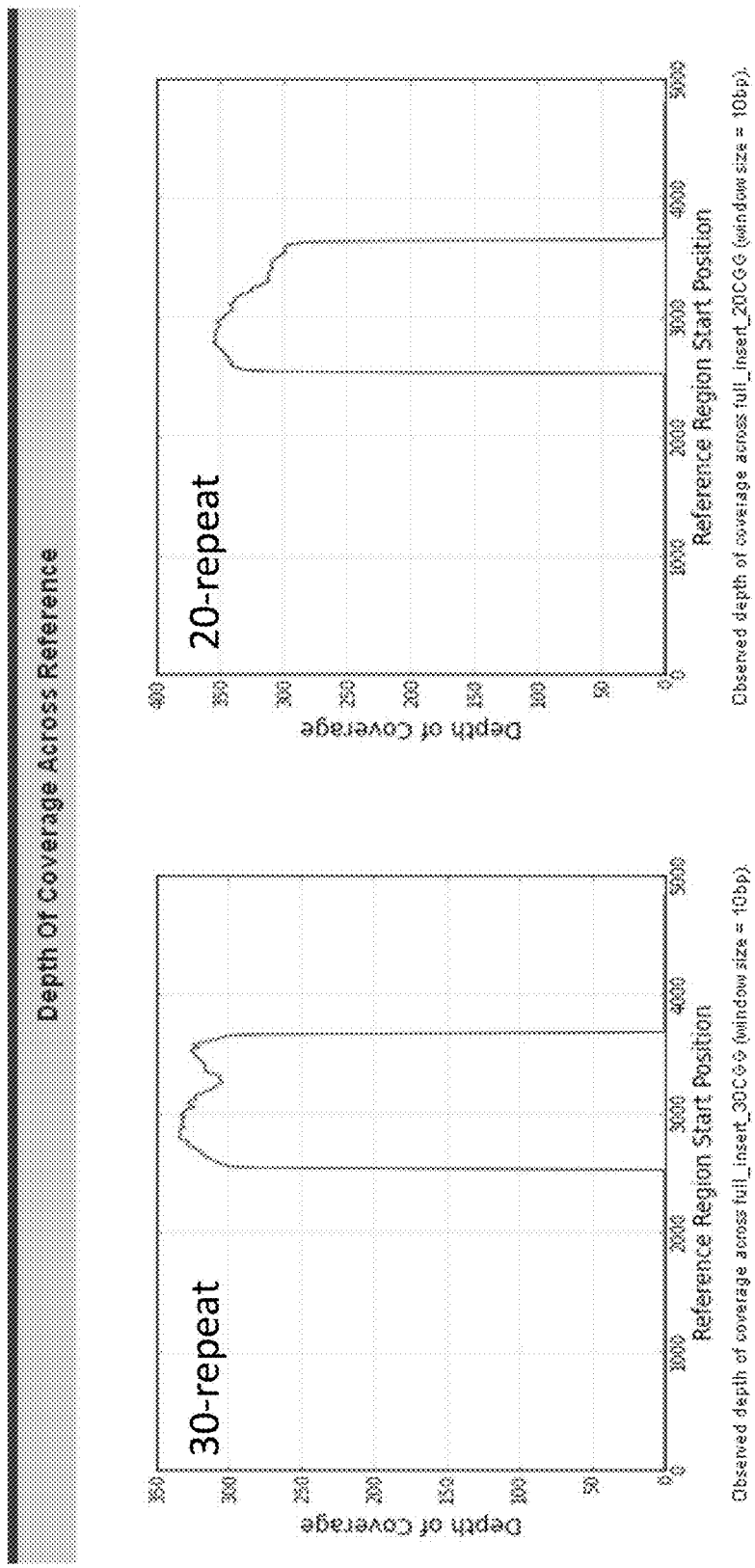
FIG. 8 provides a graphic representation of enrichment data generated by an embodiment of an enrichment strategy described herein.
Figure 9A:
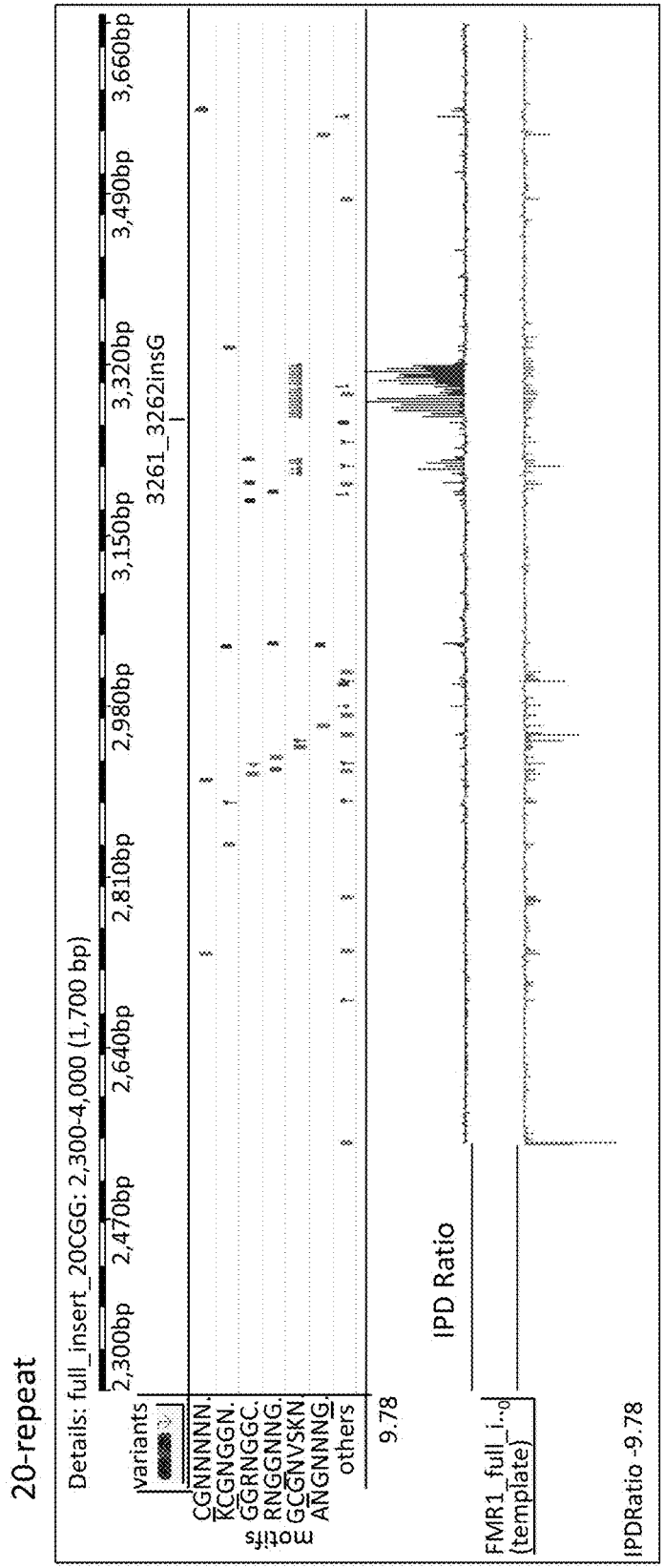
FIGS. 9A-9B provide a graphic representation of the kinetics of polymerase-mediated sequencing reactions performed on homologous chromosomes.
Figure 9B:
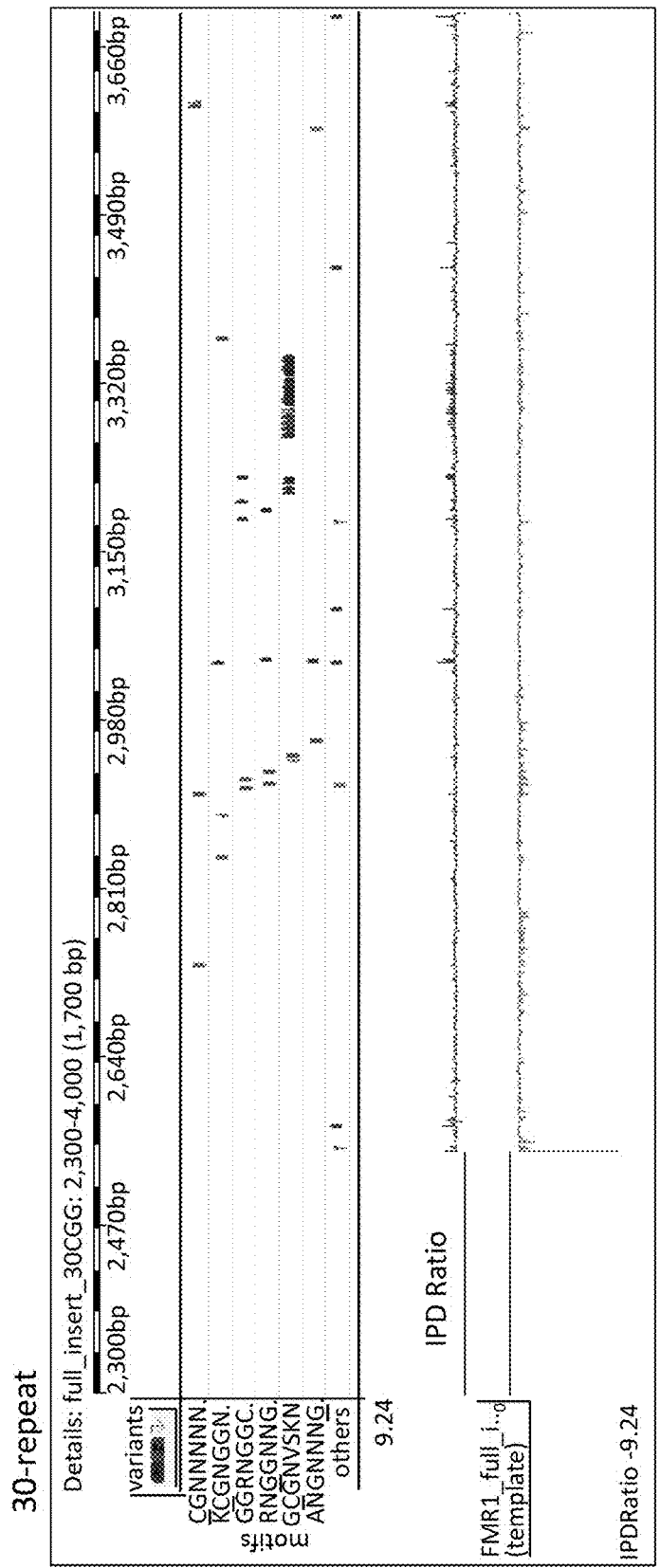

The vast majority of the sequencing reads generated mapped to the FMR1 region as there were very few off-target reads. Analysis of the sequencing reads that mapped to the FMR1 region generated a consensus sequence having 100.0000% consensus accuracy. The source of the original genomic nucleic acid was female and so had two X chromosomes. One homolog had 20 copies of the CGG repeat, and the other homolog had 30 copies. The enrichment process enriched for both homologs as evidenced by the sequence data, which was generated from both in relatively even amounts, i.e., each had >300-fold coverage, as shown in FIG. 8. The allelic difference between the two homologs (i.e., the differing number of repeats) was evident in the sequencing results, and additionally mosaics were detected with 29 reads from the first homolog having 20±1 repeats, and 31 reads from the second homolog having 30±2 repeats. Further, there were differences in the kinetics of the polymerase enzyme during the sequencing reaction that suggested that there were base modifications present on at least one strand of the 20-repeat homolog (FIG. 9A) that were absent from either strand of the 30-repeat homolog (FIG. 9B). Further details on kinetic detection of base modifications is provided in U.S. Patent Publication No. 20110183320, which is incorporated herein in its entirety for all purposes.

The entire strategy (combination of adapter selection, nuclease treatment, and capture-hook enrichment) achieved a 207,143-fold enrichment of the 1.1 kb FMR1 fragment. From a beginning total of 2.9 million fragments, this fragment was one of only 14 remaining in the enriched pool. Sequencing of this preparation produced a set reads comprising >600-fold coverage for this region from a ~7.5 µg of genomic DNA. There was equal representation of both X chromosomes in these reads, demonstrating that the enrichment process can capture the FMR1 fragment equally from both X chromosomes. Further, analysis of the kinetics of the polymerase during the sequencing reaction showed a distinct difference between sequencing the homolog comprising the 20 CGG repeats as compared to the homolog comprising the 30 CGG repeats, and this difference was evident not only in the CGG repeat region, but also in the promoter region for this homolog. This finding suggests there may be a difference in the number of modified bases in each. Since the FMR1 gene is on the X chromosome, these differences could also be an indication of X-inactivation in this individual, where the 20-repeat homolog is being preferentially inactivated. This has yet to be confirmed, however.

In a further experiment, amplification using a rolling-circle strategy was tested with ~5 ng of sample genomic nucleic acid and found to have very little effect on the ratio of reads from each homolog, as both continued to be approximately equally represented as measured by the number of reads generated that corresponded to each. As expected, the amplified nucleic acid did not exhibit any significant kinetic differences during polymerase-mediated sequencing-by-synthesis because the amplification did not maintain any modifications that caused such a difference in the unamplified nucleic acids. The sequencing data from the amplified sample also served as a control for the kinetic differences observed in the sequencing data from the unamplified sample. The same method was also successfully used to sequence an FMR1 region comprising 125 CGG repeats, providing an over 2000-fold enrichment of the FMR1 target region (data not shown).

Although described in some detail for purposes of illustration and clarity, it will be readily appreciated from a reading of this disclosure that various changes in form and detail that are known or appreciated by those of skill in the art may be practiced without departing from the true scope of the invention. For example, all the techniques and apparatus described above can be used in various combinations, e.g., sequentially or simultaneously. All terms used herein are intended to have their ordinary meaning unless an alternative definition is expressly provided or is clear from the context used therein. To the extent any definition is expressly stated in a patent or publication that is incorporated herein by reference, such definition is expressly disclaimed to the extent that it is in conflict with the ordinary meaning of such terms, unless such definition is specifically and expressly incorporated herein, or it is clear from the context that such definition was intended herein. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all publications, patents, patent applications, and/or other documents referred to in this disclosure are incorporated herein by reference in their entireties for all purposes to the same extent as if each individual publication, patent, patent application, and/or other document were individually and separately indicated to be incorporated by reference for all purposes.

The invention claimed is:

1. A method for enrichment of a target region in a nucleic acid sample comprising:
   a) obtaining a nucleic acid sample comprising a mixture of double-stranded nucleic acid fragments, wherein a subset of fragments in the mixture comprises the target region;
   b) digesting the nucleic acid sample with a first endonuclease and a second endonuclease to produce a population of double-stranded nucleic acid fragments, wherein the first endonuclease cleaves a particular nucleotide sequence that is upstream of the target region and the second endonuclease cleaves a particular nucleotide sequence that is downstream of the target region;
   c) ligating stem-loop adapters to the population of double-stranded nucleic acid fragments to produce a ligated sample; and
   d) treating the ligated sample with: (i) one or more third endonucleases that do not cleave stem-loop ligated double-stranded nucleic acid fragments that include the target region, and (ii) one or more exonucleases that digest double-stranded nucleic acid fragments cleaved by the one or more third endonucleases, having one stem-loop adapter ligated thereto, or having no stem-loop adapter ligated thereto, thereby enriching for the target region in the nucleic acid sample.

2. The method of claim 1, wherein a primer binding sequence is present within the stem-loop adapter.

3. The method of claim 2, further comprising hybridizing a primer to the primer binding sequence in the enriched double-stranded nucleic acid fragments and exposing the primer-hybridized double-stranded nucleic acid fragments to a polymerase enzyme to generate a polymerase complex.

4. The method of claim 3, further comprising exposing the polymerase complex to a capture-hook oligonucleotide attached to a magnetic bead to selectively capture the polymerase complex.

5. The method of claim 4, wherein the capture-hook oligonucleotide only captures an active polymerase complex by binding to a region of the nucleic acid in the polymerase complex that has been rendered single-stranded by the polymerase enzyme.

6. The method of claim 1, further comprising performing template-directed sequencing-by-synthesis on the enriched nucleic acid fragments.

7. The method of claim 6, wherein the template-directed sequencing-by-synthesis generates redundant sequence information from single molecules of the enriched nucleic acid fragments.

8. The method of claim 1, further comprising isolating fragments having an approximate size of a double-stranded nucleic acid fragment comprising the target region generated by digestion with the first endonuclease and a second endonuclease prior to the ligating step.

9. The method of claim 1, wherein the first endonuclease and the second endonuclease are selected from the group consisting of: a type II restriction endonuclease, a type IIs restriction endonuclease, an engineered endonuclease, and any combination thereof.

10. The method of claim 9, wherein the engineered endonuclease is an engineered zinc finger DNA-binding protein endonuclease.

11. The method of claim 9, wherein the first endonuclease and the second endonuclease are engineered endonucleases.

12. The method of claim 1, wherein the first endonuclease, the second endonuclease, or both leave ends with single-stranded overhangs.

13. The method of claim 12, wherein:
the first endonuclease leaves a first single-stranded overhang and the second endonuclease leaves a second single-stranded overhang, wherein the first single-stranded overhang and the second single-stranded overhang are different; and
the stem-loop adapters comprise first stem-loop adapters and second stem-loop adapters, wherein the first stem-loop adapters comprise a single-stranded overhang that is complementary to the first single-stranded overhang and the second stem-loop adapters comprise a single-stranded overhang that is complementary to the second single-stranded overhang.

14. The method of claim 1, wherein the first endonuclease, the second endonuclease, or both leave blunt ends.

15. The method of claim 1, wherein the target region comprises repetitive sequences.

16. The method of claim 15, wherein the repetitive sequences are repeat sequences associated with a genetic disorder.

17. The method of claim 16, wherein the genetic disorder is selected from the group consisting of: fragile X syndrome, fragile X-associated tremor/ataxia syndrome (FXTAS), amyotrophic lateral sclerosis (ALS), frontotemporal dementia (FTD), Parkinson's disease, autism, cancer, myotonic dystrophy, ataxia, epilepsy, and Huntington's disease.

18. The method of claim 1, wherein multiple different target regions are enriched in the nucleic acid sample.

* * * * *

SEQUENCE LISTING

```
<160> NUMBER OF SEQ ID NOS: 17

<210> SEQ ID NO 1
<211> LENGTH: 10
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (6)..(10)
<223> OTHER INFORMATION: n is a, c, g, or t

<400> SEQUENCE: 1 gtctcnnnnn                                                            10

<210> SEQ ID NO 2
<211> LENGTH: 10
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (1)..(5)
<223> OTHER INFORMATION: n is a, c, g, or t

<400> SEQUENCE: 2 nnnnngagac                                                            10

<210> SEQ ID NO 3
<211> LENGTH: 14
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (6)..(14)
<223> OTHER INFORMATION: n is a, c, g, or t

<400> SEQUENCE: 3
gcatcnnnnn nnnn                                                       14

<210> SEQ ID NO 4
<211> LENGTH: 14
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (1)..(9)
<223> OTHER INFORMATION: n is a, c, g, or t

<400> SEQUENCE: 4
nnnnnnnnng atgc                                                       14
```

```
<210> SEQ ID NO 5
<211> LENGTH: 11
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (7)..(11)
<223> OTHER INFORMATION: n is a, c, g, or t

<400> SEQUENCE: 5
ggtctcnnnn n                                                          11

<210> SEQ ID NO 6
<211> LENGTH: 11
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (1)..(5)
<223> OTHER INFORMATION: n is a, c, g, or t

<400> SEQUENCE: 6
nnnnngagac c                                                          11

<210> SEQ ID NO 7
<211> LENGTH: 11
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (7)..(11)
<223> OTHER INFORMATION: n is a, c, g, or t

<400> SEQUENCE: 7
cgtctcnnnn n                                                          11

<210> SEQ ID NO 8
<211> LENGTH: 11
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (1)..(5)
<223> OTHER INFORMATION: n is a, c, g, or t

<400> SEQUENCE: 8
nnnnngagac g                                                          11

<210> SEQ ID NO 9
<211> LENGTH: 14
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (7)..(14)
<223> OTHER INFORMATION: n is a, c, g, or t

<400> SEQUENCE: 9
acctgcnnnn nnnn                                                       14
```

```
<210> SEQ ID NO 10
<211> LENGTH: 14
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (1)..(8)
<223> OTHER INFORMATION: n is a, c, g, or t

<400> SEQUENCE: 10
nnnnnnnncc aggt                                                        14

<210> SEQ ID NO 11
<211> LENGTH: 11
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (8)..(11)
<223> OTHER INFORMATION: n is a, c, g, or t

<400> SEQUENCE: 11
gctcttcnnn n                                                           11

<210> SEQ ID NO 12
<211> LENGTH: 11
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (1)..(4)
<223> OTHER INFORMATION: n is a, c, g, or t

<400> SEQUENCE: 12
nnnngaagag c                                                           11

<210> SEQ ID NO 13
<211> LENGTH: 15
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (6)..(15)
<223> OTHER INFORMATION: n is a, c, g, or t

<400> SEQUENCE: 13
gacgcnnnnn nnnnn                                                       15

<210> SEQ ID NO 14
<211> LENGTH: 15
<212> TYPE: DNA
<213> ORGANISM: Artificial Sequence
<220> FEATURE:
<223> OTHER INFORMATION: Exemplary cut site for restriction enzyme
<220> FEATURE:
<221> NAME/KEY: misc_feature
<222> LOCATION: (1)..(10)
<223> OTHER INFORMATION: n is a, c, g, or t

<400> SEQUENCE: 14
```

```
nnnnnnnnnn gcgtc                                                        15

<210> SEQ ID NO 15
<211> LENGTH: 27
<212> TYPE: DNA
<213> ORGANISM: Artificial Sequence
<220> FEATURE:
<223> OTHER INFORMATION: polyA region
<220> FEATURE:
<221> NAME/KEY: misc_feature
<222> LOCATION: (1)..(2)
<223> OTHER INFORMATION: n is a, c, g, or t

<400> SEQUENCE: 15
nnaaaaaaaa aaaaaaaaaa aaaaatt                                           27

<210> SEQ ID NO 16
<211> LENGTH: 31
<212> TYPE: DNA
<213> ORGANISM: Artificial Sequence
<220> FEATURE:
<223> OTHER INFORMATION: polyA region
<220> FEATURE:
<221> NAME/KEY: misc_feature
<222> LOCATION: (1)..(6)
<223> OTHER INFORMATION: n is a, c, g, or t

<400> SEQUENCE: 16
nnnnnnaaaa aaaaaaaaaa aaaaaaaaat t                                      31

<210> SEQ ID NO 17
<211> LENGTH: 23
<212> TYPE: DNA
<213> ORGANISM: Artificial Sequence
<220> FEATURE:
<223> OTHER INFORMATION: polyA region

<400> SEQUENCE: 17
aaaaaaaaaa aaaaaaaaaa aaa                                               23
```